(12) United States Patent
Granoff et al.

(10) Patent No.: US 9,511,131 B2
(45) Date of Patent: Dec. 6, 2016

(54) CHIMERIC FACTOR H BINDING PROTEINS (FHBP) CONTAINING A HETEROLOGOUS B DOMAIN AND METHODS OF USE

(75

(56) References Cited

OTHER PUBLICATIONS

Fletcher, et al. (2004) "Vaccine potential of the Neisseria meningitidis 2086 lipoprotein" *Infect Immun.* 72(4):2088-2100.
GenBank Accession No. AY548370 "Neisseria meningitidis strain H44/76 lipoprotein (gnal870) gene, complete cds" (AAT01289.1) (from N. meningitidis strain H44/76), dated May 1, 2004.
GenBank Accession No. AY548371 "Neisseria meningitidis strain CU385 lipoprotein (gnal870) gene, complete cd" (AAT01290.1) (from N. meningitidis strain CU385), dated May 1, 2004.
GenBank Accession No. AY548372 "Neisseria meningitidis strain BZ83 lipoprotein GNA1870 (gnal870) gene, complete cd" (AAS56915.1) (from N. meningitidis strain BZ83), dated Apr. 22, 2004.
GenBank Accession No. AY548373 "Neisseria meningitidis strain 4243 lipoprotein GNA1870 (gnal870) gene, complete cd" (AAS56916.1) (from N. meningitidis strain 4243), dated Apr. 22, 2004.
GenBank Accession No. AY548374 "Neisseria meningitidis strain M6190 lipoprotein GNA1870 (gnal870) gene, complete cd" (AAS56917.1) (from N. meningitidis strain M6190), dated Apr. 22, 2004.
GenBank Accession No. AY548375 "Neisseria meningitidis strain N98/254 lipoprotein GNA1870 (gnal870) gene, complete cd" (AAS56918.1) (from N. meningitidis strain NZ98/254), dated Apr. 22, 2004.
GenBank Accession No. AY548376 "Neisseria meningitidis strain M1390 lipoprotein GNA1870 (gnal870) gene, complete cds" (AAS56919.1) (from N. meningitidis strain M1390), dated Apr. 22, 2004.
GenBank Accession No. AY548377 "Neisseria meningitidis strain M4105 lipoprotein GNA1870 (gnal870) gene, complete cd" (AAS56920.1) (fHbp ID 4 from N. meningitidis strain M4105), dated Apr. 22, 2004.
GenBank Accession No. NC_003112, "Neisseria meningitidis MC58, complete genom" GeneID: 904318 (NCBI Ref. NP_274866), fHbp ID 1 from N. meningitidis strain MC58, ), dated May 24, 2010.
GenBank Accession No. NP_000177 (P08603), and its encoding nucleic acid as NM_000186, "complement factor H isoform a precursor [*Homo sapiens*]" dated Mar. 21, 2010.
Giuliani, et al. (2005) "The region comprising amino acids 100 to 255 of Neisseria meningitidis lipoprotein GNA 1870 elicits bactericidal antibodies" *Infect. Immun.* 73(2):1151-1160.
Goldschneider, et al. (1969) "Human Immunity to the Meningococcus: I. The Role of the Humoral Antibodies" *J. Exp. Med.* 129(6):1307-1326.
Granoff, et al. (1998) "Bacterial Monoclonal Antibodies That Define Unique Meningococcal B Polysaccharide Epitopes That Do Not Cross-React with Human Polysialic Acid" *J. Immunol.* 160(10):5028-5036.
Granoff, et al. (2009) "Binding of complement factor H (fH) to Neisseria meningitidis is specific for human fH and inhibits complement activation by rat and rabbit sera" *Infect. Immun.* 77(2):764-769.

Masignani, et al. (2003) "Vaccination against Neisseria meningitidis using three variants of the lipoprotein GNA1870" *J. Exp. Med.* 197(6):789-799.
Pajon, et al. (2010) "Frequency of factor H-binding protein modular groups and susceptibility to cross-reactive bactericidal activity in invasive meningococcal isolates" *Vaccine* 28(9):2122-2129.
Scarselli, et al. (2009) "Epitope mapping of a bactericidal monoclonal antibody against the factor H binding protein of Neisseria meningitidis" J. Mol. Biol. 386(1):97-108.
Shaughnessy, et al. (2009) "Functional comparison of the binding of factor H short consensus repeat 6 (SCR 6) to factor H binding protein from Neisseria meningitidis and the binding of factor H SCR 18 to 20 to Neisseria gonorrhoeae porin" Infect. Immun. 77(5):2094-2103.
Welsch, et al. (2004) "Protective activity of monoclonal antibodies to genome-derived neisserial antigen 1870, a Neisseria meningitidis candidate vaccine" *J. Immunol.* 172(9):5606-5615.
Beernink, et al. (2007) "Prevalence of Factor H-Binding Protein Variants and NadA Among Meningococcal Group B Isolates from the United States: Implications for the Development of a Multicomponent Group B Vaccine" *J. Infect. Dis.* 195(10):1472-1479.
Fukasawa, et al., Immune Response to Naitive NadA from Neisseria Meningitidis and its Expression in Clinical Isolates in Mrazil, Journal of Medical Microbiology, 2003, 52:121-125.
Genbank Accession No. AAS56918 "Lipoprotein GNA1870 [Neisseria meningitidis]" dated Apr. 22, 2004.
Genbank Accession No. ABC59063 "Factor H Binding Protein [Neisseria meningitidis]" dated Jun. 20, 2006.
Genbank Accession No. ACI46937 "Factor H Binding Protein Variant A72_001 [Neisseria meningitidis]" dated Aug. 4, 2009.
Genbank Accession No. ACJ45782 "Factor H Binding Protein [Neisseria meningitidis]" dated Nov. 23, 2008.
Genbank Accession No. ACZ93150 "Factor H Binding Protein [Neisseria meningitidis]" dated Dec. 15, 2009.
Genbank Accession No. ACZ93290 "Factor H Binding Protein [Neisseria meningitidis]" dated Dec. 15, 2009.
Lewis, et al. (2010) "The Meningococcal Vaccine Candidate Neisserial Surface Protein A (NspA) Binds to Factor H and Enhances Meningococcal Resistance to Complement" *PLoS Pathog.* 6(7):e1001027:1-20.
Madico, et al. (2006) "The Meningococcal Vaccine Candidate GNA1870 Binds the Complement Regulatory Protein Factor H and Enhances Serum Resistance" *J. Immunol.* 177:501-510.
Maslanka, et al. (1997) "Standardization and a Multilaboratory Comparison of Neisseria Meningitidis Serogroup A and C Serum Bactericidal Assays" *Clin. Diagn. Lab. Immunol.* 4(2):156-157.
Ngampasutadol, et al. (2007) "A Novel Interaction Between Factor H SCR 6 and the Meningococcal Vaccine Candidate GNA 1870: Implications for Meningococcal Pathogenesis and Vaccine Development" *Mol. Immunol.* 44(1-3):220. Abstract.
Ngampasutadol, et al. (2008) "Human Factor H Interacts Selectively with Neisseria Gonorrhoeae and Results in Species-Specific Complement Evasion" J. Immunol. 180(5):3426- 3435.
Schneider, et al. (2009) "Supplemental Methods for Neisseria Meningitides Recruits Factor H Using Protein Mimicry of Host Carbohydrates" *Nature* doi:10.1038/nature07769:1-17.

\* cited by examiner

Figure 4.

```
             ******  ***************.***********************************
v.2 8047     VAADIGARLADALTAPLDHKDKSLQSLTLDQSVRKNEKLKLAAQGAEKTYGNGDSLNTGKLK 69
Chimera I    VAADIGAGLADALTAPLDHKDKGLQSLTLDQSVRKNEKLKLAAQGAEKTYGNGDSLNTGKLK 69
Chimera II   VAADIGAGLADALTAPLDHKDKGLQSLTLDQSVRKNEKLKLAAQGAEKTYGNGDSLNTGKLK 69
v.1 MC58     VAADIGAGLADALTAPLDHKDKGLQSLTLDQSVRKNEKLKLAAQGAEKTYGNGDSLNTGKLK 69
             ************************************************************

**************************.**.***:.*:* *:*:::.. ..:::  *.*  :
v.2 8047     NDKVSRFDFIRQIEVDGQLITLESGEFQIYKDHSAVVALQIEKINNPDKIDSLINQRSFLV 131       "B"
Chimera I    NDKVSRFDFIRQIEVDGQLITLESGEFQVYKQSHSALTAFQTEQIQDSEHSGKMVAKRQFRI 131      Domain
Chimera II   NDKVSRFDFIRQIEVDGQLITLESGEFQVYKQSHSALTAFQTEQIQDSEHSGKMVAKRQFRI 131
v.1 MC58     NDKVSRFDFIRQIEVDGQLITLESGEFQVYKQSHSALTAFQTEQIQDSEHSGKMVAKRQFRI 131
             ****************************.**************************

..:.*****************************.********  *******************
v.2 8047     SGLGGEHTAFNQLPDG--KAEYHGKAFSSDDAGGKLTYTIDFAAKQGHGKIEHLKTPEQNVEL 193
Chimera I    GDIAGEHTAFNQLPDG--KAEYHGKAFSSDDAGGKLTYTIDFAAKQGHGKIEHLKTPEQNVEL 193
Chimera II   GDIAGEHTAFNQLPDG--KAEYHGKAFSSDDAGGKLTYTIDFAKKQGHGKIEHLKTPEQNVEL 193
v.1 MC58     GDIAGEHTSFDKLPEGGRATYRGTAFGSDDAGGKLTYTIDFAAKQGNGKIEHLKSPELNVDL 193
             ****.****:.:.*.*  :.*.*.**.******.********.**:***.**:**.*:*

***********************************************************
v.2 8047     AAAELKADEKSHAVILGDTRYGSEEKGTYHLALFGDRAQEIAGSATVKIGEKVHEIGIAGKQ 255
Chimera I    AAAELKADEKSHAVILGDTRYGSEEKGTYHLALFGDRAQEIAGSATVKIGEKVHEIGIAGKQ 255
Chimera II   AAAELKADEKSHAVILGDTRYGSEEKGTYHLALFGDRAQEIAGSATVKIGEKVHEIGIAGKQ 255
v.1 MC58     AAADIKPDGKRHAVISGSVLYNQAEKGSYSLGIFGGKAQEVAGSAEVKTVNGIRHIGLAAKQ 255
             ***::*.*.* **** *.. *.. **:*:*.:**  ***:****  **  *  :::**:*.**
```

Figure 8A

| Characteristics of strains | | | | |
|---|---|---|---|---|
| Strain[1] | Origin | ST complex (ST)[1] | Porin Protein Types[2] | |
| | | | PorB | PorA |
| H44/76 | Norway | ST-32 (32) | 15 | 1.7,16 |
| SK080 | California | ST-162 (162) | 3-73 | 1.22,14 |
| SK084 | California | ST-32 (32) | 3-24 | 1.7,16 |
| NZ98/254 | New Zealand | ST-41/44 (42) | 4 | 1.7-2,4 |
| SK141 | Tennessee | ST-213 (213) | 3-14 | 1.22,14 |
| 8047 | U.S. | ST-8 (8) | 2b | 1.5-1,2-2 |
| MD1435 | Maryland | ST-35 (35) | 339 | 1.22-1,14 |
| MD1321 | Maryland | ST-41/44 (44) | 3-45 | 1.7-1,1 |
| 03S-0658 | California | ST-32 (1364) | 3-38 | 1.7-2,13-1 |
| M1239 | U.S. | ST-41/44 (437) | 14 | P1.23,14 |
| SK104 | North Carolina | ST-162 (5748) (S5()(5748) | 3-73 | 1.22,14 |

[1] ST, Sequence Type, determined by multi-locus sequence typing
[2] Porin types determined by DNA sequencing of variable loop regions.

| Characteristics of fHbp expressed by strains. | | | | | | | | | | | |
|---|---|---|---|---|---|---|---|---|---|---|---|
| | | % AA Identity[2] | | | JAR mAb Reactivty[3] | | | | | | |
| | | | | | v.1 | v.1, 2, or 3 | v.2 or 3 | | | | |
| Strain | Variant[1] | v.1 | v.2 | v.3 | 1 | 3/5 | 10 | 11 | 13 | 32/35 | 33 | 36 |
| H44/76 | 1 | 100 | 72 | 59 | 1 | 1 | 0 | 0 | 0 | 0 | 0 | 0 |
| SK080 | 1 | 93 | 69 | 61 | 0 | 1 | 0 | 0 | 0 | 0 | 0 | 0 |
| SK084 | 1 | 96 | 72 | 61 | 0 | 1 | 0 | 0 | 0 | 0 | 0 | 0 |
| NZ98/254 | 1 | 91 | 74 | 61 | 0 | 1 | 1 | 0 | 0 | 0 | 0 | 0 |
| SK141 | 1 | 89 | 71 | 63 | 0 | 1 | 1 | 0 | 0 | 0 | 0 | 0 |
| 8047 | 2 | 72 | 100 | 85 | 0 | 0 | 1 | 1 | 1 | 0 | 0 | 1 |
| MD1435 | 2 | 72 | 99 | 86 | 0 | 0 | 1 | 1 | 1 | 0 | 0 | 1 |
| MD1321 | 2 | 72 | 94 | 84 | 0 | 0 | 1 | 1 | 0 | 0 | 0 | 1 |
| 03S-0658 | 2 | 69 | 94 | 88 | 0 | 0 | 0 | 0 | 0 | 1 | 1 | 1 |
| M1239 | 3 | 59 | 85 | 100 | 0 | 0 | 0 | 0 | 1 | 1 | 1 | 1 |
| SK104 | 3 | 59 | 85 | 97 | 0 | 0 | 0 | 0 | 1 | 1 | 1 | 1 |

[1] Determined by quantitative PCR as described previously (Beernink et al., Clin Vacc Immunol 13(7):758-763).
[2] As compared with amino acid sequence of the mature protein with that of prototype fHBP: v.1, strain MC58; v.2, strain 8047; or v.3, strain M1239.
[3] mAb reactivity as determined by ELISA (see Materials and Methods). JAR 1 and 5 are from a mouse immunized with fHBP v.1 (strain MC58); JAR 10, 11 and 13 were from a mouse immunized with fHBP v.2 (strain 2996); JAR 32, 33 and 36 were from a mouse immunized with fHBP v.3 (strain M1239). All react with the respective fHBP used as the immunogen (see Table in Figure 17).

Figure 8B

| Amino acid sequence identity by antigenic variant group, strain and domain of fHbp | | | | | | | | | | | | | | | |
|---|---|---|---|---|---|---|---|---|---|---|---|---|---|---|---|
| | | Amino acid sequence identity, percent[1] | | | | | | | | | | | | | |
| | | A domain | | | B domain[2] | | | | | | | | | C domain | | |
| | | AA 1-100[2] | | | AA 101-135 | | | AA 101-164 | | | AA 136-164 | | | AA 165-255 | | |
| Strain | Variant[4] | v.1 | v.2 | v.3 | v.1 | v.2 | v.3 | v.1 | v.2 | v.3 | v.1 | v.2 | v.3 | v.1 | v.2 | v.3 |
| H44/76 | 1 | 100 | 97 | 77 | 100 | 28 | 28 | 100 | 46 | 42 | 100 | 67 | 60 | 100 | 59 | 52 |
| NZ98/254 | 1 | 99 | 98 | 76 | 85 | 31 | 31 | 85 | 47 | 44 | 86 | 67 | 60 | 83 | 61 | 53 |
| 8047 | 2 | 97 | 100 | 76 | 28 | 100 | 94 | 46 | 100 | 93 | 67 | 100 | 92 | 59 | 100 | 85 |
| 03S-0658 | 2 | 99 | 98 | 78 | 28 | 100 | 94 | 42 | 95 | 95 | 60 | 89 | 96 | 52 | 83 | 90 |
| M1239 | 3 | 77 | 76 | 100 | 28 | 94 | 100 | 42 | 93 | 100 | 60 | 92 | 100 | 52 | 85 | 100 |
| SK104 | 3 | 77 | 76 | 100 | 28 | 100 | 94 | 44 | 95 | 95 | 64 | 89 | 96 | 52 | 84 | 91 |

[1] As compared with amino acid (AA) sequence of the mature protein with that of prototype fHBP: v. 1, strain MC58; v. 2, strain 8047; or v.3, strain M1239.
[2] 101-164, B domain as defined by Giuliani et al., Infect. Immun., 2005; 101-135, B domain up to junction point of Chimera I or II (referred to as the N-terminal portion of B domain); 136-164, B domain starting at junction point ending at the C domain (referred to as the C-terminal portion of B domain).
[3] Numbering of AA is based on the mature protein (i.e. lacking the signal sequence) from strain MC58.
[4] Determined by quantitative PCR as described previously (Beernink et al., Clin Vacc Immunol 13(7):758-763).

Figure 13.

```
            <-- C-terminal portion of fHbpN --->     <-- fHbpC
                                                    ααα
MC58     101 QSHSALTAFQTEQIQDSEHSGKMVAKRQFRIGDIA GEHT SFDKLPE 146
M4105    101 QSHSALTALQTEQVQDSEHSGKMVAKRQFRIGDIA GEHT SFDKLPE 146
4243     101 QSHSALTALQTEQVQDSEDSGKMVAKRQFRIGDIA GEHT SFDKLPK 146
M6190    101 QSHSALTALQTEQVQDSEHSRKMVAKRQFRIGDIA GEHT SFDKLPK 146
NZ98/254 101 QSHSALTALQTEQEQDPEHSGKMVAKRRFKIGDIA GEHT SFDKLPK 146
NM452    101 QSHSALTALQTEQVQDSEHSGKMVAKRQFRIGDIV GEHT SFGKLPK 146
CDC1573  101 QSHSALTALQTEQEQDPEHSEKMVAKRRFRIGDIA GEHT SFDKLPK 146
03S-0408 101 QSHSALTALQTEQVQDSEHSGSMVAKRQFRIGDIA GEHT SFDKLPE 146
             ********:****  **.*.*  *****:*:****  ****  **.***:
```

Figure 14.

```
                              JAR 11  ↓      ↓  JAR 10  ↓
                   ←---------------------- fHbpC ---------------------→
                   ←------B-domain------→|
8047       141 AFNQLPDGKAEYHGKAFSSDDAGGKLTYTIDFAAKQGHGKIEHLKTPEQNVELAAAELKA 200
M98-250572 141 AFNQLPDGKAEYHGKAFSSDDAGGKLTYTIDFAAKQGHGKIEHLKTPEQNVELAAAELKA 200
M98-250809 141 AFNQLPSGKAEYHGKAFSSDDAGGKLTYTIDFATKQGHGKIEHLKTPEQNVELAAAELKA 200
6557       141 AFNQLPSGKAEYHGKAFSSDDAGGKLTYTIDFAAKQGHGKIEHLKTPEQNVELASAELKA 200
FAM18      141 AFNQLPDGKAEYHGKAFSSDDPNGRLHYSIDFTKKQGYGRIEHLKTPEQNVELAAAELKA 200
C2120      141 AFNQLPGGKAEYHGKAFSSDDAGGKLTYTIDFASKQGHGKIEHLKTPEQNVELAAAELKA 200
M1239      141 AFNQLPGGKAEYHGKAFSSDDPNGRLHYSIDFTKKQGYGRIEHLKTLEQNVELAAAELKA 200
M98-250771 141 AFNQLPSGKAEYHGKAFSSDDAGGKLTYTIDFAAKQGHGKIEHLKTPEQNVELASAELKA 200
Ngo_FA1090 141 AFNQLPDGKAEYHGKAFSSDDADGKLTYTIDFAAKQGHGKIEHLKTPEQNVELASAELKA 200
               ******.*************..*:* *:***: ***:*:****** *******:*****

↓ JAR 13

←---------------------- fHbpC ---------------------→
8047       201 DEKSHAVILGDTRYGSEEKGTYHLALFGDRAQEIAGSATVKIGEKVHEIGIAGKQ 255
M98-250572 201 DEKSHAVILGDTRYGSEEKGTYHLALFGDRAQEIAGSATVEIGEKVHEIGIAGKQ 255
M98-250809 201 DEKSHAVILGDTRYGSEEKGTYHLALFGDRAQEIAGSATVKIGEKVHEIGIAGKQ 255
6557       201 DEKSHAVILGDTRYGGEEKGTYHLALFGDRAQEIAGSATVKIREKVHEIGIAGKQ 255
FAM18      201 DEKSHAVILGDTRYGGEEKGTYHLALFGDRAQEIAGSATVKIREKVHEIGIAGKQ 255
C2120      201 DEKSHAVILGDTRYGSEEKGTYHLALFGDRAQEIAGSATVKIGEKVHEIGIAGKQ 255
M1239      201 DEKSHAVILGDTRYGSEEKGTYHLALFGDRAQEIAGSATVKIGEKVHEIGIAGKQ 255
M98-250771 201 DEKSHAVILGDTRYGSEEKGTYHLALFGDRAQEIAGSATVKIREKVHEIGIAGKQ 255
Ngo_FA1090 201 DEKSHAVILGDTRYGGEEKGTYRLALFGDRAQEIAGSATVKIGEKVHEIGIADKQ 255
               ***************.******:****************:* ********.**
```

```
III  sv1 NZ98/254   TEQEQDPEHS GKMVAKRRFK IGDIAGEHTA FNQLP-DGKA EYHGKAFSSD  v2  8047
IV   v1  MC58       TEQIQDSEHS GKMVAKRQFR IGDIAGEHTA FNQLP-SGKA EYHGKAFSSD  sv2 RM1090
V    sv1 NZ98/254   TEQEQDPEHS GKMVAKRRFK IGDIAGEHTA FNQLP-SGKA EYHGKAFSSD  sv2 RM1090
```

Figure 17. Murine anti-fHBP monoclonal antibodies

| JAR MAb (Immunogen[1]) | Reactivity Across Variants (ELISA)[2] | Ig Isotype | Inhibits binding of fH[3] |
|---|---|---|---|
| (rfHBP v.1) | | | |
| 1 | v.1 (subset) | G3 | Yes |
| 3 | v.1 (nearly all) | G3 | Yes |
| 4 | v.1, v.2 (high reactivity) and v.3 (lower reactivity) | G2a | No |
| 5 | v.1 (nearly all) | G2b | Yes |
| (rfHBP v.2) | | | |
| 10 | v.1 (subset), v.2 (subset) and v. 3 (subset) | G1 | No |
| 11 | v.2 (subset) and v.3 (subset) | G2a | Partial |
| 13 | v. 2 (subset) and v.3 (all) | G2a | Yes |
| (rfHBP v.3) | | | |
| 32 | v. 3 and v.2 (subset) | G2a | Yes |
| 33 | v. 3 and v.2 (subset) | G2a | No |
| 35 | v.3 and v.2 (subset) | G2b | Yes |
| 36 | v.3 and v.2 (nearly all) | G2b | Partial |

[1]Mice were immunized with recombinant proteins expressed from the genes from *N. meningitidis* strains MC58 (v.1), 2996 (v.2) and M1239 (v.3). All MAbs show evidence of synergistic complement-mediated bactericidal activity when tested with a second MAbs (See Figure 18), which is evidence of recognition of surface-accessible epitopes.

[2]With exception of JAR 4, the results are based on antibody binding to bacterial cells from different strains as measured by ELISA and identification of their respective fHBP variant groups by RT-PCR (Beernink et al., Clin Vacc Immunol 13(7):758-763). The JAR 4 cross-reactivity is based on binding to purified recombinant proteins in an ELISA and flow cytometry with live bacterial cells (Welsch et al J Immunol 2004 172:5606-5615).

[3]Based on inhibition of binding of purified human fH to rfHBP by ELISA in the presence of JAR anti-fHBP mAb (see representative data in Figure 19).

Figure 18.

| Complement-mediated synergistic bactericidal activity of anti-fHBP mAbs[1] | | | | | |
|---|---|---|---|---|---|
| | Bactericidal Concentration$_{50}$, µg/ml[2] (strain NZ98/254, v.1) | | | | |
| JAR mAb (Ig Isotype) | 3 | 4 | 5 | 10 | |
| 3 (G3) | >50 | 1 | >50 | >50 | |
| 4 (G2a) | 1 | >50 | 4 | >50 | |
| 5 (G2b) | >50 | 4 | >50 | >50 | |
| 10 (G1) | >50 | >50 | >50 | >50 | |
| | Bactericidal Concentration$_{50}$, µg/ml (Strain 8047, v.2) | | | | |
| JAR mAb (Ig Isotype) | 4 | 10 | 11 | 13 | 36 |
| 4 (G2a) | >50 | >50 | 5 | 4 | >50 |
| 10 (G1) | >50 | >50 | 5 | >50 | >50 |
| 11 (G2a) | 5 | 5 | >50 | >50 | 1 |
| 13 (G2a) | 4 | >50 | >50 | >50 | 1 |
| 36 (G2a) | >50 | >50 | 1 | 1 | >50 |
| | Bactericidal Concentration$_{50}$, µg/ml (Strain M1239 v.3) | | | | |
| JAR mAb (Ig Isotype) | 13 | 32 | 33 | 35 | 36 |
| 13 (G2a) | >50 | >50 | >50 | >50 | 1 |
| 32 (G2a) | >50 | >50 | 1 | >50 | >50 |
| 33 (G2a) | >50 | 1 | >50 | 5 | >50 |
| 35 (G2b) | >50 | >50 | 5 | >50 | >50 |
| 36 (G2b) | 1 | >50 | >50 | >50 | >50 |

[1]JAR 3, 4 and 5 were from a mouse immunized with rfHBP v. 1. JAR 10, 11 and 13 were from a mouse immunized with fHBP v.2. JAR 32, 33, 35 and 36 were from a mouse immunized with rfHBP v.3 (See Table in Figure 17).
[2]Total concentration of two mAbs that resulted in 50% survival of bacteria after 60 min incubation with human complement as compared with CFU/ml at time 0. Data are shown only for mAb pairs for which the respective strain expressed epitopes recognized by both mAbs.

Figure 19.
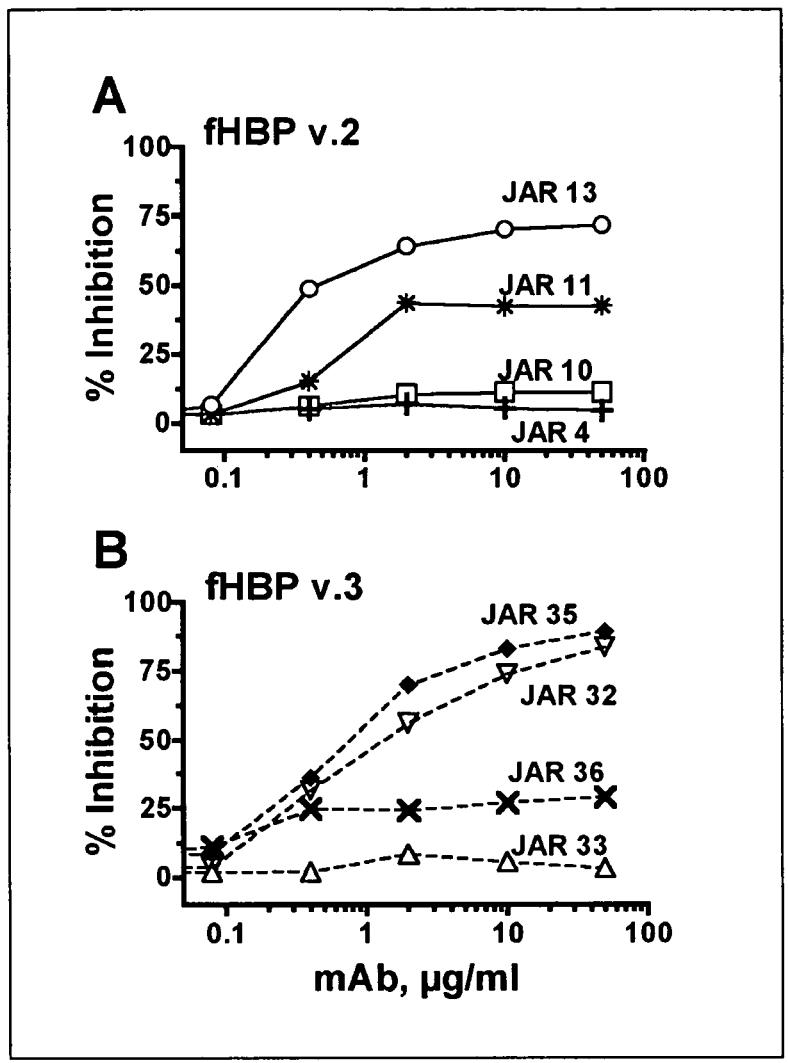
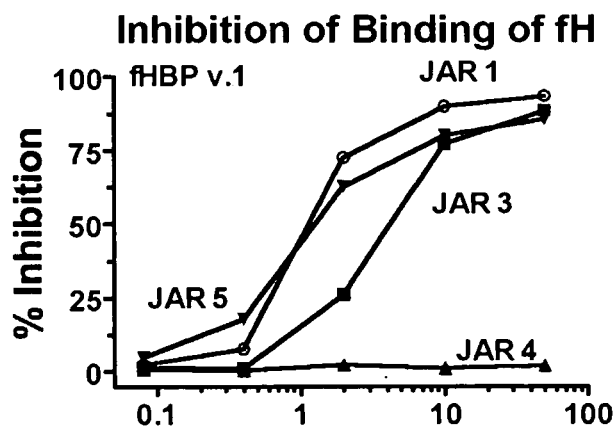

Figure 20

Bactericidal activity of combinations of mAbs in relation to the respective locations of the epitopes

| JAR MAB PAIR | Strain (variant) | Combination $BC_{50}$, µg/ml[1] | Residues in Epitopes[2] | Approximate Distance (Å)[3] | fH Inhibition[4] | Ig Isotype |
|---|---|---|---|---|---|---|
| Panel A (location of both epitopes known) | | | | | | |
| 5 and 502* | H44/76 | <1 | G121 and R204 | 16 | ++ and ND | G2b and G2a |
| 10 and 11 | 8047 (v.2) | 5 | K180/E192 and A174 | 18 to 20 | - and + | G1 and G2a |
| 33 and 32 | M1239 (v.3) | 1 | R180/E192 and K174 | 18 to 20 | - and ++ | G2a and G2a |
| 33 and 35 | M1239 (v.3) | 5 | R180/E192 and K174 | 18 to 20 | - and ++ | G2a and G2b |
| 3 and 10 | NZ98/254(v.1) | >50 | G121 and K180/E192 | 31 to 32 | ++ and - | G3 and G1 |
| 5 and 10 | NZ98/254(v.1) | >50 | G121 and K180/E192 | 31 to 32 | ++ and - | G2b and G1 |
| 13 and 35 | M1239 (v.3) | >50 | S216 and K174 | 27 | ++ and ++ | G2a and G2b |
| 13 and 11 | 8047 (v.2) | >50 | S216 and A174 | 27 | ++ and + | G2a and G2a |
| 13 and 32 | M1239 (v.3) | >50 | S216 and K174 | 27 | ++ and ++ | G2a and G2a |
| 13 and 33 | M1239 (v.3) | >50 | S216 and R180/E192 | 9 to 14 | ++ and - | G2a and G2a |
| 13 and 10 | 8047 (v.2) | >50 | S216 and K180/E192 | 9 to 14 | ++ and - | G2a and G1 |
| 3 and 5 | NZ98/254(v.1) | >50 | G121 and G121 | 0 | ++ and ++ | G3 and G1 |
| 32 and 35 | M1239 (v.3) | >50 | K174 and K174 | 0 | ++ and ++ | G2a and G2b |
| Panel B (location of one epitope unknown) | | | | | | |
| 4 and 3 | NZ98/254(v.1) | 1 | Unknown + G121 | Unknown | - and ++ | G2a and G2b |
| 4 and 5 | NZ98/254(v.1) | 4 | Unknown + G121 | Unknown | - and ++ | G2a and G2b |
| 4 and 10 | NZ98/254(v.1) | >50 | Unknown + K180/E192 | Unknown | - and - | G2a and G1 |
| 4 and 10 | 8047 (v.2) | >50 | Unknown + K180/E192 | Unknown | - and - | G2a and G1 |
| 4 and 11 | 8047 (v.2) | 5 | Unknown + A174 | Unknown | - and + | G2a and G2a |
| 4 and 13 | 8047 (v.2) | 4 | Unknown + S216 | Unknown | - and ++ | G2a and G2a |
| 36 and 13 | 8047 (v.2) | 1 | Unknown + S216 | Unknown | + and ++ | G2b and G2a |
| 36 and 33 | M1239 (v.3) | >50 | Unknown + R180/E192 | Unknown | + and - | G2b and G2a |
| 36 and 32 | M1239 (v.3) | >50 | Unknown + K174 | Unknown | + and ++ | G2b and G2b |
| 36 and 35 | M1239 (v.3) | >50 | Unknown + K174 | Unknown | + and ++ | G2b and G2a |

[1] Data are shown only for mAbs that individually are not bactericidal against low fHbp-expressing strains ($BC_{50}$ >50 µg/ml). Panel A shows all combinations for which we have identified respective amino acid residues that affect epitope recognition by each of the mAbs in the pair. *The R204 residue involved in expression of the mAb 502 epitope was described by Giuliani et al (Giuliani et al. 2005. Infect Immun 73:1151-1160). Panel B shows remaining combinations where the location of the epitope is known for only one of the two mAbs in the pair.
[2]For the respective mAbs in the pair. The numbering is based on amino acid sequence of MC58 v.1 fHbp lacking the signal sequence (Masignani et al. 2003 J Exp Med 197:789-799). Note that in reality, the amino acid sequences of the v.2 protein (strain 8047) and v.3 fHbp (strain M1239) differ by -1 and +7 amino acid residues, respectively, from that of MC58.
[3]Distances between pairs of the mAbs were calculated between alpha-carbon positions for the respective residues using PyMol (www.pymol.org). JAR 32 and JAR 35 recognize overlapping (or identical) epitopes including residue K174.
[4]For the respective mAbs in the pair: "++", inhibition of fH binding (>70%); "+", partial inhibition (25 to 45%); "-", no inhibition (<15%) (See, for example Fig. 19, above). ND, not determined.

Figure 22

Panel A
B domain of v.1 fHBP (MC58)

|← N-term portion > | < C-term portion --->|

QSHSALTAFQTEQI*QDSEHS*GKMVAKRQFRIGDIA *GEHT* *SFD*KLPEGGRATYRGTAFGSDDAGG

↑ ααα ↑

AH2

Panel B
C Domain

|<- --------------- C- terminal portion ------------------------------------→|

LTYTIDFA AKQGNGKIEHLKSPELNVDLAAADIKPDGKRHAVISGSVLYNQAEKGSYSLGIFGGKAQEVAGSAEVKTVNGIRHIGLAAKQ

↑

N-term portion

Figure 23. Chimera I (MC58/8047) nucleotide and protein sequences.

gtcgccgccgacatcggtgcggggcttgccgatgcactaaccgcaccgct
cgaccataaagacaaaggtttgcagtctttgacgctggatcagtccgtca
ggaaaaacgagaaactgaagctggcggcacaaggtgcggaaaaacttat
ggaaacggtgacagcctcaatacgggcaaattgaagaacgacaaggtcag
ccgtttcgactttatccgccaaatcgaagtggacgggcagctcattacct
tggagagtggagagttccaagtatacaaacaaagccattccgccttaacc
gcctttcagaccgagcaaatacaagattcggagcattccgggaagatggt
tgcgaaacgccagttcagaatcggcgacatagcgGGAGAACATACCGCCT
TCAACCAACTGCCTGACGGCAAAGCCGAGTATCACGGCAAAGCATTCAGC
TCCGACGATGCTGGCGGAAAACTGACCTATACCATAGATTTCGCCGCCAA
ACAGGGACACGGCAAAATCGAACACCTGAAAACACCCGAGCAAAATGTCG
AGCTTGCCGCCGCCGAACTCAAAGCAGATGAAAAATCACACGCCGTCATT
TTGGGCGACACGCGCTACGGCAGCGAAGAAAAGGCACTTACCACCTCGC
CCTTTTCGGCGACCGCGCCCAAGAAATCGCCGGCTCGGCAACCGTGAAGA
TAGGGGAAAAGGTTCACGAAATCGGCATCGCCGGCAAACAGTAG vaadigagladaltapldhkdkglqsltldqsvrkneklklaaqgaekty
gngdslntgklkndkvsrfdfirqievdgqlitlesgefqvykqshsalt
afqteqiqdsehsgkmvakrqfrigdiaGEHTAFNQLPDGKAEYHGKAFS
SDDAGGKLTYTIDFAAKQGHGKIEHLKTPEQNVELAAAELKADEKSHAVI
LGDTRYGSEEKGTYHLALFGDRAQEIAGSATVKIGEKVHEIGIAGKQ*

Figure 24. Chimera II (MC58/8047 A174K) nucleotide and protein sequences.

gtcgccgccgacatcggtgcggggcttgccgatgcactaaccgcaccgct
Cgaccataaagacaaaggtttgcagtctttgacgctggatcagtccgtca
Ggaaaaacgagaaactgaagctggcggcacaaggtgcggaaaaacttat
Ggaaacggtgacagcctcaatacgggcaaattgaagaacgacaaggtcag
Ccgtttcgactttatccgccaaatcgaagtggacgggcagctcattacct
Tggagagtggagagttccaagtatacaaacaaagccattccgccttaacc
Gcctttcagaccgagcaaatacaagattcggagcattccgggaagatggt
tgcgaaacgccagttcagaatcggcgacatagcgGGAGAACATACCGCCT
TCAACCAACTGCCTGACGGCAAAGCCGAGTATCACGGCAAAGCATTCAGC
TCCGACGATGCTGGCGGAAAACTGACCTATACCATAGATTTCGCCAAAAA
ACAGGGACACGGCAAAATCGAACACCTGAAAACACCCGAGCAAAATGTCG
AGCTTGCCGCCGCCGAACTCAAAGCAGATGAAAAATCACACGCCGTCATT
TTGGGCGACACGCGCTACGGCAGCGAAGAAAAGGCACTTACCACCTCGC
CCTTTTCGGCGACCGCGCCCAAGAAATCGCCGGCTCGGCAACCGTGAAGA
TAGGGGAAAAGGTTCACGAAATCGGCATCGCCGGCAAACAGTAG vaadigagladaltapldhkdkglqsltldqsvrkneklklaaqgaekty
gngdslntgklkndkvsrfdfirqievdgqlitlesgefqvykqshsalt
afqteqiqdsehsgkmvakrqfrigdiaGEHTAFNQLPDGKAEYHGKAFS
SDDAGGKLTYTIDFAKKQGHGKIEHLKTPEQNVELAAAELKADEKSHAVI
LGDTRYGSEEKGTYHLALFGDRAQEIAGSATVKIGEKVHEIGIAGKQ*

Figure 25. Chimera IIb (MC58/8047 A174K/K180R) nucleotide and protein sequences

```
gtcgccgccgacatcggtgcggggcttgccgatgcactaaccgcaccgct
Cgaccataaagacaaaggtttgcagtctttgacgctggatcagtccgtca
Ggaaaaacgagaaactgaagctggcggcacaaggtgcggaaaaaacttat
Ggaaacggtgacagcctcaatacgggcaaattgaagaacgacaaggtcag
Ccgtttcgactttatccgccaaatcgaagtggacgggcagctcattacct
Tggagagtggagagttccaagtatacaaacaaagccattccgccttaacc
Gcctttcagaccgagcaaatacaagattcggagcattccgggaagatggt
tgcgaaacgccagttcagaatcggcgacatagcgGGAGAACATACCGCCT
TCAACCAACTGCCTGACGGCAAAGCCGAGTATCACGGCAAAGCATTCAGC
TCCGACGATGCTGGCGGAAAACTGACCTATACCATAGATTTCGCCAAAAA
ACAGGGACACGGCAGAATCGAACACCTGAAAACACCCGAGCAAAATGTCG
AGCTTGCCGCCGCCGAACTCAAAGCAGATGAAAAATCACACGCCGTCATT
TTGGGCGACACGCGCTACGGCAGCGAAGAAAAAGGCACTTACCACCTCGC
CCTTTTCGGCGACCGCGCCCAAGAAATCGCCGGCTCGGCAACCGTGAAGA
TAGGGGAAAAGGTTCACGAAATCGGCATCGCCGGCAAACAGTAG
```

```
vaadigagladaltapldhkdkglqsltldqsvrkneklklaaqgaekty
gngdslntgklkndkvsrfdfirqievdgqlitlesgefqvykqshsalt
afqteqiqdsehsgkmvakrqfrigdiaGEHTAFNQLPDGKAEYHGKAFS
SDDAGGKLTYTIDFAKKQGHGRIEHLKTPEQNVELAAAELKADEKSHAVI
LGDTRYGSEEKGTYHLALFGDRAQEIAGSATVKIGEKVHEIGIAGKQ*
```

Figure 26. Chimera III (NZ98254/8047) nucleotide and protein sequences

```
gtcgccgccgacatcggcgcggggcttgccgatgcactaaccgcaccgct
cgaccataaagacaaaagtttgcagtctttgacgctggatcagtccgtca
ggaaaaacgagaaactgaagctggcggcacaaggtgcggaaaaaacttat
ggaaacggcgacagccttaatacgggcaaattgaagaacgacaaggtcag
ccgtttcgactttatccgtcaaatcgaagtggacgggcagctcattacct
tggagagcggagagttccaagtgtacaaacaaagccattccgccttaacc
gcccttcagaccgagcaagaacaagatccagagcattccgggaagatggt
tgcgaaacgccggttcaaaatcggcgacatagcgGGAGAACATACCGCCT
TCAACCAACTGCCTGACGGCAAAGCCGAGTATCACGGCAAAGCATTCAGC
TCCGACGATGCTGGCGGAAAACTGACCTATACCATAGATTTCGCCGCCAA
ACAGGGACACGGCAAAATCGAACACCTGAAAACACCCGAGCAAAATGTCG
AGCTTGCCGCCGCCGAACTCAAAGCAGATGAAAAATCACACGCCGTCATT
TTGGGCGACACGCGCTACGGCAGCGAAGAAAAAGGCACTTACCACCTCGC
CCTTTTCGGCGACCGCGCCCAAGAAATCGCCGGCTCGGCAACCGTGAAGA
TAGGGGAAAAGGTTCACGAAATCGGCATCGCCGGCAAACAGTAG
```

```
vaadigagladaltapldhkdkslqsltldqsvrkneklklaaqgaekty
Gngdslntgklkndkvsrfdfirqievdgqlitlesgefqvykqshsalt
alqteqeqdpehsgkmvakrrfkigdiaGEHTAFNQLPDGKAEYHGKAFS
SDDAGGKLTYTIDFAAKQGHGKIEHLKTPEQNVELAAAELKADEKSHAVI
LGDTRYGSEEKGTYHLALFGDRAQEIAGSATVKIGEKVHEIGIAGKQ*
```

Figure 27. Chimera IV (MC58/RM1090) nucleotide and protein sequences gtcgccgccgacatcggtgcggggcttgccgatgcactaaccgcaccgct
cgaccataaagacaaaggtttgcagtctttgacgctggatcagtccgtca
ggaaaaacgagaaactgaagctggcggcacaaggtgcggaaaaacttat
ggaaacggtgacagcctcaatacgggcaaattgaagaacgacaaggtcag
ccgtttcgactttatccgccaaatcgaagtggacgggcagctcattacct
tggagagtggagagttccaagtatacaaacaaagccattccgccttaacc
gcctttcagaccgagcaaatacaagattcggagcattccgggaagatggt
tgcgaaacgccagttcagaatcggcgacatagcgGGAGAACATACCGCCT
TCAACCAACTGCCCAGCGGCAAAGCCGAGTATCACGGCAAAGCATTCAGC
TCCGACGACCCGAACGGCAGGCTGCACTACTCCATTGATTTTACCAAAAA
ACAGGGTTACGGCAGAATCGAACACCTGAAAACGCCCGAGCAGAATGTCG
AGCTTGCCTCCGCCGAACTCAAAGCAGATGAAAAATCACACGCCGTCATT
TTGGGCGACACGCGCTACGGCGGCGAAGAAAAAGGCACTTACCACCTCGC
CCTTTTCGGCGACCGCGCCCAAGAAATCGCCGGCTCGGCAACCGTGAAGA
TAAGGGAAAAGGTTCACGAAATCGGCATCGCCGGCAAACAGTAG vaadigagladaltapldhkdkglqsltldqsvrkneklklaaqgaekty
Gngdslntgklkndkvsrfdfirqievdgqlitlesgefqvykqshsalt
afqteqiqdsehsgkmvakrqfrigdiaGEHTAFNQLPSGKAEYHGKAFS
SDDPNGRLHYSIDFTKKQGYGRIEHLKTPEQNVELASAELKADEKSHAVI
LGDTRYGGEEKGTYHLALFGDRAQEIAGSATVKIREKVHEIGIAGKQ*

Figure 28. Chimera V (NZ98254/RM1090) nucleotide and protein sequences gtcgccgccgacatcggcgcggggcttgccgatgcactaaccgcaccgct
cgaccataaagacaaaagtttgcagtctttgacgctggatcagtccgtca
ggaaaaacgagaaactgaagctggcggcacaaggtgcggaaaaacttat
ggaaacggcgacagccttaatacgggcaaattgaagaacgacaaggtcag
ccgtttcgactttatccgtcaaatcgaagtggacgggcagctcattacct
tggagagcggagagttccaagtgtacaaacaaagccattccgccttaacc
gcccttcagaccgagcaagaacaagatccagagcattccgggaagatggt
tgcgaaacgccggttcaaaatcggcgacatagcgGGAGAACATACCGCCT
TCAACCAACTGCCCAGCGGCAAAGCCGAGTATCACGGCAAAGCATTCAGC
TCCGACGACCCGAACGGCAGGCTGCACTACTCCATTGATTTTACCAAAAA
ACAGGGTTACGGCAGAATCGAACACCTGAAAACGCCCGAGCAGAATGTCG
AGCTTGCCTCCGCCGAACTCAAAGCAGATGAAAAATCACACGCCGTCATT
TTGGGCGACACGCGCTACGGCGGCGAAGAAAAAGGCACTTACCACCTCGC
CCTTTTCGGCGACCGCGCCCAAGAAATCGCCGGCTCGGCAACCGTGAAGA
TAAGGGAAAAGGTTCACGAAATCGGCATCGCCGGCAAACAGTAG Vaadigagladaltapldhkdkslqsltldqsvrkneklklaaqgaekty
Gngdslntgklkndkvsrfdfirqievdgqlitlesgefqvykqshsalt
alqteqeqdpehsgkmvakrrfkigdiaGEHTAFNQLPSGKAEYHGKAFS
SDDPNGRLHYSIDFTKKQGYGRIEHLKTPEQNVELASAELKADEKSHAVI
LGDTRYGGEEKGTYHLALFGDRAQEIAGSATVKIREKVHEIGIAGKQ*

Figure 29

| (Immunogen) Antibody | Reactive Residue(s)[1] | Non-reactive strain(s) | Non-reactive residue(s) | Evidence |
|---|---|---|---|---|
| (v.1 from MC58) | | | | |
| JAR 1 | R204 | M6190 | H204 | KO |
| JAR 3 | G121 and K122 | M6190 and 03S-0408 | R121 or S122 | KO, KI |
| JAR 5 | G121 and K122 | M6190 and 03S-0408 | R121 or S122 | KO, KI |
| (v.2 from 2996) | | | | |
| JAR 10 | K180 and E192 | M1239 | R180 or D192 | KO, KI |
| JAR 11 | A174 | M1239 | K174 | KO |
| JAR 13 | S216 | RM1090 | G216 | KO, KI |
| v.3 from M1239 | | | | |
| JAR 32 | K174 | 8047 | A174 | KO, KI |
| JAR 33 | R180 and E192 | 8047 | K180 or D192 | KO, KI |
| JAR 35 | K174 | 8047 | A174 | KO, KI |
| [1]Reactive residue in fHBP from the strain used as the source for immunization. For the anti-v.2 MAbs, the reactive strain is 8047, whose fHBP is 99.6% identical to that from strain 2996.<br>[2] JAR 1, 3, 5, 13, 32 and 35 inhibited binding of fH to fHbp by ELISA and JAR 11 and 36 gave partial inhibition of binding of fH. JAR 10 and 33 did not inhibit binding of fH (See Fig. 19). | | | | |

CHIMERIC FACTOR H BINDING PROTEINS (FHBP) CONTAINING A HETEROLOGOUS B DOMAIN AND METHODS OF USE

CROSS-REFERENCE TO RELATED APPLICATIONS

This application claims priority benefit of U.S. provisional application Ser. No. 61/035,329, filed Mar. 10, 2008 and U.S. provisional application Ser. No. 61/037,252, filed Mar. 17, 2008, both of which are incorporated herein by reference in their entirety.

STATEMENT REGARDING FEDERALLY SPONSORED RESEARCH

This invention was made with government support under National Institutes of Health grant nos. R01 AI46464 and C06 RR16226. The government has certain rights in this invention.

FIELD OF THE INVENTION

This invention relates to vaccines for diseases caused by *Neisseria meningitidis*.

BACKGROUND

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane which together with the capsular polysaccharide constitute the bacterial wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse group B strains with different serotypes or serosubtypes.

Factor H Binding Protein (fHBP, also referred to in the art as lipoprotein 2086 (Fletcher et al, Infect Immun 2004; 72:2088-2100), Genome-derived Neisserial antigen (GNA) 1870 (Masignani et al. J Exp Med 2003; 197:789-99) or "741") is an *N. meningitidis* protein which is expressed in the bacterium as a surface-exposed lipoprotein. Based on sequence analysis of 71 *N. meningitidis* strains representative of its genetic and geographic diversity, *N. meningitidis* strains have been sub-divided into three fHBP variant groups (referred to as variant 1 (v.1), variant 2 (v.2), and variant 3 (v.3)) based on amino acid sequence variability and immunologic cross-reactivity (Masignani et al. J Exp Med 2003; 197:789-99). Other workers (Fletcher et al, 2004) have subdivided the protein into two sub-families designated A (which includes v.2 and v.3 of Masignani) and B (v.1). Variant 1 strains account for about 60% of disease-producing group B isolates (Masignani et al. 2003, supra). Within each variant group, there is on the order of about 92% or greater conservation of amino acid sequence. Specifically, conservation within each variant group ranges between 89 and 100%, while between the variant groups (e.g., between v.1 and v.2) the conservation can be as low as 59%. The protein is expressed by all known strains of *N. meningitidis*.

Mice immunized with recombinant fHBP developed high serum bactericidal antibody responses against strains expressing fHBP proteins of the homologous variant group (Masignani et al. 2003, supra; Welsch et al. 2004, J Immunol. 172(9):5606-15.). Thus, antiserum prepared against fHBP v.1 confers protection against *N. meningitidis* strains expressing fHBP v.1, but not against strains expressing fHBP v.2 or v.3. Similarly, antiserum prepared against fHBP v.2 protects against strains expressing v.2 (or v.3) but not v.1 (Masignani et al. J Exp Med 2003, 197:789-99; Beernink et al. J Infect Dis 2007; 195:1472-9). For vaccine purposes, it would be desirable to have a single protein capable of eliciting cross-protective antibodies against fHBP from different variant groups.

Chimeric proteins have been used for vaccine development in a variety of ways. For example, a first strategy employs a genetic or chemical linkage of an antigen to a known, but unrelated, immunogenic protein, such as the diphtheria, tetanus or pertussis toxoid proteins, or the cholera toxin B (CTB) domain, in order to enhance the magnitude of the antibody responses to the antigen of interest. A second strategy uses a genetic fusion of two antigens from the same organism, to enhance cross-protection against strains with antigenic diversity (Giuliani et al. Infect Immun 2005 73:1151-60). An example is the multivalent group B meningococcal recombinant protein vaccine, which contains a mixture of two fusion proteins: a first fusion protein of a GNA2091 protein and a GNA1870 (or "fHBP") protein, and a second fusion protein of a GNA2132 protein and a GNA1030 protein (Giuliani et al. Proc Natl Acad Sci USA 2006, 103:10834-9). A third strategy has been to construct a fusion of different serologic variants ("serovars") of one antigen to induce cross-protection against a strains with antigenic diversity. An example is a tetravalent OspC chimeric Lyme disease vaccine, which induced bactericidal antibody responses against spirochete strains expressing each of the OspC types that were incorporated into the construct (Earnhart et al. Vaccine 2007; 25:466-80).

In the examples of chimeric vaccines described that were designed to broaden protective immune responses, the vaccines were composed of repeats of an individual domain with antigenic variability. The respective variants of the domain were expressed in tandem in one protein (i.e., the same domain from different strains, $A_1$-$A_2$-$A_3$-$A_4$, etc). In some cases, these recombinant tandem proteins can be convenient for manufacturing and quality control. However they also can be very large and subject to improper folding or degradation.

One approach to avoiding the problem of large tandem fusion proteins is to design a single polypeptide that is composed of different domains of two antigenic variants e.g., by "swapping" different individual domains of an antigen, or even smaller regions such as individual epitopes from two different proteins, to form a chimeric protein that expresses antigenically unrelated epitopes specific for more than one strain (i.e., different domains from two different strains, $A_1$-$B_2$ or $A_2$-$B_1$, etc.).

This latter approach was undertaken with fHBP. First, in order to facilitate identification of bactericidal regions of fHBP, the protein was divided into three domains, designated A, B and C (Giuliani (2005) Infect. Immun. 73:1151-1160). The A domain is highly conserved across variant groups, whereas the B and C domains contain sequences that diverge among strains. Giuliani et al. identified an fHBP epitope interacting with a bactericidal mAb located in the C domain at R204 (Giuliani (2005) supra). However, a chimeric protein containing the B domain from a variant 3 strain (B₃) fused with the C domain of a variant 1 strain (C₁) failed to elicit protective bactericidal responses against strains with either v.1 or v.2 fHBP.

Vaccines that exploit the ability of fHBP to elicit bactericidal antibody responses and that can elicit such antibodies that are effective against strains expressing different fHBP variants remain of interest.

SUMMARY

Chimeric fHBPs that can elicit antibodies that are bactericidal for different fHBP variant strains of *N. meningitidis*, and methods of use, are provided.

BRIEF DESCRIPTION OF THE DRAWINGS

FIG. 4 is a schematic providing an alignment of wild-type and chimeric fHBP amino acid sequences (alignment performed using ClustalW). The deduced amino acid sequences of fHBP v.1 from strain MC58 (bottom) (SEQ ID NO:4) and v.2 strain 8047 (top) (SEQ ID NO:1) are shown, along with the two chimeric sequences (middle, Chimera I, SEQ ID NO:2, and Chimera II, SEQ ID NO:3). Numbering for all four proteins is based on the native, mature v.1 protein from MC58 (i.e., without the signal sequence). The recombinant fHBP protein as expressed in *E. coli* lacks both the signal sequence and seven presumably flexible residues (CSSGGGG, SEQ ID NO:5). An N-terminal methionine was added to each sequence shown to facilitate expression in *E. coli* (not shown). A C-terminal sequence LEHHHHHH (SEQ ID NO:6) was added to each sequence shown to facilitate isolation (not shown). The identities of the chimeras with the respective wild-type sequences are shown with symbols above and below the alignment (*=identical; :=conserved; .=semi-conserved). The position of the amino acid sequence of GEHT (SEQ ID NO:7) at residues 136-139 in the C-terminal portion of the B domain of 8047 following the junction point is indicated in a box. The outer brackets, which encompass residues 101 to 164, show the region of the protein defined as the B domain (Giuliani et al. "The region comprising amino acids 100 to 255 of *Neisseria meningitidis* lipoprotein GNA 1870 elicits bactericidal antibodies." Infect Immun 2005; 73:1151-60). With one exception, Chimera I and Chimera II have identical amino acid sequences. The exception is at residue 174 where alanine in Chimera I has been replaced by lysine in Chimera II. The position of the A174K substitution in Chimera II is shown in bold. Sequence alignment was performed with ClustalW.

FIG. 8A provides a table of strains used in the Examples, including those used to measure serum bactericidal antibody responses and description of the amino acid sequence identity compared with prototype fHBP v.1, v.2 and v.3 and JAR mAb binding of the respective fHBPs.

FIG. 8B shows the amino acid identities of different domains of fHBP. Comparisons are made for the A domain (residues 1-100), the B domain (residues 101-164) and the C domain (residues 165-255). Comparisons also are made for the B domain up to the junction point (101-135) and the B domain starting at the junction point (136-164). Numbering of amino acid residues is based on the mature protein (i.e. lacking the signal sequence) from strain MC58.

FIG. 13 is a schematic showing alignment of fHBP v.1 amino acid sequences with natural polymorphisms in the N-terminal portion of the B domain. In the alternative nomenclature based on three dimensional structural data of the entire fHbp molecule, the sequence shown also comprises a C-terminal portion of the fHbpN domain and a small N-terminal portion of the fHbpC domain as indicated above the alignment. The sequence conservation is shown below the alignment (code as in FIG. 4). The positions of c'-helices are shown above the alignment. The position of the junction point in the chimeric proteins is shown in the box. Numbering is based on the mature protein (i.e. lacking the signal sequence) from strain MC58. Strains MC58, M4105, 4243, NZ98/254 are positive for JAR3/JAR 5 reactivity; strains M6190 and 03S-0408 are negative for JAR 3/5 reactivity, and strains NM452 and CDC1573 have not been tested. The residues G121 and K122, which are associated with JAR 3 and JAR 5 mAb epitopes, are shown in bold and underlined text. Note that although strain 03S-0408 has G121, it is negative for JAR 3/5 reactivity. This strain has three amino acid differences between positions 101 and 146 compared with amino acids of MC58: L109, V114 and S122. Since both L109 and V114 are present in reactive sequences, e.g. 4243 and M4105, lack of reactivity of 03S-0408 is likely attributable to the presence of serine at position 122 instead of lysine and, therefore in addition to G121, K122 also is associated with JAR3/5 reactivity.

FIG. 14 is a schematic showing alignment of fHBP v.2 amino acid sequences with natural polymorphisms in the carboxyl-terminal portion of the B domain and the C domain, or alternatively, the complete fHbpC domain based on the three-dimensional structural nomenclature (SEQ ID NO:16-24). The sequence conservation is shown below the alignment (code as in legend to FIG. 4). The residues implicated in anti-fHBP mAb epitopes are designated with the number of the JAR mAb above the alignment: JAR 11 (alanine at residue position 174; A174); JAR 10 (lysine at residue position 180 and glutamate at position 192; K180 and E192); JAR 13 (serine residue at position 216; S216). Numbering in this figure is based on fHBP from strain MC58.

FIG. 17 provides a table summarizing cross-reactivity of the different JAR mAbs, their respective Ig isotypes and ability to inhibit binding of human fH.

FIG. 18 is a table listing human complement-mediated bactericidal activity of each of the JAR mAbs when tested individually or in combination with a second anti-fHBP mAb.

FIG. 19 is a series of graphs showing the ability of representative JAR mAbs prepared against fHBP v.2 or v.3 proteins to give concentration-dependent inhibition of binding of fH to rfHBP in an ELISA. Panel A, Inhibition of binding of fH to rfHBP v.2. Panel B, Inhibition of binding of fH to rfHBP v.3. Respective v.2 and v.3 recombinant proteins are those encoded by the fHBP genes of strains 8047 and M1239. Panel C, Inhibition of binding of fH to rfHBP v.1.

FIG. 20 is a table listing certain properties of respective pairs of JAR mAbs with or without synergistic complement-mediated bactericidal antibody, including the positions of amino acid residues involved in the epitopes, distances between them, inhibition of fH binding and isotype of each mAb.

FIG. 22 shows the amino- (N-) and carboxyl- (C-) terminal portions of the B and C domains (SEQ ID NO:29-30), which are defined with respect to the conserved amino acid sequence of GEHT (SEQ ID NO:7). The amino acid sequences that can define a JAR 3/5 epitope are positioned N-terminal to the second alpha helix; the amino acid sequence that can define the JAR 11/32/35 epitopes are positioned C-terminal to the second alpha helix. Alpha-helix (AH) 2 is indicated.

FIG. 23 is a schematic showing Chimera I (MC58/8047) nucleotide and protein sequences (SEQ ID NO:31-32). The sequence before the junction (cross-over) point is shown in lower case and the sequence following the junction point is shown in upper case. Lines of fifty residues are shown. Only the Neisserial sequences are shown; *E. coli* expression constructs contained an N-terminal Methionine and C-terminal hexa-histidine tag (LEHHHHHH, SEQ ID NO:6).

FIG. 24 is a schematic showing Chimera II (MC58/8047 A174K) nucleotide and protein sequences (SEQ ID NO:33-34). The sequence before the junction (cross-over) point is shown in lower case and the sequence following the junction point is shown in upper case. Lines of fifty residues are shown. Only the Neisserial sequences are shown; *E. coli* expression constructs contained an N-terminal Methionine and C-terminal hexa-histidine tag (LEHHHHHH, SEQ ID NO:6). The A174K substitution is shown in bold and underlined text.

FIG. 25 is a schematic showing Chimera IIb (MC58/8047 A174K/K180R) nucleotide and protein sequences (SEQ ID NO:35-36). The sequence before the junction (cross-over) point is shown in lower case and the sequence following the junction point shown in upper case. Lines of fifty residues are shown. Only the Neisserial sequences are shown; *E. coli* expression constructs contain an N-terminal Methionine and C-terminal hexa-histidine tag (LEHHHHHH, SEQ ID NO:6). The A174K and K180R substitutions are shown in bold text.

FIG. 26 is a schematic showing Chimera III (NZ98254/8047) nucleotide and protein sequences (SEQ ID NO:37-38). The sequence before the junction (cross-over) point is shown in lower case and the sequence following the junction point is shown in upper case. Lines of fifty residues are shown. Only the Neisserial sequences are shown; *E. coli* expression constructs contain an N-terminal Methionine and C-terminal hexa-histidine tag (LEHHHHHH, SEQ ID NO:6).

FIG. 27 is a schematic showing Chimera IV (MC58/RM1090) nucleotide and protein sequences (SEQ ID NO:39-40). The sequence before the junction (cross-over) point is shown in lower case and the sequence following the junction point is shown in upper case. Lines of fifty residues are shown. Only the Neisserial sequences are shown; *E. coli* expression constructs contain an N-terminal methionine and C-terminal hexa-histidine tag (LEHHHHHH, SEQ ID NO:6).

FIG. 28 is a schematic showing Chimera V (NZ98254/RM1090) nucleotide and protein sequences (SEQ ID NO:41-42). The sequence before the junction (cross-over) point is shown in lower case and the sequence following the junction point is shown in upper case. Lines of fifty residues are shown. Only the Neisserial sequences are shown; *E. coli* expression constructs contain an N-terminal methionine and C-terminal hexa-histidine tag (LEHHHHHH, SEQ ID NO:6).

FIG. 29 provides a table showing positions of residues associated with JAR mAb binding. The reactive residue in fHBP was from the strain used as the source for immunization. For the anti-v.2 mAbs, the reactive strain is 8047, whose fHBP sequence is 99.6% identical to that from strain 2996. The non-reactive residue is that present in the non-reactive strain. Loss of reactivity associated with a change from the reactive to the non-reactive residue is indicated as knock-out (KO) and the converse change is indicated as knock-in (KI).

Figure 1:
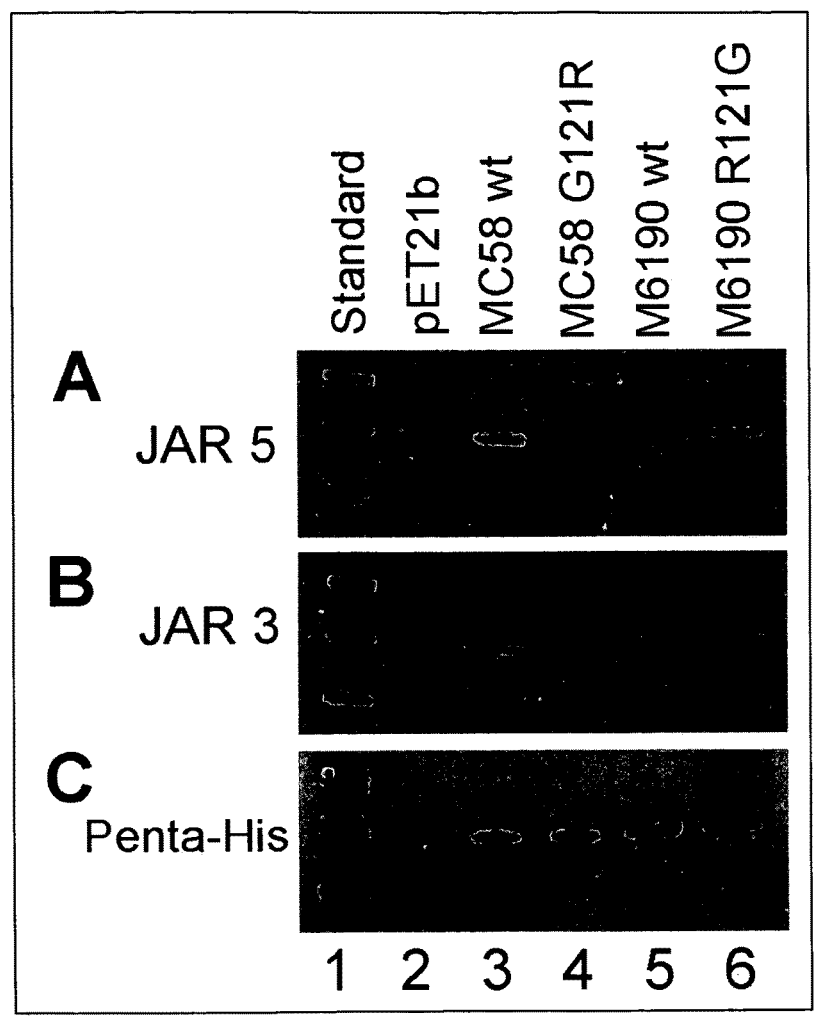
FIG. 1 is a collection of results of Western blot analysis illustrating the amino acid residues involved in binding of monoclonal antibodies (mAbs) JAR 3 and JAR 5 to factor H binding protein (fHBP). Panel A, JAR 5; lane 1, molecular mass standard; lane 2, pET21b; lane 3, pET21-fHBP(MC58 wildtype); lane 4, pET21-fHBP(MC58)G121R; lane 5, pET21-fHBP(M6190 wildtype)R121; lane 6, pET21-fHBP (M6190)R121G. Panel B, JAR 3. C, Penta-His mAb. Panels B and C have the same lane assignments as panel A.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS OF THE INVENTION

The present disclosure provides chimeric fHBPs that can elicit antibodies that are bactericidal for different fHBP variant strains of N. meningitidis*, and methods of use.

DEFINITIONS

"Factor H Binding Protein" (fHBP), which is also known in the literature as GNA1870, GNA 1870, ORF2086, LP2086 (lipoprotein 2086), and "741" refers to a polypeptide of *N. meningitidis* that is a lipoprotein presented on the surface of the bacterium. *N. meningitidis* strains have been sub-divided into three fHBP variant groups (referred to as variant 1 (v.1), variant 2 (v.2), and variant 3 (v.3) in some reports (Masignani et al. 2003, supra) and Family A and B in other reports (see, e.g., Fletcher et al. 2004 Infect Immun 2088-2100)) based on amino acid sequence variability and immunologic cross-reactivity (Masignani et al. J Exp Med 2003; 197:789-99). For clarity, the present disclosure uses the v.1, v.2 and v.3 terminology. Because the length of variant 2 (v.2) fHBP protein (from strain 8047) and variant 3 (v.3) fHBP (from strain M1239) differ by −1 and +7 amino acid residues, respectively, from that of MC58, the numbering used to refer to residues for v.2 and v.3 fHBP proteins differs from numbering based on the actual amino acid sequences of these proteins. Thus, for example, reference to a leucine residue (L) at position 166 of the v.2 or v.3 fHBP sequence in FIG. 3 refers to the residue at position 165 of the v.2 protein and at position 173 in the v.3 protein. For further clarification, see FIG. 4 for alignment.

The term "heterologous" refers to two components that are defined by structures derived from different sources. For example, where "heterologous" is used in the context of a chimeric polypeptide, the chimeric polypeptide includes operably linked amino acid sequences that can be derived from different polypeptides (e.g., a first component from a fHBP v.1 polypeptide and a second component from a fHBP v.2 polypeptide). Similarly, "heterologous" in the context of a polynucleotide encoding a chimeric polypeptide includes operably linked nucleic acid sequence that can be derived from different genes (e.g., a first component from a nucleic acid encoding a fHBP v.1 polypeptide and a second component from a nucleic acid encoding a fHBP v.2 polypeptide). Such chimeric polypeptides as described herein provide for presentation of epitopes in a single polypeptide that are normally found in different polypeptides. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding a fHBP polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

"Heterologous" as used herein in the context of a chimeric fHBP (e.g., "heterologous fHBP domain", e.g., a "heterologous B domain", "heterologous C domain") indicates that the chimeric fHBP protein contains operably linked and contiguous amino acid sequences of structural elements of at least two different fHBP variants (e.g., so as to provide for presentation of epitopes of a v.1 fHBP, and presentation of a v.2 fHBP and/or a v.3 fHBP in a single fHBP polypeptide). For example, a "heterologous B domain" refers to a polypeptide which comprises a B domain that contains a first portion having a contiguous amino acid sequence of a B domain of a first fHBP variant operably linked to a second portion having a contiguous amino acid sequence of a B domain of a second fHBP variant.

"Derived from" in the context of an amino acid sequence or polynucleotide sequence (e.g., an amino acid sequence "derived from" a v.1 fHBP) is meant to indicate that the polypeptide or nucleic acid has a sequence that is based on that of a reference polypeptide or nucleic acid (e.g., a naturally occurring fHBP protein or encoding nucleic acid), and is not meant to be limiting as to the source or method in which the protein or nucleic acid is made. "Derived from" in the context of bacterial strains is meant to indicate that a strain was obtained through passage in vivo, or in in vitro culture, of a parental strain and/or is a recombinant cell obtained by modification of a parental strain.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Conservative amino acid substitutions in the context of a chimeric fHBP disclosed herein are selected so as to preserve presentation of an epitope of interest. Guidance for such substitutions can be drawn from alignments of amino acid sequences of polypeptides presenting the epitope of interest.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans. (Goldschneider et al., 1969, J. Exp. Med. 129:1307; Borrow et al. 2001 Infect Immun. 69:1568).

The phrase "a disease caused by a strain of capsular group B of *Neisseria meningitidis*" encompasses any clinical symptom or combination of clinical symptoms that are present in an infection of a human with a member of capsular group B of *Neisseria meningitidis*. These symptoms include but are not limited to: colonization of the upper respiratory tract (e.g. mucosa of the nasopharynx and tonsils) by a pathogenic strain of capsular group B of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least more than one strain (and can be against at least two, at least three, at least four, at least five, against at least eight, or more strains) of *Neisseria meningitidis*, wherein each of the strains expresses a different fHBP subvariant or fHBP variant. The present disclosure specifically contemplates and encompasses a vaccine or vaccination regimen that confers protection against a disease caused by a member of any capsular group (e.g., A, B, or C), with protection against disease caused by a capsular group B strain of *Neisseria meningitidis* being of interest due to the epidemiological prevalence of strains causing disease with this capsular group and lack of broadly effective group B vaccines.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and do not bind in a significant amount to other epitopes present in the antigen and/or in the sample.

The phrase "in a sufficient amount to elicit an immune response" means that there is a detectable difference between an immune response indicator measured before and after administration of a particular antigen preparation Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of *Neisseria meningitidis* (e.g. the outer membrane, inner membrane, periplasmic space, capsule, pili, etc.).

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified."

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, chimeric polypeptide, and the like)

A "knock-out" or "knockout" of a target gene refers to an alteration in the sequence of the gene that results in a decrease of function of the target gene, e.g., such that target gene expression is undetectable or insignificant, and/or the gene product is not functional or not significantly functional. For example, a "knockout" of a gene involved in LPS synthesis indicates means that function of the gene has been substantially decreased so that the expression of the gene is not detectable or only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like. A "knock-in" or "knockin" of a target gene refers to a genetic alteration in a host cell genome that that results in an increase in a function provided by the target gene, fHBP and fHBP-Encoding Nucleic Acids Before describing further exemplary chimeric fHBPs contemplated by the present disclosure, it is helpful to describe naturally-occurring fHBP from which the chimeric fHBPs may be derived.

For convenience and clarity, the native amino acid sequence of the v.1 fHBP of the *N. meningitidis* strain MC58 was arbitrarily selected as a reference sequence for all native v.1, v.2, and v.3 fHBP amino acid sequences, as well as for the chimeric fHBPs described herein. Two nomenclature systems have been adopted to describe fHBP: one, which for convenience divided the protein into three domains, designated A, B and C (Giuliani et al., Infect Immun 2005; 73:1151-60), and the other based on three-dimensional structural data. In the alternative nomenclature system that describes fHBP based on three-dimensional structural data, fHBP is divided into two domains: the fHbpN and the fHbpC. Details of each of these domains with reference to the amino acid sequence of v.1 fHBP of MC58 strain is described below.

A, B, and C Domains Using First Definition.

Figure 21:
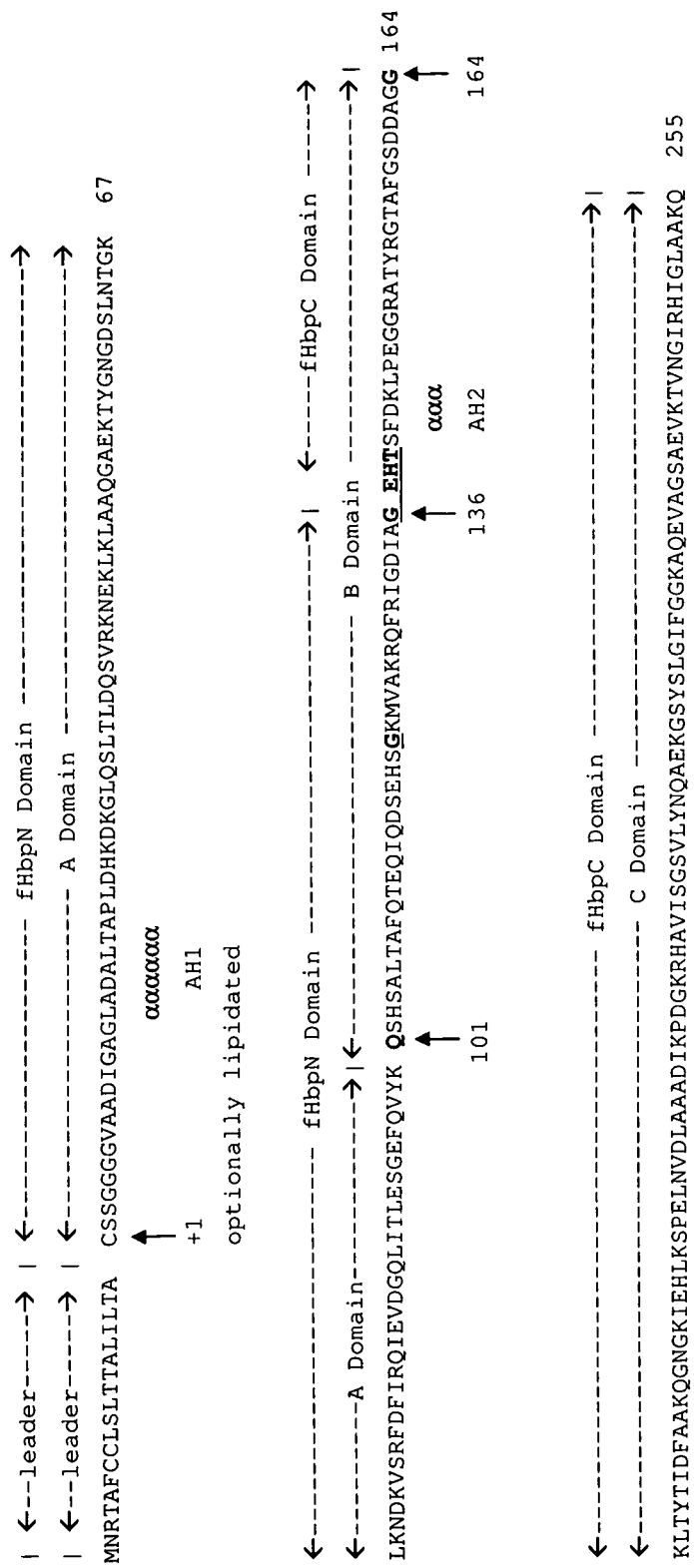
FIG. 21 provides the amino acid sequence of variant 1 (v.1) factor H binding protein (fHBP) of MC58, with the A, B and C domains indicated (SEQ ID NO:28). Positions of the structural domains, fHbpN and fHbpC, are also shown. Glutamine 101 (Q) and glycine 164 (G) indicated by upward arrows define the A/B and B/C domain borders, respectively, as defined by Giuliani et al., Infect. Immun, 2005 73:1151-60. The upward arrow at glycine 136 designates the boundary between the fHbpN and the fHbpC domains, as defined by Cantini et al., J. Biol. Chem. 2009.
Figure 34:
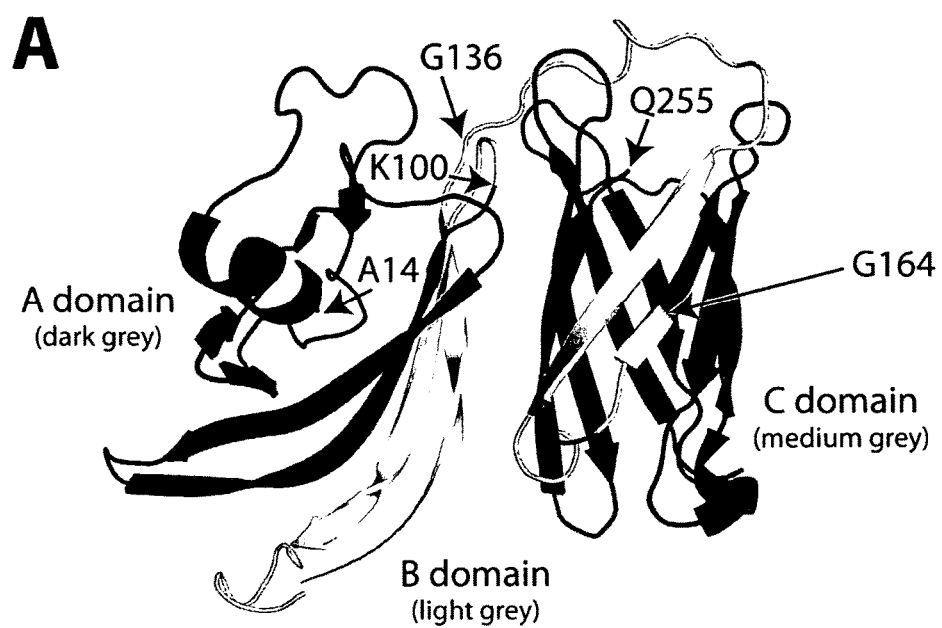
FIG. 34 shows ribbon diagrams of full length v.1 fHBPs. Panel A, fHBP is partitioned into three domains indicated by various shades of gray. The A domain and the N-terminal portion of the B domain are on the left and the boundary between the A and B domains is indicated by an arrow at lysine 100. The C-terminal portion of the B domain together with the C domain is on the right, where the boundary between the two is designated by an arrow at glycine 164. Panel B, an alternative nomenclature describes the fHBP as having two structural domains. The N-terminal domain containing a mix of α helices and β strands is named the fHbpN domain (left) and the C-terminal domain consisting of β strands is labeled as the fHbpC domain (right). The fHbpN and the fHbpC are connected by a linker at or proximal to glycine 136. In some embodiments, the junction point relevant for the chimeric fHBP described herein is at or proximal to G136, indicated by an arrow in both panels. The models shown in both panels are constructed based on the NMR structure of Cantini et al. J Biol Chem 2009.

As noted above, the nomenclature based on three domains describes fHBP as having an "A domain", a "B domain", and a "C domain". The amino acid sequence of the v.1 fHBP of the MC58 strain along with the boundaries of the A, B and C domains is shown in FIG. 21. The Q101 and G164 residues indicated by the upward arrows denote the A/B and B/C domain boundaries, respectively. The "α" symbols indicate the position of the first and second α helices of the fHBP (referred to as AH1 and AH2). Residues GEHT (SEQ ID NO:7) are underlined followed by the second α helix (AH2) of fHBP. Panel A in FIG. 34 also shows a ribbon diagram of the full length fHBP with the A, B, and C domains indicated as various shades of gray.

Figure 3:
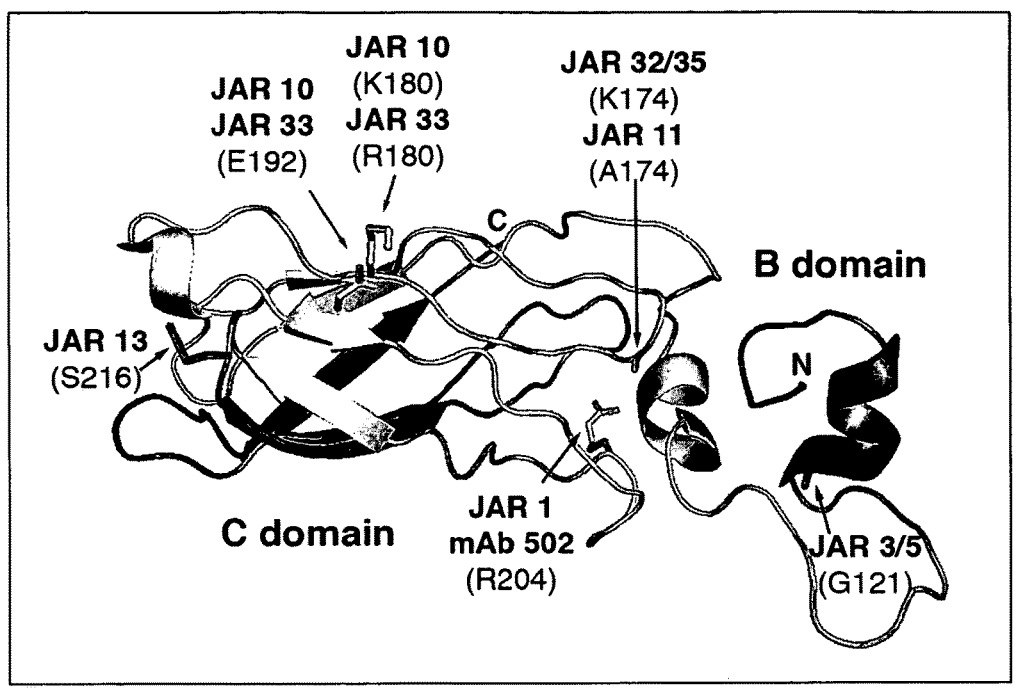
FIG. 3 is a schematic illustrating positions of residues associated with the epitopes of the nine anti-fHBP mAbs ("JAR" mAbs) in the structural model based on previously reported NMR data (Cantini et al. "Solution structure of the immunodominant domain of protective antigen GNA1870 of *Neisseria meningitidis*." J Biol Chem 2006; 281:7220-7). Coordinates from the solution structure of the B and C domains of fHBP v.1 from strain MC58 were used to construct the model. Note that the positions of amino acid residues involved in the epitopes for antibodies raised against the fHBP v.2 and v.3 proteins are shown on the model, even though these antibodies do not bind to the v.1 protein from strain MC58. It should also be noted that numbering of amino residues is based on the mature protein sequence of fHBP (i.e. lacking the signal sequence) from strain MC58. Because the amino acid sequences of the variant 2 (v.2) fHBP protein (from strain 8047) and variant 3 (v.3) fHBP (from strain M1239) differ by −1 and +7 amino acid residues, respectively, from that of MC58, the numbering used to refer to residues for v.2 and v.3 fHBP proteins differs from numbering based on the actual amino acid sequences of these proteins. Thus, for example, reference to a leucine residue (L) at position 166 of the v.2 or v.3 fHBP sequence in FIG. 3, refers to the residue at position 165 of the v.2 protein and at position 173 in the v.3 protein. For further clarification, see FIG. 4 for alignment. Details of the reactive and non-reactive residues are provided herein. The residue shown for mAb 502 is from a previously reported study (Giuliani et al., 2005 Infect Immun 73:1151-60). The numbering is based on amino acid sequence of MC58 v.1 fHBP lacking the signal sequence (Masignani et al., 2003 J Exp Med 197:789-99).

FIG. 3 provides a schematic of a truncated structural model of fHBP having operably linked B and C domains (the A domain and a portion of the N-terminal portion of the B domain are not shown). The native v.1 fHBP of MC58 was again used as a reference sequence for purposes of residue numbering Amino acid residues identified by site-directed mutagenesis of fHBP that contribute to binding of nine anti-fHBP mAbs (referred to as "JAR" mAbs) are noted. Coordinates from the solution structure of the B and C domains of fHBP from strain MC58 were used to construct the model. The α helix of the B domain is illustrated, as are the loops and β strands of the C domain.

Three-Dimensional Structural Domains/fHbpN and fHbpC

In an alternative nomenclature system, fHBP is described as having two structural domains as opposed to the three domains described above. The two-domain nomenclature system is based on structural information of a full-length fHBP from which three-dimensional models may be constructed, such as the ones shown in FIG. 34. Structural modeling reveals that full-length fHBP is found to exist in solution as two separate domains connected by a linker. The amino acid sequence of the v.1 fHBP of the MC58 strain is shown in FIG. 21 with end of the fHbpN domain indicated with an arrow at glycine 136. The N-terminal domain is named fHbpN (residues 8-136) and the C-terminal domain fHbpC (residues 141-255), each comprising at least 8 anti-parallel β strands and joined by a native linker (residues 137-140). As seen in FIG. 21, the linker also comprises α-helix AH2 as "α" below the sequence in FIG. 21 marks the positions of α helices that reside in fHBP. For purposes of simplification herein, the fHbpC domain is considered to include the linker that connects the N-terminal and C-terminal domains based on the convention of this nomenclature.

fHBP has been divided into three variant groups (referred to as variant 1 (v.1), variant 2 (v.2), and variant 3 (v.3)) based on amino acid sequence variability and immunologic cross-reactivity (Masignani et al. 2003 J Exp Med 197:789-99). In certain studies, fHBP has also been subdivided into two sub-families designated sub-family A (which includes v.2 and v.3 of Masignani et al., 2003 J Exp Med 197:789-99) and sub-family B (v.1) (Fletcher et al., 2004, *Infect Immun.* 72: 2088-100). "Variant" as used in the context of an "fHBP variant" refers to an fHBP that share at least 89% amino acid sequence identity with the prototype strain of that variant group (strain MC58 for v.1; strain 2996 for v.2; and strain M1239 for v.3). These were the original prototype sequences described by Masignani et al., J. Exp. Med., 2003. Strains within a variant group encode fHBPs with greater than 88% amino acid identity, whereas strains of different fHBP variant groups range from approximately 60-88% identical. fHBPs in the same "variant" group possess greater than 88% identity to the respective prototype sequence (v.1, strain MC58; v.2, strain 2996; v.3, strain M1239). A "subvariant" as used in the context of an "fHBP subvariant" refers to fHBP polypeptides that differ from the prototype sequence. For example, strain NZ98/254 is referred to as an fHBP v.1 subvariant, with 91% identity to the prototype sequence from strain MC58; strain RM1090 is referred to as an fHBP v.2 subvariant, with a sequence that is 94% identical to the v.2 prototype strain 2996. Examples of subvariants, and their relative amino acid sequence identities, are provided in FIGS. 8A and 8B.

fHBP polypeptides, and encoding nucleic acids, from which portions of the chimeric fHBPs of the present disclosure can be derived may be from any suitable *N. meningitidis* strain. As is known in the art, *N. meningitidis* strains are divided into serologic groups (capsular groups), serotypes (PorB phenotypes) and subtypes (PorA phenotypes) on the basis of reactions with polyclonal (Frasch, C. E. and Chapman, 1973, *J. Infect. Dis.* 127: 149-154) or monoclonal antibodies that interact with different surface antigens. Capsular grouping traditionally has been based on immunologically detectable variations in the capsular polysaccharide but is being replaced by PCR of genes encoding specific enzymes responsible for the biosynthesis of the structurally different capsular polysaccharides. About 12 capsular groups (including A, B, C, X, Y, Z, 29-E, and W-135) are known. Strains of the capsular groups A, B, C, Y and W-135 account for nearly all meningococcal disease. Serotyping traditionally has been based on monoclonal antibody defined antigenic differences in an outer membrane protein called Porin B (PorB). Antibodies defining about 21 serotypes are currently known (Sacchi et al., 1998, *Clin. Diag. Lab. Immunol.* 5:348). Serosubtyping has been based on antibody defined antigenic variations on an outer membrane protein called Porin A (PorA). Both serotyping and serosubtyping are being replaced by PCR and/or DNA sequencing for identification of genes encoding the variable regions of PorB and PorA, respectively that are associated with mAb reactivity (e.g. Sacchi, Lemos et al., supra; Urwin et al., 1998, *Epidem. and Infect.* 120:257).

N. meningitidis also may be divided into clonal groups or subgroups, using various techniques that directly or indirectly characterize the bacterial genome. These techniques include multilocus enzyme electrophoresis (MLEE), based on electrophoretic mobility variation of an enzyme, which reflects the underlying polymorphisms at a particular genetic locus. By characterizing the variants of a number of such proteins, genetic "distance" between two strains can be inferred from the proportion of mismatches. Similarly, clonality between two isolates can be inferred if the two have identical patterns of electrophoretic variants at number of loci. In more recent literature, multilocus sequence typing (MLST) has superseded MLEE as the method of choice for characterizing the microorganisms. Using MLST, the genetic distance between two isolates, or clonality, is inferred from the proportion of mismatches in the DNA sequences of seven housekeeping genes in Neisseria meningitidis strains (Maiden et al., 1998, Proc. Natl. Acad. Sci. USA 95:3140).

While N. meningitidis strains of any capsular group may be used, N. meningitidis strains of capsular group B are of particular interest as sources from which nucleic acid encoding fHBP and domains thereof are derived.

While the specification provides the amino acid sequence of exemplary fHBPs from which the chimeric fHBP can be derived, this is not intended to be limiting. For example, the chimeric fHBP can contain amino acid sequences that are at least 80%, at least 85%, at least 90%, or at least 95% identical to an amino acid sequence of a naturally-occurring fHBP.

Nucleic acids encoding fHBP polypeptides for use in construction of chimeric fHBPs contemplated herein are known in the art. Exemplary fHBP polypeptides are described in, for example, WO 2004/048404; Masignani et al. 2003 J Exp Med 197:789-799; Fletcher et al. Infect Immun 2004 2088-2100; Welsch et al. J Immunol 2004 172:5606-5615; and WO 99/57280. Nucleic acid (and amino acid sequences) for fHBP variants and subvariants are also provided in GenBank as accession nos.: NC_003112, GeneID: 904318 (NCBI Ref. NP_274866) (from *N. meningitidis* strain MC58); AY548371 (AAT01290.1) (from *N. meningitidis* strain CU385); AY548370 (AAT01289.1) (from *N. meningitidis* strain H44/76); AY548377 (AAS56920.1) (from *N. meningitidis* strain M4105); AY548376 (AAS56919.1) (from *N. meningitidis* strain M1390); AY548375 (AAS56918.1) (from *N. meningitidis* strain N98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83).

For purposes of identifying relevant amino acid sequences contemplated for use in the chimeric fHBPs disclosed herein, it should be noted that the immature fHBP protein includes a leader sequence of about 19 residues. Furthermore, when provided an amino acid sequence the ordinarily skilled person can readily envision the sequences of nucleic that can encode for, and provide for expression of, a polypeptide having such an amino acid sequence.

In addition to the specific amino acid sequences and nucleic acid sequences provided herein, the disclosure also contemplates polypeptides and nucleic acids having sequences that are at least 80%, at least 85%, at least 90%, or at least 95% identical in sequence to such exemplary amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region, e.g., a B domain or portion thereof, e.g., a region at least about 30, 35, 40, 45, 50, 55, 60, 65 or more amino acids or nucleotides in length, and can be up to the full-length of the reference amino acid or nucleotide sequence (e.g., a full-length fHBP). The disclosure specifically contemplates both naturally-occurring polymorphisms and synthetically produced amino acid sequences and their encoding nucleic acids.

For sequence comparison, typically one sequence acts as a reference sequence (e.g., a naturally-occurring fHBP polypeptide sequence), to which test sequences are compared. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (www.ncbi.nlm nih gov). Further exemplary algorithms include ClustalW (Higgins D., et al. (1994) Nucleic Acids Res 22: 4673-4680), available at www.ebi.ac.uk/Tools/clustalw/index.html.

In one embodiment, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

The chimeric fHBP of the present disclosure is described in more detail below in the context of both the nomenclature dividing the protein into three domains used by Giuliani et al. (Infect Immun 2005; 73:1151-60) and the three-dimensional structural nomenclature.

A Domain of fHBPs

As noted above, fHBP may be described as having the following three domains to facilitate analysis: A domain, B domain, and C domain. As shown in FIG. 21, the upward arrows at Q101 and G164 demarcate the boundaries between A/B domains and B/C domains, respectively. The chimeric fHBPs of the present disclosure optionally include an A domain. For convenience and clarity, the A domain can be structurally defined as those residues corresponding to residues 1-100 of v.1 fHBP of MC58, where the numbering is based on amino acid sequence of MC58 v.1 fHBP lacking the signal sequence (Masignani et al., 2003 J Exp Med 197:789-99) (see FIG. 21). As exemplified in the alignment of v.1 fHBP of MC58 and v.2 fHBP of 8047, the respective amino acid sequences of the A domains of fHBPs normally share significant amino acid sequence identity (see FIG. 8B) Chimeric fHBPs which contain an A domain can contain a contiguous A domain amino acid sequence that is at least 85%, at least 90%, or at least 95% identical to an amino acid sequence of an A domain of a naturally occurring fHBP. The A domain may be derived from the same variant group (and may be derived from the same fHBP) as the N-terminal portion of the B domain, such that the amino acid sequence at the A/B junction is one that may be found in nature. Alternatively, the A domain amino acid sequence may be derived from a fHBP variant group different from the fHBP variant group from which the N-terminal amino acid sequence of the B domain is derived (e.g., the A domain may be derived from a v.2 fHBP and the N-terminal amino acid sequence of the B domain derived from a v.1 fHBP).

B Domain of v.1 fHBP

As noted above, the chimeric fHBPs of the present disclosure contain amino acid sequence of a v.1 fHBP B domain. Amino acid sequences of v.1 fHBP, including v.1 fHBP B domains, are well known in the art and can be used to derive the desired amino acid sequence of a chimeric fHBP disclosed herein. FIG. 13 provides the amino acid sequences of an N-terminal portion of the B domain of selected v.1 fHBPs. The alignment illustrates the position and identity of naturally occurring polymorphisms among v.1 fHBPs. FIG. 8A illustrates the amino acid sequence identity between full length fHBPs of exemplary v.1, v.2 and v.3 strains, and further illustrates the presence or absence of epitopes defined by the indicated JAR mAbs. FIG. 8B illustrates the amino acid sequence identity between the A, B, and C domains of exemplary v.1, v.2 and v.3 fHBPs, as well as amino acid sequence identity within the N-terminal (101-135) and C-terminal (136-164) portions of B domains.

FIG. 21 shows the amino acid sequence of the fHBP of the v.1 strain MC58, and illustrates the position and of a full-length B domain (defined by residues 101-164 and encompassing the amino acid sequence of GEHT (SEQ ID NO:7) followed by α-helix AH2). FIG. 22, Panel A illustrates that an N-terminal portion of the B domain of the v.1 fHBP of the MC58 strain, can encompass an amino acid sequence defined by residues corresponding to residues N-terminal of the GEHT (SEQ ID NO:7) residues and extending to the N-terminus of the B domain at a residue corresponding to residue 101. The C-terminal portion of the B domain of the v.1 fHBP of the MC58 strain can encompass an amino acid sequence defined by those residues corresponding to an amino acid sequence extending N-terminally from residue 164 of the B domain, and encompassing up to and including the amino acid sequence of GEHT (SEQ ID NO:7). Thus, a full-length B domain is structurally defined by the residues corresponding to residues 101-164 of the v.1 of fHBP of MC58, where residues 101-135 can define an exemplary N-terminal portion of the B domain and residues 136-164 can define an exemplary C-terminal portion of the B domain, where the numbering is based on amino acid sequence of MC58 v.1 fHBP lacking the signal sequence (Masignani et al., 2003 J Exp Med 197:789-99).

As will be described below in more detail, it should be noted that in the context of chimeric fHBPs of the present disclosure having a heterologous B domain, the C-terminus of the N-terminal portion of the B domain (and thus the N-terminus of the C-terminal portion of the heterologous B domain) is defined by the position of the junction point, which can be present N-terminal or C-terminal to the amino acid sequence of GEHT (SEQ ID NO:7), as discussed below in more detail. For example, the junction point of a heterologous B domain of a chimeric fHBP can be positioned C-terminal to a sequence corresponding to the GEHT (SEQ ID NO:7), and thus can extend beyond a residue corresponding to residue 135.

Exemplary chimeric fHBP include those comprising a B domain having a contiguous amino acid sequence that is at least 80%, at least 85%, at least 90%, or at least 95% identical to an N-terminal B domain amino acid sequence of a v.1 fHBP, e.g., at least 80%, at least 85%, at least 90%, or at least 95% identical to a contiguous amino acid sequence of the N-terminal B domain amino acid sequence exemplified in FIG. 13. Exemplary chimeric fHBP having a heterologous B domain contain at least 35, at least 40, at least 45, at least 50 residues (and in some embodiments no more than 50 residues) of a contiguous N-terminal amino acid sequence of a B domain of a v.1 fHBP.

B and C Domains of v.2 fHBP and of v.3 fHBP

Exemplary chimeric fHBPs of the present disclosure contain a heterologous B domain containing an N-terminal amino acid sequence derived from an N-terminal portion of a v.1 fHBP B domain and the remaining C-terminal portion derived from the corresponding C-terminal portion of a v.2 (or v.3) fHBP B domain, followed by the contiguous amino acid sequence of a v.2 (or v.3) C domain. For convenience and clarity, the C domain can be structurally defined as those residues corresponding to residues 165-255 of v.1 fHBP of MC58, where the numbering is based on amino acid sequence of MC58 v.1 fHBP lacking the signal sequence (Masignani et al., 2003 J Exp Med 197:789-99) (see FIG. 21).

Amino acid sequences of v.2 and v.3 fHBP, including v.2 and v.3 fHBP B and C domains, are well known in the art and can be used to derive the desired amino acid sequence of a chimeric fHBP disclosed herein. FIG. 14 provides the amino acid sequences of a C-terminal portion of the B domain (as exemplified by the C-terminal 25 amino acids of v.2 fHBP B domain) and the full-length C domains of selected v.2 fHBPs. The alignment illustrates the position and identity of naturally occurring polymorphisms among v.2 fHBPs.

Exemplary chimeric fHBP include those comprising a B domain containing a C-terminal amino acid sequence derived from a v.2 or v.3 B domain, usually having a contiguous amino acid sequence that is greater than or at least 85%, at least 90%, or at least 95% identical to an C-terminal B domain amino acid sequence of a v.2 or v.3 fHBP, e.g., at least 80%, at least 85%, at least 90%, or at least 95% identical to a contiguous amino acid sequence of the N-terminal B domain amino acid sequence, such as those v.2 sequences exemplified in FIG. 14. Where the chimeric fHBP contains a heterologous C domain, the B domain can be at least 80%, at least 85%, at least 90%, or at least 95% identical to a contiguous amino acid sequence of a full-length B domain amino acid sequence of a v.1 fHBP. A full-length B domain of a v.1 fHBP generally is about 64 residues in length.

fHbpN Domain of fHBPs

As discussed previously, fHBP may also be described has having two structural domains: fHbpN and fHbpC, based on an alternative nomenclature that is derived from the structure of the full-length fHBP. As shown in FIG. 21 and panel B of FIG. 32, glycine 136 marks approximately the beginning of a linker between the N-terminal and the C-terminal domains, named the fHbpN and fHbpC domains, respectively. The chimeric fHBP of the present disclosure may include a full-length fHbpN domain or a partial fHbpN domain. For convenience and clarity, the fHbpN domain can be structurally defined as those residues corresponding to residues 1-136 of v.1 fHBP of MC58, where the numbering is based on amino acid sequence of MC58 v.1 fHBP lacking the signal sequence (Masignani et al., 2003 J Exp Med 197:789-99) (see FIG. 21). As exemplified in the alignment of v.1 fHBP of MC58 and v.2 fHBP of 8047, the respective amino acid sequences of the first 100 residues of the fHbpN domain normally share significant amino acid sequence identity (FIG. 8B) Chimeric fHBP which contains an fHbpN domain can contain a contiguous fHbpN domain amino acid sequence that is at least 85%, at least 90%, or at least 95% identical to an amino acid sequence of an fHbpN domain of a naturally occurring fHBP.

Alternatively, the chimeric fHBP may include a partial fHbpN domain, such that an N-terminal portion of the fHbpN is truncated. The partial fHbpN domain may comprise at least 30, 40, or 50 of a contiguous C-terminal amino acid sequence of the full length fHbpN domain.

Exemplary chimeric fHBPs include those comprising a full or partial fHbpN domain having a contiguous amino acid sequence that is at least 80%, at least 85%, at least 90%, or at least 95% identical to at least a C-terminal portion of the fHbpN amino acid sequence of a v.1 fHBP, e.g., at least 80%, at least 85%, at least 90%, or at least 95% identical to a contiguous amino acid sequence of the C-terminal fHbpN amino acid sequence exemplified in FIG. 13. An exemplary chimeric fHBP having heterologous domains contains at least 35, at least 40, at least 45, at least 50 residues (and in some embodiments no more than 50 residues) of a contiguous C-terminal amino acid sequence of an fHbpN domain of a v.1 fHBP.

The full or partial fHbpN domain may be derived from the same variant group (and may be derived from the same fHBP) as certain portions of the fHbpC domain. Alternatively, the fHbpN amino acid sequence may be derived from a fHBP variant group different from the fHBP variant group from which the N-terminal amino acid sequence of the fHbpC domain is derived (e.g., the fHbpC domain may be derived from a v.2 fHBP and the C-terminal amino acid sequence of the fHbpN domain derived from a v.1 fHBP).

As noted above, the chimeric fHBPs of the present disclosure contain amino acid sequence of a v.1 fHbpN domain. Amino acid sequences of v.1 fHBP, including v.1 fHbpN domains, are well known in the art and can be used to derive the desired amino acid sequence of a chimeric fHBP disclosed herein. FIG. 13 provides the C-terminal amino acid sequences of the fHbpN domain of selected v.1 fHBPs. The alignment illustrates the position and identity of naturally occurring polymorphisms among v.1 fHBPs. FIG. 8A illustrates the amino acid sequence identity between full length fHBPs of exemplary v.1, v.2 and v.3 strains, and further illustrates the presence or absence of epitopes defined by the indicated JAR mAbs. FIG. 8B illustrates the amino acid sequence identity between exemplary v.1, v.2 and v.3 fHBPs, as well as amino acid sequence identity within the C-terminal portion of the fHbpN (101-135) and N-terminal (136-164) portion of the fHbpC domains.

The Junction Between Heterologous Domains of a Chimeric fHBP

As will be described below in more detail, it should be noted that in the context of chimeric fHBPs of the present disclosure having heterologous domains, the position of the junction point between heterologous domains can be present within or proximal to the linker that connects the fHbpN and the fHbpC domains. Glycine 136 defines the boundary between fHbpN and fHbpC and also marks the beginning of the linker sequence. The linker sequence corresponds approximately to residues 136 to 149 and includes α-helix AH2. For example, the junction point between heterologous domains of a chimeric fHBP can be positioned C-terminal to a sequence corresponding to the GEHT (SEQ ID NO:7) sequence underlined in FIG. 21. In some embodiments, the junction may be no more than 20, no more than 15, no more than 5 or less amino acid residues away from the amino acid sequence of GEHT (SEQ ID NO:7) or the linker sequence. In other embodiments where heterologous domains are present in the fHbp C domain, the junction between the heterologous domains may be positioned C-terminal to glycine 164. Glycine 164 is also indicated by an arrow in FIG. 21.

fHbpC Domain of v.2 fHBP and of v.3 fHBP

Exemplary chimeric fHBPs of the present disclosure contain heterologous domains comprising a full or partial fHbpN domain of a v.1 fHBP fHbpN domain and a fHbpC domain derived from the fHbpC of a v.2 (or v.3) fHBP. For convenience and clarity, the fHbpC domain can be structurally defined as those residues corresponding to residues 141-255 of v.1 fHBP of MC58, where the numbering is based on amino acid sequence of MC58 v.1 fHBP lacking the signal sequence (Masignani et al., 2003 J Exp Med 197:789-99) (FIG. 21).

Amino acid sequences of v.2 and v.3 fHBP, including v.2 and v.3 fHBP fHbpN and fHbpC domains, are well known in the art and can be used to derive the desired amino acid sequence of a chimeric fHBP disclosed herein. FIG. 14 provides the amino acid sequences of the full-length fHbpC domains of selected v.2 fHBPs. The alignment illustrates the position and identity of naturally occurring polymorphisms among v.2 fHBPs. Exemplary chimeric fHBPs include those comprising an fHbpC amino acid sequence derived from a v.2 or v.3 fHbpC domain, usually having a contiguous amino acid sequence that is greater than or at least 85%, at least 90%, or at least 95% identical to the amino acid sequence of the fHbpC domain of a v.2 or v.3 fHBP, e.g., at least 80%, at least 85%, at least 90%, or at least 95% identical to a contiguous amino acid sequence of the fHbpC domain amino acid sequence, such as those v.2 sequences exemplified in FIG. 14.

In certain cases, instead of having the amino acid sequence of fHbpN derived from one variant and that of fHbpC derived from a different variant, fHbpC domain may contain two contiguous amino acid sequences derived from different variants. In cases where fHbpC contains heterologous sequences, a contiguous N-terminal amino acid sequence of fHbpC can be at least 80%, at least 85%, at least 90%, or at least 95% identical to a contiguous amino acid sequence of the corresponding amino acid sequence of a v.1 fHBP.

Chimeric Factor H Binding Proteins

As explained previously, fHBP may be described in the context of the three domains assigned by Giuliani et al (Infect Immun 2005; 73:1151-60) or in the context of two three-dimensional structural domains. For the sake of brevity, the disclosure will adopt the nomenclature of the three domains, designated A, B, and C domains. However, all discussion in the context of the three functional domains can be readily understood in the context of the two structural domains based on what has been detailed above.

As set out above, the chimeric fHBPs of the present disclosure generally include either a heterologous B domain and a C domain; or a B domain and a heterologous C domain. Such chimeric fHBPs are constructed so as to contain epitopes that elicit bactericidal antibodies effective against *N. meningitidis* strains producing more than one fHBP variant.

The term "chimeric factor H binding protein" or "chimeric fHBP" refers to a polypeptide comprising, from N-terminus to C-terminus, an amino acid sequence of a B domain and of a C domain, wherein at least one of the B domain and the C domain contains a heterologous amino acid sequence characterized as having an N-terminal portion derived from a contiguous amino acid sequence of a v.1 fHBP with the remaining B and C-terminal portion (or C terminal portion) being derived from a contiguous amino acid sequence of a v.2 or v.3 fHBP. The B domain and/or C domain amino acid sequences are generally derived from a contiguous amino acid sequence of a naturally-occurring fHBP and mutants thereof that maintain or introduce desired epitopes Chimeric fHBP can optionally include an amino acid sequence of an fHBP A domain operably linked and N-terminal to the B domain Chimeric fHBP can further optionally include a leader sequence, e.g., to provide for expression of the chimeric fHBP on a cell surface of a bacterial host cell.

Where the chimeric fHBP contains a heterologous B domain, the heterologous B domain generally comprises at least an N-terminal portion derived from a contiguous amino acid sequence of a v.1 fHBP B domain and a C-terminal portion derived from a contiguous amino acid sequence of a v.2 or v.3 B domain, with the heterologous B domain being operably linked to a C domain derived from a contiguous amino acid sequence of a v.2 or v.3 fHBP C domain. Thus, for example, such chimeric fHBP can be described as having a heterologous B domain composed of an N-terminal portion for which a corresponding contiguous amino acid sequence of a v.1 fHBP B domain sequence serves as a scaffold, and a C-terminal portion for which a corresponding contiguous amino acid sequence of a v.2 or v.3 fHBP B domain sequence serves as a scaffold.

As noted above, exemplary chimeric fHBP having a heterologous B domain contain at least 35, at least 40, at least 45, at least 50 residues (and in some embodiments no more than 50 residues) of a contiguous N-terminal amino acid sequence of a B domain of a v.1 fHBP.

Where the chimeric fHBP contains a heterologous C domain, the B domain of the chimeric fHBP comprises a contiguous amino acid sequence of a v.1 fHBP B domain operably linked to heterologous C domain comprising at least N-terminal portion of a v.1 fHBP C domain and a C-terminal portion of a v.2 or v.3 C domain. Exemplary chimeric fHBP of this embodiment contain 2, 4, 6, 8 residues of an N-terminal sequence of a v.1 C domain, with the remainder of the C domain being derived from a v.2 or v.3 C domain amino acid sequence.

Chimeric fHBP contemplated by the present disclosure include those having an amino acid sequence corresponding to a full-length B domain and a full-length C domain, and, optionally, a full-length A domain wherein the chimeric fHBP includes at least a heterologous B domain or a heterologous C domain. Other embodiments include chimeric fHBP having an amino acid sequence corresponding to a fragment of an A domain composed of a contiguous amino acid sequence encompassing amino acid defining an epitope bound by the JAR 4 mAb. Further embodiments include chimeric fHBP in which the C domain is truncated at the C-terminus, with the proviso that epitopes of interest (e.g., one or more of the epitopes bound by mAbs JAR 10, JAR 11, JAR 33, JAR 32/35, and JAR 13) are preserved so as to retain the ability to elicit antibodies that bind these epitopes Chimeric fHBP also include those that lack an A domain, and have an N-terminally truncated B domain, with the proviso that the truncated B domain maintains expression of an epitope(s) of interest. Chimeric fHBP include those having a B domain that expresses an epitope bound by the JAR 5 mAb.

Chimeric polypeptides described herein can include additional heterologous amino acid sequences, e.g., to provide an N-terminal methionine or derivative thereof (e.g., pyroglutamate) as a result of expression in a bacterial host cell (e.g., *E. coli*) and/or to provide a chimeric polypeptide having a fusion partner at its N-terminus or C-terminus. Fusion partners of interest include, for example, glutathione-S-transferase (GST), maltose binding protein (MBP), $His_6$-tag, and the like, as well as leader peptides from other proteins, particularly lipoproteins. Fusion partners can provide for additional features, such as in facilitating isolation and purification of the chimeric polypeptide.

Native fHBP usually contains an N-terminal cysteine to which a lipid moiety can be covalently attached. This cysteine residue is usually lipidated in the naturally-occurring protein, and can be lipidated in the chimeric fHBPs disclosed herein. Thus, in the amino acid sequences described herein (including those presented in any Sequence Listing), reference to "cysteine" or "C" at this position specifically includes reference to both an unmodified cysteine as well as to a cysteine that is lipidated (e.g., due to post-translational modification). Thus, the chimeric fHBP can be lipidated or non-lipidated. Methods for production of lipidated proteins in vitro, (see, e.g., Andersson et al., 2001 J Immunological Methods 255(1-2):135-48) or in vivo are known in the art. For example, lipidated fHBP previously has been purified from the membrane fraction of *E. coli* protein by detergent extraction (Fletcher et al., 2004 Infection and Immunity 72(4):2088-100), which method may be adapted for the production of lipidated chimeric fHBP. Lipidated proteins may be of interest as such can be more immunogenic than soluble protein (see, e.g., Fletcher et al., 2004 Infection and Immunity 72(4):2088-100).

Exemplary chimeric fHBPs are described in detail below.

Exemplary Chimeric fHBPs

The chimeric fHBPs of the present disclosure encompass those that can be described in terms of one or more of, for example, the site at which heterologous sequences are joined within the chimeric fHBP (i.e., the "junction point"), the presence of epitopes specifically bound by a mAb, amino acid sequence, or any combination of such features that may be present in exemplary fHBPs.

Junction Point of Chimeric fHBP

In general, the junction point of the chimeric fHBP is the point at which amino acid sequence of the chimeric fHBP shifts from being derived from a contiguous amino acid sequence of a v.1 fHBP to being derived from contiguous amino acid sequence of a v.2 or v.3 fHBP. The junction point thus provides for an amino acid sequence that is heterologous, i.e., derived from different fHBPs. The N-terminal portion and the C-terminal portions of a heterologous domain (i.e., heterologous B domain or heterologous C domain) of chimeric fHBP are joined at a junction point, with the junction point thus defining the length of the N-terminal and C-terminal portions of the chimeric domain that are derived from a v.1 or v.2/v.3 amino acid sequence.

In general, a B domain amino acid sequence comprising an amino acid sequence N-terminal to the second α helix of fHBP, which includes residues corresponding to those implicated in defining the JAR 5 mAb epitope (i.e., residues at positions 121 and 122 of a B domain v.1 fHBP MC58, which are glycine and lysine, respectively) is denoted as the "N-terminal portion of the B domain" (see, e.g., FIG. 13, FIG. 21 and FIG. 22, Panel A). The amino acid sequence flanking and C-terminal to the N-terminal portion of the B domain is the "C-terminal (or distal) portion of the B domain" and is derived from a contiguous amino acid sequence of a v.2 or v.3 fHBP (FIG. 14 and FIG. 22). Together, the N-terminal and C-terminal portions of the B domain compose a heterologous B domain of a chimeric fHBP of the present disclosure.

Where the chimeric fHBP has a heterologous B domain, the junction point may be positioned at a residue adjacent to the second α helix (AH2) (e.g., adjacent and C-terminal to a residue corresponding to residue 121 or 122 of FIG. 21, e.g., adjacent and C-terminal to one of the residues of GEHTSFDK (SEQ ID NO:43), e.g., adjacent and C-terminal to one of the residues of GEHT (SEQ ID NO:7), N-terminal to AH2), or at a position C-terminal to AH2.

In one embodiment, the junction point of the heterologous B domain can be positioned at any site corresponding to a site after the glycine residue or after the lysine residue, that define a JAR 5 monoclonal antibody (mAb) epitope of a v.1 fHBP (which residue is positioned within the B domain, i.e., at G121 or K122 of v.1 fHBP strain MC58 reference sequence) but before a residue corresponding to a residue defining a JAR 11 mAb epitope of a v.2 fHBP (which residue is positioned in the C domain, i.e., A174 of v.2 fHBP strain 8047 reference sequence). In a related embodiment, the heterologous B domain is provided such that the JAR 5 mAb epitope, the JAR 11 epitope, or both the JAR 5 and JAR 11 epitopes are maintained such that the chimeric fHBP is specifically bound by the respective mAb.

In one embodiment, the junction point is positioned so that the chimeric fHBP contains a heterologous B domain, which has an N-terminal portion composed of a contiguous amino acid sequence of an N-terminal portion of a B domain of a v.1 fHBP containing a JAR 5 epitope (defined in part by G121 of v.1 fHBP strain MC58) with the remaining portion (i.e., the C-terminal portion) of the B domain derived from a contiguous amino acid sequence of the corresponding C-terminal portion of a v.2 or v.3 fHBP B domain. The heterologous B domain is operably linked to a C domain derived from a contiguous amino acid sequence of a v.2 or v.3 fHBP, which can be the same or different v.2 or v.3 fHBP as that from which the C-terminal portion of the B domain is derived.

Exemplary heterologous B domains include those at least 80% identical, at least 85% identical, at least 90% identical, at least 99% identical or more to a contiguous amino acid sequence of a v.1 fHBP corresponding to residues 101-121, 101-122, 101-123, 101-124, 101-125, 101-126, 101-127, 101-128, 101-129, 101-130, 101-131, 101-132, 101-133, 101-134, 101-134, 101-136, 101-137, 101-138, or 101-139 of a v.1 fHBP amino acid sequence, where the numbering is based on MC58 fHBP as a reference. Such heterologous B domains include those having an amino acid sequence that is at least 80% identical, at least 85% identical, at least 90% identical, at least 99% identical or more to a contiguous amino acid sequence of a v.2 or v.3 fHBP so as to provide the remainder of the heterologous B domain having a C-terminus corresponding to residue 164 (again, using MC58 fHBP as a reference sequence of purposes of numbering).

For example, where the heterologous B domain includes residues 101-122 or a v.1 fHBP, the C-terminal portion of the heterologous B domain includes residues 123-164 of a v.2 or v.3 fHBP. Accordingly, the C-terminal portion of the heterologous B domain can include an amino acid sequence at least 80% identical, at least 85% identical, at least 90% identical, at least 99% identical or more to a contiguous amino acid sequence of a v.2 or v.3 fHBP corresponding to residues 122-164, 123-164, 124-164, 125-164, 126-164, 127-164, 128-164, 129-164, 130-164, 131-164, 132-164, 133-164, 134-164, 135-164, 136-164, 137-164, 139-164, or 140-164, where the N-terminal portion of the heterologous B domain is provided by the v.1 sequences exemplified above.

In another embodiment, the junction point is positioned N-terminal to the second α helix (AH2), which are denoted in FIG. 22 by "α". As pointed out above, the residues GEHT (SEQ ID NO:7) are highly conserved across v.1, v.2, and v.3 fHBP variants, and thus can serve as convenient junction point residues, as well as a convenient reference for the position of a junction point in a chimeric fHBP. For example, the junction point can be positioned within 14, 13, 12, 11, 10, 9, 8, 7, 6, 5, 4, 3, 2, or 1 residue(s) N-terminal to GEHT (SEQ ID NO:7) to provide a heterologous B domain (e.g., positioned at a site not more than 14, 13, 12, 11, 10, 9, 8, 7, 6, 5, 4, 3, 2, or 1 residue N-terminal of GEHT (SEQ ID NO:7)); or is positioned within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 residues C-terminal to GEHT (SEQ ID NO:7) (e.g., positioned at a site not more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 residues C-terminal of GEHT (SEQ ID NO:7)), where a junction point at a site less than or equal to 26 residues C-terminal to GEHT provides a heterologous B domain and a junction point positioned at more than 26 residues C-terminal to GEHT (SEQ ID NO:7) produces a chimeric fHBP having a heterologous C domain.

For example, the junction point of the heterologous B domain can be selected such that the heterologous B domain amino acid sequence positioned N-terminal and flanking the amino acid sequence GEHT (SEQ ID NO:7) is derived from a v.1 fHBP B domain amino acid sequence and the heterologous B domain amino acid sequence positioned C-terminal and flanking the GEHT (SEQ ID NO:7) is derived from a v.2 or v.3 fHBP B amino acid sequence.

In some embodiments, the junction point is positioned so as to provide a heterologous B domain comprising an amino acid sequence that is greater than 80% (e.g., at least 81%), at least 85%, at least 90%, at least 95% or identical to an amino acid sequence of (SEQ ID NO: 1)
QSHSALTAFQ TEQIQDSEHS GK where the amino acid sequence optionally provides for an epitope that mediates specific binding of a JAR 5 mAb. Exemplary amino acid substitutions of the above sequence are as follows:

QSHSALTA(F/L)Q TEQ(I/V/E)QD(S/P)E(H/D)S (G/E/R)K.

Exemplary modifications of the amino acid sequences of the heterologous B domain as set out above include, for example, one or more of the following substitutions of SEQ ID NO:1 as follows:
  leucine (L) for the phenylalanine (F) at a residue corresponding to position 9;
  valine (V) or glutamic acid (E) for isoleucine (I) at residue position 14;
  proline (P) for serine (S) at residue position 17;
  aspartic acid (D) for histidine (H) at residue position 19;
  arginine (R) for glutamine (Q) at residue position 28;
  valine (V) for alanine (A) at residue position 35;
  glycine (G) for aspartic acid (D) at residue position 42; or
  lysine (K) for glutamic acid (E) at residue position 46.

In further embodiments, the heterologous B domain comprises an amino acid sequence represented by the formula:

QSHSALTA(F/L)Q TEQ(I/V/E)QD(S/P)E(H/D)S (G/E/R)KMVAKR(Q/R)FR

IGDI(A/V)GEHTA FNQLP (D/S)

In some embodiments, the junction point is positioned so as to provide a heterologous B domain comprising an amino acid sequence that is at least 80%, at least 85%, at least 90%, at least 95% or identical to an amino acid sequence of

TEQIQDSEHS GKMVAKRQFR IGDIAGEHTA FNQLPD, where the amino acid sequence optionally provides for an epitope that mediates specific binding of a JAR 5 mAb.

In other embodiments the heterologous B domain comprises an amino acid sequence that is at least 80%, at least 85%, at least 90%, at least 95% or identical to an amino acid sequence of

QSHSALTAFQ TEQIQDSEHS GKMVAKRQFR IGDIAGEHTA FNQLPD where the amino acid sequence optionally provides for an epitope specifically bound by JAR 5 MAB.

In still other embodiments, the heterologous B domain comprises a sequence at least 80%, at least 85%, at least 90%, at least 95% or identical to an amino acid sequence set out in FIG. 13, which provides an alignment of exemplary chimeric fHBPs III, IV and V sequences in the region of the junction point, which is indicated by the box. The residue, G121, implicated in the JAR 5 epitope is shown in bold and underlined.

In some embodiments, the junction point is positioned so as to provide a heterologous B domain comprising an amino acid sequence that is at least 80%, at least 85%, at least 90%, at least 95% or identical to an amino acid sequence of:

LTAFQ TEQIQDSEHS GKMVAKRQFR IGDIA where the amino acid sequence optionally provides for an epitope that mediates specific binding of a JAR 5 mAb.

In another embodiment, the junction point of the chimeric fHBP is positioned so that the chimeric fHBP contains a heterologous C domain composed of a contiguous amino acid sequence of an N-terminal portion of a C domain of a v.1 fHBP and a contiguous amino acid sequence of a C-terminal portion of a C domain of a v.2 or v.3 fHBP.

For example, the junction point of a chimeric fHBP having a heterologous C domain can be in the loop regions of the β-barrel of the C domain, or in any highly conserved segment, for example at residues D160 or I170. In one embodiment, the heterologous C domain includes an N-terminal sequence of KLTYTIDFA (SEQ ID NO:50).

Exemplary chimeric fHBP are provided in the Examples below. The present disclosure contemplates these exemplary chimeric fHBP, as well as chimeric fHBP having at least 85%, at least 90%, at least 95% or greater amino acid sequence identity to the amino acid sequences of these exemplary chimeric fHBP (e.g., Chimera I, Chimera II, Chimera IIb, Chimera III, Chimera IV, and Chimera V). The amino acid and nucleic acid sequences encoding Chimera I, Chimera II, Chimera ill), Chimera III, Chimera IV, and Chimera V are provided in FIGS. 23, 24, 25, 26, 27, and 28, respectively. The asterisk denotes the C-terminus of the amino acid sequence (corresponding to the stop codon of the encoding nucleic acid).

Inclusion or Maintenance of Epitope Pairs that Elicit Antibodies that Exhibit Enhanced Bactericidal Activity when Both are Bound Chimeric fHBP encompass chimeric fHBP that contain pairs of epitopes that elicit antibodies that, when both are bound to their respective epitopes, exhibit enhanced bactericidal activity against N. meningitidis than when either one is bound alone. Chimeric fHBP can be designed so as to ensure that such epitopes are maintained or to introduce such epitopes (e.g., by modification of an fHBP amino acid sequence to include a pair of epitopes heterologous to that fHBP amino acid sequence).

In general (and subject to the exception below), the distance between epitopes of such epitope pairs is selected so as to be less than 27 Å but more than 14 Å, and are usually located within a distance of about 18 Å-20 Å. As discussed in the Examples below, a greater bactericidal effect was observed when two antibodies bound epitopes located at distances within these parameters. Without being held to theory, when bound by their respective antibodies, the distance between the epitopes is sufficient to facilitate interaction of the antibodies with factors of the complement cascade, but not so close as to result in inhibition of binding due to steric hindrance. Chimeric fHBP containing such epitopes for v.2 and v.3 strains can thus provide for production of antibodies having greater bactericidal activity against such strains. Examples of such epitope pairs are those epitopes bound by JAR 10 and JAR 11 (fHBP v.2); and by JAR 33 and JAR 32/35 (JAR 32 and JAR 35 bind to the same or overlapping epitopes) (fHBP v.3).

Chimeric fHBPs can also include epitope pairs where one epitope of the pair is defined by binding by the mAb JAR 4 and the second epitope is bound by an antibody that inhibits fH binding. Such an epitope pair is not necessarily subject to the constraints on distance between the epitopes as discussed above, with the proviso that the epitopes are not so close as to inhibit binding of their respective antibodies. As discussed in the Examples below, binding of an antibody that inhibits fH binding can be bactericidal along with another mAb that does not inhibit fH binding. For example, a mAb pair such as JAR 4 along with any anti-v.1 or v.2 mAb that blocks fH binding can provide for production of antibodies that have enhanced bactericidal activity.

Inclusion or Maintenance of Epitopes that Elicit Antibodies that Inhibit fH Binding Chimeric fHBPs can be designed so as to include an epitope(s) that elicits antibodies that, when bound to fHBP, inhibit fH binding. For example, as set out below, when the epitopes bound by JAR 13 (v.2 epitope), JAR 11 (v.2 epitope), and JAR 32/35 (v.3 epitope) are bound by antibody, binding of fHBP to fH is inhibited. Thus, the presence of such fH-binding epitopes in the chimeric fHBP polypeptides can provide for production of antibodies that can facilitate protection through this pathway.

Nucleic Acid Encoding Chimeric fHBP

The chimeric fHBP can be generated using recombinant techniques to manipulate nucleic acids of different fHBPs known in the art to provide constructs encoding a chimeric fHBP of interest. As noted above, nucleic acids encoding a variety of different v.1, v.2, and v.3 fHBPs of N. meningitidis are available in the art, and their nucleotide sequences are known.

Amino acid and nucleic acid sequences of exemplary chimeric fHBPs are provided in FIGS. 23-28. It will be appreciated that the nucleotide sequences encoding the chimeric fHBPs can be modified so as to optimize the codon usage to facilitate expression in a host cell of interest (e.g., E. coli, N. meningitidis, human (as in the case of a DNA-based vaccine), and the like). Methods for production of codon optimized sequences are known in the art.

Methods of Production

Chimeric fHBPs can be produced by any suitable method, including recombinant and non-recombinant methods (e.g., chemical synthesis). Where the chimeric fHBP is produced using recombinant techniques, the methods can involve any suitable construct and any suitable host cell, which can be a prokaryotic or eukaryotic cell, usually a bacterial or yeast host cell, more usually a bacterial cell. Methods for introduction of genetic material into host cells include, for example, transformation, electroporation, conjugation, calcium phosphate methods and the like. The method for transfer can be selected so as to provide for stable expression of the introduced chimeric fHBP-encoding nucleic acid. The chimeric fHBP-encoding nucleic acid can be provided as an inheritable episomal element (e.g., plasmid) or can be genomically integrated.

Suitable vectors for transferring chimeric fHBP-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

In one embodiment, the vector is an expression vector based on episomal plasmids containing selectable drug resistance markers and elements that provide for autonomous replication in different host cells (e.g., in both E. coli and N. meningitidis). One example of such a "shuttle vector" is the plasmid pFP10 (Pagotto et al. Gene 2000 244:13-19).

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a chimeric fHBP, may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of a chimeric fHBP of interest, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHBP from which the chimeric fHBP is derived, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a procaryotic host for cloning and amplification. In addition the expression construct may contain a selectable marker gene to allow the selection of transformed host cells. Selection genes are well known in the art and will vary with the host cell used.

It should be noted that chimeric fHBP of the present disclosure may comprise additional elements, such as a detectable label, e.g., a radioactive label, a fluorescent label, a biotin label, an immunologically detectable label (e.g., an HA tag, a poly-Histidine tag) and the like. Additional elements of chimeric fHBP can be provided to facilitate isolation (e.g., biotin tag, immunologically detectable tag) through various methods (e.g., affinity capture, etc.). Chimeric fHBP can optionally be immobilized on a support through covalent or non-covalent attachment.

Isolation and purification of chimeric fHBP can be accomplished according to methods known in the art. For example, chimeric fHBP can be isolated from a lysate of cells genetically modified to express a chimeric fHBP, or from a synthetic reaction mix, by immunoaffinity purification, which generally involves contacting the sample with an anti-chimeric fHBP antibody (e.g., an anti-chimeric fHBP mAb, such as a JAR 5 mAb or other appropriate JAR mAb described herein), washing to remove non-specifically bound material, and eluting specifically bound chimeric fHBP. Isolated chimeric fHBP can be further purified by dialysis and other methods normally employed in protein purification methods. In one embodiment, the chimeric fHBP can be isolated using metal chelate chromatography methods.

Host Cells

Any of a number of suitable host cells can be used in the production of chimeric fHBP. In general, the chimeric fHBP described herein may be expressed in prokaryotes or eukaryotes, usually bacteria, more usually *E. coli* or *Neisseria* (e.g., *N. meningitidis*) in accordance with conventional techniques. Thus, the present disclosure further provides a genetically modified host cell, which contains a nucleic acid encoding a chimeric fHBP. Host cells for production (including large scale production) of a chimeric fHBP can be selected from any of a variety of available host cells. Exemplary host cells for expression include those of a prokaryotic or eukaryotic unicellular organism, such as bacteria (e.g., *Escherichia coli* strains), yeast (e.g., *S. cerevisiae, Pichia* spp., and the like), and may include host cells originally derived from a higher organism such as insects, vertebrates, particularly mammals, (e.g. CHO, HEK, and the like). Generally bacterial host cells and yeast are of particular interest for chimeric fHBP production.

Chimeric fHBPs can be prepared in substantially pure or substantially isolated form (i.e., substantially free from other Neisserial or host cell polypeptides) or substantially isolated form. In certain embodiments, the chimeric fHBP is present in a composition that is enriched for the polypeptide relative to other components that may be present (e.g., other polypeptides or other host cell components). Purified chimeric fHBP can be provided such that the polypeptide is present in a composition that is substantially free of other expressed polypeptides, e.g., less than 90%, usually less than 60% and more usually less than 50% of the composition is made up of other expressed polypeptides.

Host Cells for Vesicle Production

Where a chimeric fHBP is to be provided in a membrane vesicle (as discussed in more detail below), a Neisserial host cell is genetically modified to express a chimeric fHBP. Any of a variety of *Neisseria* spp. strains can be modified to produce a chimeric fHBP, and, optionally, which produce or can be modified to produce other antigens of interest, such as PorA, can be used in the methods disclosed herein.

Methods and vectors to provide for genetic modification of Neisserial strains and expression of a desired polypeptide are known in the art. Exemplary vectors and methods are provided in WO 02/09746 and O'Dwyer et al. Infect Immun 2004; 72:6511-80. Strong promoters, particularly constitutive strong promoters are of particular interest. Exemplary promoters include the promoters of porA, porB, lbpB, tbpB, p110, hpuAB, lgtF, opa, p110, lst, hpuAB. and rmp.

Pathogenic *Neisseria* spp. or strains derived from pathogenic *Neisseria* spp., particularly strains pathogenic for humans or derived from strains pathogenic or commensal for humans, are of particular interest for use in membrane vesicle production. Exemplary Neisserial spp. include *N. meningitidis, N. flavescens, N. gonorrhoeae, N. lactamica, N. polysaccharea, N. cinerea, N. mucosa, N. subflava, N. sicca, N. elongata*, and the like.

*N. meningitidis* strains are of particular interest for genetic modification to express a chimeric fHBP and for use in vesicle production. The strain used for vesicle production can be selected according to a number of different characteristics that may be desired. For example, the strain may be selected according to: a desired PorA type (a "serosubtype", as described above), capsular group, serotype, and the like; decreased capsular polysaccharide production; and the like. For example, the production strain can produce any desired PorA polypeptide, and may express one or more PorA polypeptides (either naturally or due to genetic engineering). Exemplary strains includes those that produce a PorA polypeptide which confers a serosubtype of P1.7,16; P1.19,15; P1.7,1; P1.5,2; P1.22a,14; P1.14; P1.5,10; P1.7,4; P1.12,13; as well as variants of such PorA polypeptides which may or may not retain reactivity with conventional serologic reagents used in serosubtyping. Also of interest are PorA polypeptides characterized according to PorA variable region (VR) typing (see, e.g., Russell et al. Emerging Infect Dis 2004 10:674-678; Sacchi C T, et al, Clin Diagn Lab Immunol 1998; 5:845-55; Sacchi et al, J. Infect Dis 2000; 182:1169-1176). A substantial number of distinct VR types have been identified, which can be classified into VR1 and VR2 family "prototypes". A web-accessible database describing this nomenclature and its relationship to previous typing schemes is found at *neisseria*.org/nm/typing/pora. Alignments of exemplary PorA VR1 and VR2 types is provided in Russell et al. Emerging Infect Dis 2004 10:674-678.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell ELISA using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. J. Infect. Dis. (2003) 187(10):1616-28), as well as methods of identifying and/or generating capsule-deficient strains (see, e.g., Fisseha et al. (2005) Infect. Immun. 73(7):4070-4080; Stephens et al. (1991) Infect Immun 59(11):4097-102; Frosch et al. (1990) Mol Microbiol. 1990 4(7):1215-1218) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) J Bacteriol. 176(5):1530-4).

Capsule-deficient strains can also be generated from naturally-occurring strains using non-recombinant techniques, e.g., by use of bactericidal anti-capsular antibodies to select for strains that reduced in capsular polysaccharide.

Where the disclosure involves use of two or more strains (e.g., to produce antigenic compositions containing a chimeric fHBP-presenting vesicles from different strains), the strains can be selected so as to differ in one or more strain characteristics, e.g., to provide for vesicles that differ in the chimeric fHBP used, PorA, and the like.

Preparation of Vesicles

The antigenic compositions contemplated by the present disclosure generally include vesicles prepared from Neisserial cells that express a chimeric fHBP. As referred to herein "vesicles" is meant to encompass outer membrane vesicles as well as microvesicles (which are also referred to as blebs).

In one embodiment, the antigenic composition comprises outer membrane vesicles (OMV) prepared from the outer membrane of a cultured strain of *Neisseria meningitidis* spp. genetically modified to express a chimeric fHBP. OMVs may be obtained from *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

In another embodiment, the antigenic composition comprises microvesicles (MV) (or "blebs") containing chimeric fHBP, where the MV or blebs are released during culture of a *Neisseria meningitidis* strain genetically modified to express a chimeric fHBP. For example, MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be of particular interest (for examples of *N. meningitidis* strains having different NspA production levels, see, e.g., Moe et al. (1999 Infect. Immun. 67: 5664). Other strains of interest for use in production of blebs include strains having an inactivated GN33 gene, which encodes a lipoprotein required for cell separation, membrane architecture and virulence (see, e.g., Adu-Bobie et al. Infect Immun 2004; 72:1914-1919).

The antigenic compositions of the present disclosure can comprise vesicles from one strain, or from 2, 3, 4, 5 or more strains, which strains may be homologous or heterologous, usually heterologous, to one another. For example, the strains may be homologous or heterologous with respect to PorA. In one embodiment, the vesicles can be prepared from strains that express more than one chimeric fHBP (e.g., 1, 2, 3, or more chimeric fHBP) which may be composed of fHBP amino acid sequences from different variants (v.1, v.2, or v.3) or subvariants (e.g., a subvariant of v.1, v.2, or v.3).

The antigenic compositions can comprise a mixture of OMVs and MVs presenting the same or different chimeric fHBPs, where the chimeric fHBPs may optionally present epitopes from different combinations of fHBP variants and/or subvariants and where the OMVs and/or MVs may be from the same or different strains. Vesicles from different strains can be administered as a mixture, or can be administered serially.

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauroylsarcosinate, EMPIGEN BB, TRITON X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

In some embodiments the vesicles of the antigenic compositions are prepared without detergent, e.g., without use of deoxycholate. Although detergent treatment is useful to remove endotoxin activity, it may deplete the native fHBP lipoprotein and/or chimeric fHBP (including lipidated chimeric fHBP) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from *Neisseria* mutants in which lipooligosaccharide or other antigens that may be undesirable in a vaccine (e.g. Rmp) is reduced or eliminated.

Vesicles can be prepared from *N. meningitidis* strains that contain genetic modifications that result in decreased or no detectable toxic activity of lipid A. For example, such strain can be genetically modified in lipid A biosynthesis (Steeghs et al. Infect Immun 1999; 67:4988-93; van der Ley et al. Infect Immun 2001; 69:5981-90; Steeghs et al. J Endotoxin Res 2004; 10:113-9; Fissha et al, Infect Immun 73:4070, 2005). The immunogenic compositions may be detoxified by modification of LPS, such as downregulation and/or inactivation of the enzymes encoded by lpxL1 or lpxL2, respectively. Production of a penta-acylated lipid A made in lpxL1 mutants indicates that the enzyme encoded by lpxL1 adds the C12 to the N-linked 3-OH C14 at the 2' position of GlcN II. The major lipid A species found in lpxL2 mutants is tetra-acylated, indicating the enzyme encoded by lpxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. 2001; 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decreases the toxic activity of lipid A. Of particular interest for use in production of vesicles (e.g., MV or OMV) are *N. meningitidis* strains genetically modified so as to provide for decreased or no detectable functional LpxL1-encoded protein. Such vesicles provide for reduced toxicity as compared to *N. meningitidis* strains that are wild-type for LPS production, while retaining immunogenicity of chimeric fHBP.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low Mg++ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. 1994. In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. 1993, Science 259: 361-365; Porro et al. Prog Clin Biol Res. 1998; 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Formulations

"Antigen composition", "antigenic composition" or "immunogenic composition" is used herein as a matter of convenience to refer generically to compositions comprising a chimeric fHBP as disclosed herein, which chimeric fHBP may be optionally conjugated to further enhance immunogenicity. Compositions useful for eliciting antibodies, particularly antibodies against *Neisseria meningitidis* group B (NmB), in a human are specifically contemplated by the present disclosure. Antigenic compositions can contain 2 or more different chimeric fHBPs, where the chimeric fHBPs may present epitopes from different combinations of fHBP variants and/or subvariants.

Antigenic compositions generally comprise an immunologically effective amount of chimeric fHBP, and may further include other compatible components, as needed. By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by *Neisseria*, particularly *N. meningitidis*, more particularly Group B *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present invention in an amount sufficient to produce the desired effect, which compositions are provided in association with a pharmaceutically acceptable excipient (e.g., pharmaceutically acceptable diluent, carrier or vehicle). The antigenic composition may be administered in conjunction with other immunoregulatory agents.

Antigenic compositions can be provided in a pharmaceutically acceptable excipient, which can be a solution such as a sterile aqueous solution, often a saline solution, or they can be provided in powder form. Such excipients can be substantially inert, if desired.

The antigenic compositions can further comprise an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80™, 0.5% w/v SPAN 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immuno stimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing MTP-PE) formulated into submicron particles using a microfluidizer, (b) SAF, containing 10% Squalane, 0.4% TWEEN 80, 5% PLURONIC-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr opin Mol Ther2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997, 27, 2340-2344; Moldoveami e/ al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157,2116-2122; Messina et al, J. Immunol, 1991, 147, 1759-1764; Yi et al, J. Immunol, 1996, 157,4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g WO 00/23105; (12) a saponin and an oil-in-water emulsion e.g. WO 99/11241; (13) a saponin (e.g QS21)+3dMPL+IM2 (optionally+a sterol) e.g WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human are of particular interest.

The antigen compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of chimeric fHBP in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

Chimeric fHBP-containing formulations can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

Chimeric fHBP-containing formulations can also provided so as to enhance serum half-life of chimeric fHBP following administration. For example, where isolated chimeric fHBP are formulated for injection, the chimeric fHBP may be provided in a liposome formulation, prepared as a colloid, or other conventional techniques for extending serum half-life. A variety of methods are available for preparing liposomes, as described in, e.g., Szoka et al., Ann Rev. Biophys. Bioeng. 9:467 (1980), U.S. Pat. Nos. 4,235, 871, 4,501,728 and 4,837,028. The preparations may also be provided in controlled release or slow-release forms.

Immunization

The chimeric fHBP-containing antigenic compositions are generally administered to a human subject that is at risk of acquiring a Neisserial disease so as to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The chimeric fHBP-containing antigenic compositions are generally administered in an amount effective to elicit an immune response, particularly a humoral immune response, in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable in oral, nasal, or topical administration routes. The initial administration can be followed by booster immunization of the same of different chimeric fHBP-containing antigenic composition. Usually vaccination involves at least one booster, more usually two boosters.

In general immunization can be accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An anti-chimeric fHBP immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

In one embodiment, the antigenic compositions can be administered to a human subject that is immunologically naive with respect to *Neisseria meningitidis*. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by *Neisseria*).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

Gene Cloning.

Wild-type fHBP genes were amplified from genomic DNA by PCR and cloned into pGEM-T-Easy (Promega). The resulting plasmids were treated with the restriction enzymes NdeI and XhoI and the approximately 800 basepair fragments containing the fHBP coding sequences were ligated into pET21b (Novagen) cut with the same two enzymes. The plasmid clones were confirmed by DNA sequence determination of PCR products obtained by the amplification of the plasmid with primers specific for the T7 promotor and terminator regions. The plasmids encoded the full-length fHBP proteins except for the amino-terminal 19 amino acid signal sequence and 7 presumably flexible N-terminal residues, and included a C-terminal hexa-histidine ($His_6$) tag originating from the pET21b plasmid.

fHBP Chimera I lacking a signal sequence was constructed by PCR amplification of the region encoding residues 8-135 from genomic DNA from strain MC58 (fHBP v.1) and that encoding residues 136-255 from strain 8047 (v.2). The two fragments, including an overlapping region of 48 base pairs centered around amino acids 136-139, were assembled by PCR amplification using external, gene-specific primers containing the NdeI and XhoI restriction sites. The chimeric gene was cloned into pET21b as described for wild-type genes above.

Site-Specific Mutagenesis.

Site-specific mutagenesis was used to test predictions of amino acid residues involved in anti-fHBP mAb epitopes and to create Chimera II. Mutagenesis was performed using the QuikChange II kit (Stratagene) using 10 ng of plasmid template and the manufacturer's protocols. For testing residues putatively involved in mAb epitopes, mutagenesis reactions were performed on pET21-based plasmids encoding wild-type fHBP genes from various strains. A residue in a reactive sequence was changed to that naturally present in a non-reactive sequence or vice versa. To construct Chimera II, site-specific mutagenesis was used to introduce the A174K substitution into the pET21 plasmid encoding Chimera I. Mutant fHBP genes were confirmed by DNA sequencing as described for the wild-type plasmids, above.

fHBP Expression and Purification.

Wild-type, mutant and chimeric fHBPs were expressed in *Escherichia coli* BL21(DE3) (Novagen). fHBP purifications were performed from 1 L cultures. Mid-exponential cultures (optical density at 600 nm of 0.5-0.6) were grown at 37° C., induced with 0.5 mM isopropylthiogalactoside for 3-4 h and the bacteria harvested by centrifugation. The cells were lysed by incubation with chicken egg white lysozyme (Sigma) and two freeze/thaw cycles. Bacterial lysates were treated with DNase and RNase (Sigma) and protease inhibitors (Complete EDTA-free, Roche) and clarified by centrifugation at 13,000×g. Recombinant fHBPs were purified by nickel chelate chromatography using Ni-NTA agarose (Qiagen) and buffers recommended by the supplier. Fractions containing purified fHBP were pooled and dialyzed against PBS (Roche) containing 5% (w/v) sucrose and 0.01% $NaN_3$, filter sterilized and stored at 4° C.

mAb Preparation.

We generated hybridoma cell lines from spleens from CD-1 mice immunized with recombinant fHBP variant group 2 (gene from strain 2996) or variant group 3 (gene from strain M1239) using methods previously described for preparation of hybridoma cell lines secreting mAbs against fHBP v.1 protein (Welsch et al., J. Immunol. 2004). mAbs were precipitated from tissue culture supernatants with 50% saturated $(NH_4)_2SO_4$ and dialyzed against phosphate-buffered saline (PBS; Roche). IgG isotypes were determined using Clonotyping-AP reagents (Southern Biotech).

Direct-Binding and Inhibition ELISA.

Binding of the mAbs to recombinant fHBP was measured by ELISA. The wells of a microtiter plate (Immulon 2B; Thermo Electron Corp.) were coated with 1 µg/ml of recombinant fHBP in PBS and incubated overnight at 4° C. The plates were blocked with PBS containing 0.1% Tween-20 (Sigma) (PBST) and 1% BSA (Sigma). The primary antibodies were anti-fHBP mAbs (0.016 to 5 µg/ml) and the secondary antibody was rabbit anti-mouse IgG-alkaline phosphatase (Zymed; 1:5,000), each diluted in PBST. After 1 h at room temperature, alkaline phosphatase substrate (Sigma) was added and the absorbance at 405 nm was measured after 30 min.

For competitive inhibition ELISAs, one mAb was held at a fixed concentration sufficient to obtain an OD at 405 nm of 1.0 determined by direct binding ELISA, as described above. A second mAb of a different isotype was added together with the first mAb to the wells of a microtiter plate coated with the antigen as described above, at concentrations ranging from 0.4 to 50 g/ml. The secondary mAb was an isotype specific mouse anti-IgG-alkaline phosphatase conjugate. The ELISA was developed as described above.

Inhibition of Binding of Factor H.

The ability of an anti-fHBP mAb to inhibit binding of fH to fHBP was measured by ELISA. Wells of a microtiter plate were coated with rfHBP as described above. Dilutions containing 0.016 to 50 µg/ml of the mAb were added to the wells together with 50 µg/ml purified fH (Complement Technology, Inc.). The plates were incubated overnight at 4° C. Bound fH was detected with goat polyclonal anti-fH (Bethyl Laboratories) (1:1000) followed by mouse anti-goat IgG alkaline phosphatase conjugate (Santa Cruz Biotech) (1:2000). Both steps were performed at room temperature for 2 hours. After washing, substrate was added and developed as described above for the antibody binding ELISA.

Western Blotting.

One mL of bacterial culture was grown and induced as described above (see fHBP expression and purification, above). The cells were harvested by centrifugation and were resuspended in 0.5 mL of 1×LDS sample buffer (Invitrogen) containing 25 mM 2-ME.Bacterial lysates were separated by SDS-PAGE using 4-12% NuPAGE polyacrylamide gels and MES SDS-PAGE buffer (Invitrogen). Proteins were transferred to polyvinylidene difluoride (PVDF) membranes (Immobilon-P; Millipore). The membranes were blocked using PBST containing 2% nonfat dry milk (Carnation, Nestle, Inc.). The membranes were washed, incubated with the different anti-fHBP mAbs (1 to 5 µg/ml) or, as a control for protein expression by the different clones, 0.02 µg/ml of Penta-His mAb (Qiagen). The membranes were washed in PBST and incubated with a 1:10,000 dilution of a rabbit anti-mouse IgG-horseradish peroxidase conjugate (Zymed) and washed again. The membranes were developed with a chemiluminescent substrate (ECL$^+$; GE Healthcare) and visualized on a Storm 840 imager (Molecular Dynamics).

Mouse immunization. Groups (5 mice each) of five-week old CD-1 mice (Charles River) were immunized with four doses containing 20 µg of wild-type or chimeric fHBP vaccines or adjuvant alone at two-week intervals. Each experimental or control vaccine was administered with aluminum hydroxide or Freund's adjuvant (FA) (complete FA for the first dose and incomplete FA for subsequent doses).

Bactericidal activity. Complement-mediated bactericidal activity was measured as described previously using washed, log-phase bacteria grown in Mueller-Hinton broth supplemented with 0.25% glucose and 0.02 mM CMP-NANA to an $OD_{620}$ of 0.6. The buffer was Dulbecco's phosphate buffered saline (Mediatech, Inc.) containing 0.9 mM $CaCl_2 \times 2H_2O$, 0.5 mM $MgCl_2 \times 6$ $H_2O$ and 1% (w/v) BSA. The complement source was human serum from a healthy adult with no detectable intrinsic bactericidal activity. For synergism of mAb bactericidal activity, equal quantities of two mAbs ranging from 0.4 to 50 ug/ml (final concentration) were used. The bactericidal activity ($BC_{50}$) of the mouse antiserum (or mAb combination) was defined by the dilution (or mAb concentration) that gave a 50% decrease in the number of CFU after 60 min incubation at 37° C. as compared with the CFU at time 0 in the negative control reactions.

OVERVIEW OF EXAMPLES

This study used a panel of twelve murine monoclonal antibodies (mAbs) that had been prepared against recombinant proteins representative of the three major variant groups of factor H binding protein (fHBP). These variant groups are designated variant 1 (v.1; Welsch et al. J Immunol 2004; 172: 5606-15), variant 2 (v.2, Beernink et al. J Infect Dis 2007; 195:1472-9) and v.3 (Beernink et al, (2008) Infect Immun 76: 4232-4240). As illustrated by the summary of selected features of these mAbs in the tables of FIGS. 17 and 18, each of these mAbs is bactericidal when combined with a second mAb. In addition JAR 1 and JAR 3 are individually bactericidal when tested against certain strains expressing v.1 fHBP.

The results summarized in FIG. 18 are evidence that the epitopes recognized by each of the mAbs is surface-exposed on encapsulated meningococcal strains and capable of interacting with protective antibodies.

Nine of these JAR mAbs were used as tools to determine amino acid residues in fHBP that contribute to the epitopes for binding of these mAbs so as to provide for structural predictions on the locations of epitopes of fHBP from different variant groups that interact with bactericidal antibodies. This information could then be used to construct chimeric fHBP vaccines that express epitopes from more than one variant group and that are capable of eliciting antibodies that confer protection against strains expressing different fHBP variants.

For convenience in facilitating prior studies aimed at identifying bactericidal regions of fHBP, the protein was divided into three domains, designated A, B and C (Giuliani et all. Infect Immun 2005; 73:1151-60). As discussed above, the A domain is highly conserved across v.1 and v.2 variant groups, whereas the B and C domains contain sequences that diverge among strains. Previously, the only known fHBP epitope interacting with a bactericidal mAb was located in the C domain at R204 (Giuliani et al. supra). (Note that the convention of numbering amino acid residues beginning with the first residue after the signal sequence is adopted herein). However, a chimeric protein vaccine composed of the B domain from a variant 3 strain ($B_3$) fused with the C domain of a variant 1 strain ($C_1$) failed to elicit protective bactericidal responses against strains with either variant 1 or 3 fHBP.

As will be set out in more detail below, the inventors identified the location of an epitope defined by two anti-fHBP mAbs, JAR 3 and 5 (referred to herein as the "JAR3/5" epitope), in the $B_1$ domain around residue G121. JAR 3 individually was known to be bactericidal with human complement against strains from sequence type (ST) complex 32 (Welsch et al. J Immunol 2004; 172:5606-15) and, both JAR 3 and JAR 5 when combined with other mAbs were broadly bactericidal against strains expressing subvariants of variant 1 fHBP (Welsch et al., supra). JAR 3 (Madico et al. J Immunol 2006; 177:501-10) and JAR 5 also inhibited binding of factor H (fH) to the surface of encapsulated *N. meningitidis* strains. It should be noted that with the exception of JAR3/5, all of the other mAbs mapped to date were found to bind to epitopes that are part of the C domain.

The observations relating to the JAR 3/5 epitope being present in the B domain formed the rationale for fusing the portion of the protein of v.1 B domain containing the JAR3/5 epitope (e.g., up to residue 136) with the remaining portion of the B domain and entire C domain of the v.2 protein (Chimera I). Inclusion of the JAR 3/5 epitope from v.1 at resides near and including G121 elicited broadly protective antibodies to v.1 and v.1 subvariant strains.

Further, by inclusion of the other epitopes such as JAR 10, 11 and 13, the chimeric fHBP provided for a polypeptide that elicited broadly protective antibodies against v.2 or v.3 strains. When mice were immunized with either Chimera I or Chimera II vaccines, the animals developed serum bactericidal antibody responses against strains expressing fHBP v.1, v.2 or v.3 whereas as expected the serum bactericidal antibody responses of the control mice immunized with the wild-type recombinant fHBP v.1 were nearly entirely restricted to strains expressing fHBP v.1, and those of the control mice immunized with the wild-type recombinant fHBP v.2 were restricted to v.2 or v.3 (which from previous studies were known to cross-react (Masignani 2007 J Exp Med, supra and Beernink 2007 J. Infect Dis supra). The results provide proof of concept that an individual chimeric protein can elicit antibodies that are bactericidal with human complement against strains expressing fHBP from different variant groups.

Thus, in contrast to the $B_3C_1$ chimeric previously reported, a chimeric protein vaccine composed of the $A_1$ domain (which is highly conserved across variant 1 and 2), the N-terminal portion of the $B_1$ domain expressing the JAR 3/5 epitope fused with the distal terminal portion of the $B_1$ domain and $C_1$ domain elicited cross-protective bactericidal antibodies in immunized mice.

The JAR 11 epitope is expressed by about one-third of disease-producing *N. meningitidis* strains in the U.S. that express fHBP v.2 or v.3 (Beernink 2007 J. Infect Dis, supra). Approximately 50 percent of the JAR 11-negative strains with v.2 or v.3 fHBP express the JAR 32/35 epitope. Therefore, to increase coverage against these strains, the Chimera II vaccine was prepared, in which a single amino acid change, A174K, was introduced into the C domain that inactivated the epitope recognized by JAR 11 and introduced the epitope recognized by JAR 32/35. Despite engineering expression of the JAR 11 epitope in Chimera I and the JAR 32 epitope in Chimera II, there was no statistically significant differences in the respective serum bactericidal antibody responses of mice immunized either vaccine against strains expressing v.2 or v.3 fHBP that were JAR 11-positive or JAR 32-positive.

As set out below, it was later found that binding of antibody to an epitope located near residue 174 (i.e., JAR 11 in some strains, and JAR 32 in others; see FIG. 1) was not sufficient to elicit significant complement-mediated bactericidal activity in the absence of a second mAb binding to an epitope associated with ion pair at residues 180 and 192 (such as JAR 10 in some strains or JAR 33 in others (See Table in FIG. 20)). Among wild-type strains expressing fHBP v.2 or v.3, expression of JAR 32 is often associated with expression of JAR 33 (for example, strains 03S-0658, M1239 and SK104, Table in FIG. 8A), while expression of JAR 11 is usually associated with expression of JAR 10 (see for example our strains 8047, MD1435 and MD1321, FIG. 8A). This insight pointed to production of chimeric fHBP vaccines effective against JAR 32-positive strains by also introducing the JAR 33 epitope.

Further, as set out below, it was discovered that bactericidal activity of antibodies is enhanced when two antibodies bind their respective epitopes located at a distance of about 18-20 Å. Stated differently, a greater bactericidal effect was observed when two antibodies bound epitopes located about 18-20 Å apart on the chimeric fHBP compared to the bactericidal effect of these antibodies alone. In contrast, binding of two antibodies to epitopes positioned at a greater distance apart (e.g., ≥ about 27 Å) did not enhance bactericidal activity, which may be due to the reduced ability of these bound antibodies to provide for enhanced interaction with C1q of the complement cascade. Binding of two antibodies to epitopes positioned ≤ about 14 Å apart also did not provide for enhanced bactericidal activity, which may be the result of steric hindrance of binding of one antibody by the other. Thus, chimeric fHBP which contain epitopes that elicit antibodies that bind to epitopes within about 18-20 Å apart can provide for further enhanced bactericidal antibody production. Examples of such epitope pairs are those epitopes bound by JAR 10 and JAR 11; and by JAR 33 and JAR 32/35 (JAR 32 and JAR 35 bind to the same (or overlapping) epitopes).

The effect of chimeric fHBP polypeptides as vaccines can be further enhanced by including epitopes that elicit antibodies that block fH binding. For example, as set out below, when the epitopes bound by JAR 13 (v.2 epitope), JAR 11 (v.2 epitope), and JAR 32/35 (v.3 epitope) are bound by antibody, binding of fHBP to fH is inhibited. Thus, the presence of such fH-binding epitopes in the chimeric fHBP polypeptides can provide for production of antibodies that can facilitate protection through this pathway.

Details of the studies that led to this discovery are set out below.

Example 1

Identification of Amino Acid Residues of fHBP Epitopes Important for JAR 3/5 mAb Binding Selected known properties of JAR mAbs are summarized in the tables of FIGS. 17 and 18. Notably, JAR 3 and JAR 5 were known to bind to v.1 or subvariants of v.1 fHBP expressed by strains MC58, 4243, M1390, and NZ98/254 but not to strain M6190 (Welsch et al. J Immunol 2004; 172:5606-15). Further, fHBP expressed by M6190 had an arginine at position 121 (R121) whereas the fHBPs from the four reactive strains had glycine at position 121 (G121) (Welsch et al. J Immunol 2004; 172:5606-15).

In order to confirm that G121 was important for JAR 3 and JAR 5 binding, site-specific mutagenesis was used to change the glycine residue at position 121 in the fHBP sequence of strain MC58 to arginine.

As illustrated in the Western blots of FIG. 1, the G121R substitution resulted in loss of JAR 3 and JAR 5 reactivity (FIG. 1, Panel A). The converse change in fHBP from strain M6190, R121G, introduced the JAR 5 epitope (FIG. 1, Panel A, lane 6) and, to a lesser extent, the JAR 3 epitope (FIG. 1, Panel B, lane 6). The weaker signals for the M6190 mutant R140G protein, particularly for JAR 3, indicated that additional residues may have been important for these epitopes. The Penta-His control mAb showed that the wild-type and mutant proteins were produced in similar quantities (FIG. 1, Panel C).

Additional evidence that JAR 3 and JAR 5 recognized overlapping epitopes was derived from competitive inhibition experiments.

Figure 2:
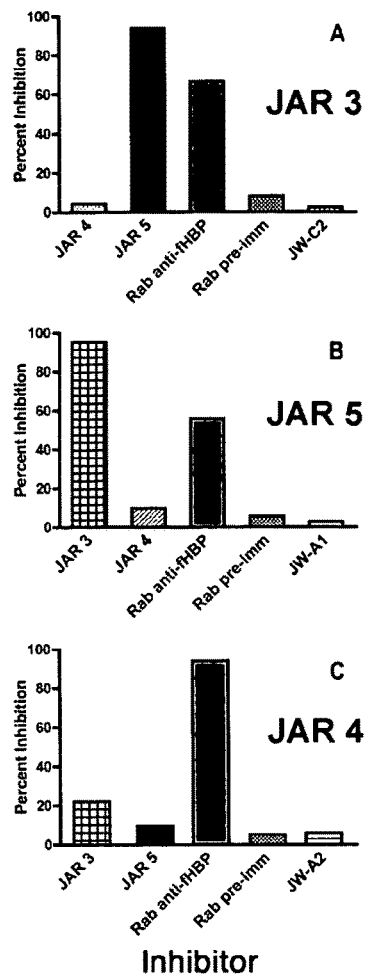
FIG. 2 is a set of graphs illustrating that binding of JAR 3 and JAR 5 mAbs to fHBP is competitive. Percent competitive inhibition of binding of anti-fHBP mAbs to fHBP by a second antibody as measured by ELISA. Each panel includes: rabbit polyclonal anti-fHBP antiserum; rabbit preimmune serum; and a negative control mAb specific for an irrelevant capsular antigen (JW-C2, -A2 or -A1). Panel A, Inhibition of binding of JAR 3 by JAR 4 or JAR 5. Panel B, Inhibition of binding of JAR 5 by JAR 3 or JAR 4. Panel C, Inhibition of binding of JAR 4 by JAR 3 or JAR 5.

The results are shown in FIG. 2. JAR 5 (5 µg/ml) inhibited binding of JAR 3 by greater than 90% (FIG. 2, Panel A) and the reciprocal reaction with JAR 3 inhibited binding of JAR 5 (FIG. 2, Panel B). In contrast, there was no detectable inhibition of binding of JAR 4 by JAR 3 (50 µg/ml) or JAR 5 (50 µg/ml) (FIG. 2C). JAR 4 also did not inhibit binding of JAR 3 (FIG. 2, Panel A) or JAR 5 (FIG. 2, Panel B). The positive control, a 1:10 dilution of rabbit anti-fHBP v.1 antiserum, inhibited binding of all three mAbs, whereas pre-immune rabbit serum and negative control mAbs gave less than 7% inhibition. Thus JAR 3 and JAR 5 recognize overlapping (or identical) epitopes, since each of these mAbs inhibited binding of the other to fHBP.

Example 2

Identification of Amino Acid Residues of fHBP Epitopes Implicated in JAR mAb Binding To investigate the epitopes defined by the remaining anti-fHBP mAbs in the panel, site-specific mutagenesis was used to create knock-outs (KO) of recombinant fHBPs. For nine of the mAbs, an fHBP KO lacking the indicated residue resulted in a significant loss of binding of the corresponding JAR mAb as measured by Western blot and/or ELISA (see Table in FIG. 29.) For seven of the mAbs, it was demonstrated that the respective mAb that was negative for binding became positive for binding after introduction of one or two of the corresponding amino acid substitutions (see Table in FIG. 29). Taken together, one or both of these strategies was successful in identifying amino acid residues involved in the reactivity of nine of the JAR mAbs (FIG. 3).

Figure 30:
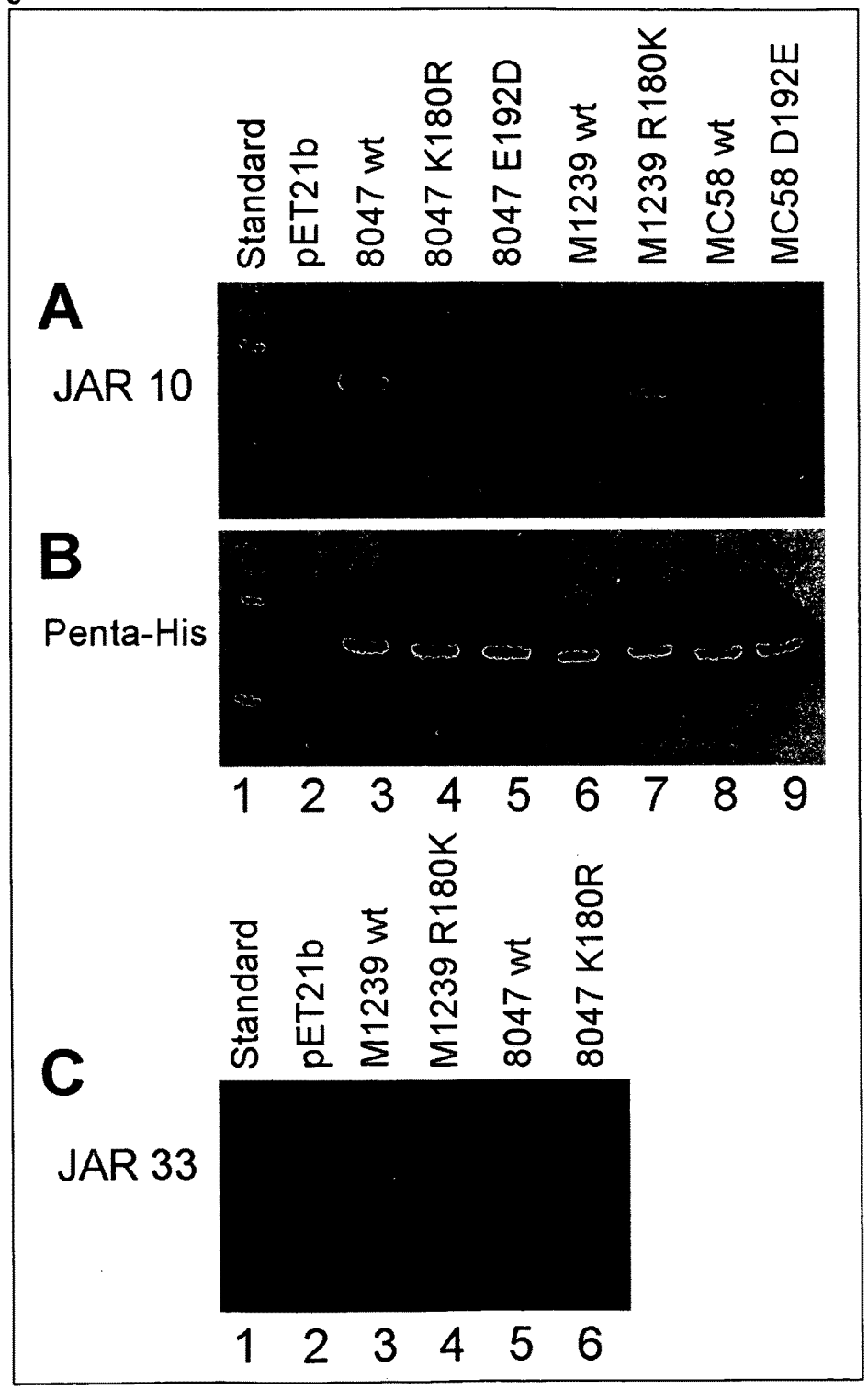
FIG. 30 provides an image of a Western blot indicating residues involved in the JAR 10 and JAR 33 epitopes. *E. coli* lysates containing plasmids expressing the respective wild-type and mutant fHBPs were analyzed by Western blot with JAR 10 (Panel A), Penta-His mAb (Panel B), or JAR 33 (Panel C).
Figure 31:
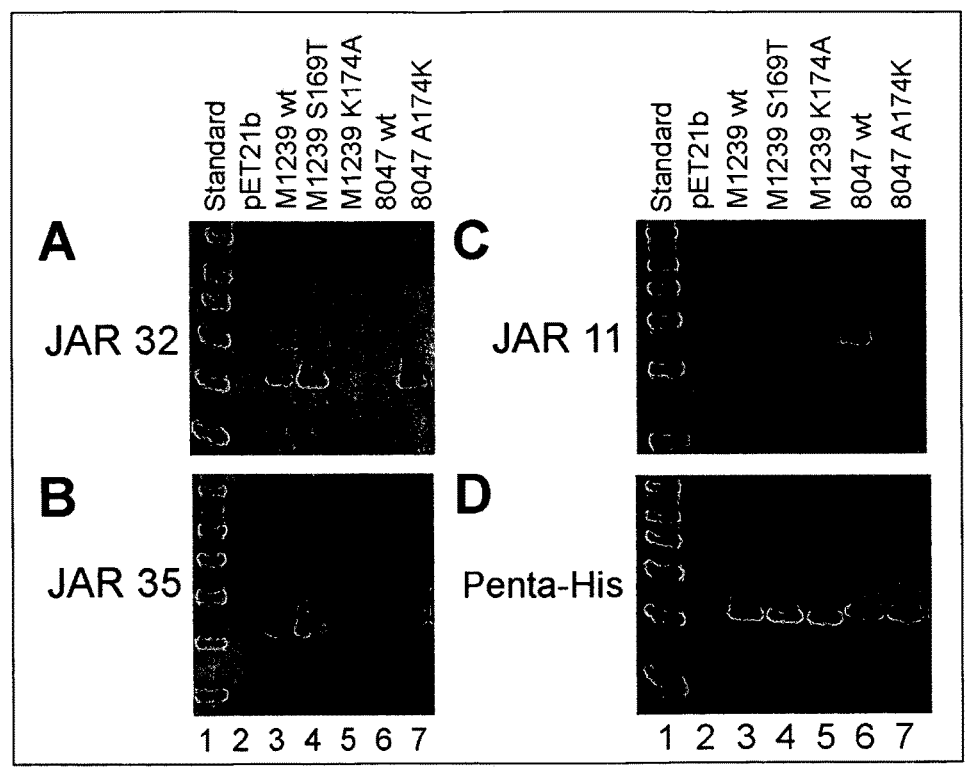
FIG. 31 provides an image of a Western blot indicating a residue involved in the JAR 11, JAR 32 and JAR 35 epitopes. *E. coli* lysates containing plasmids expressing the respective wild-type and mutant fHBPs were analyzed by Western blot with JAR 32 (Panel A), JAR 35 (Panel B), JAR 11 (Panel C) or Penta-His mAb (Panel D).
Figure 32:
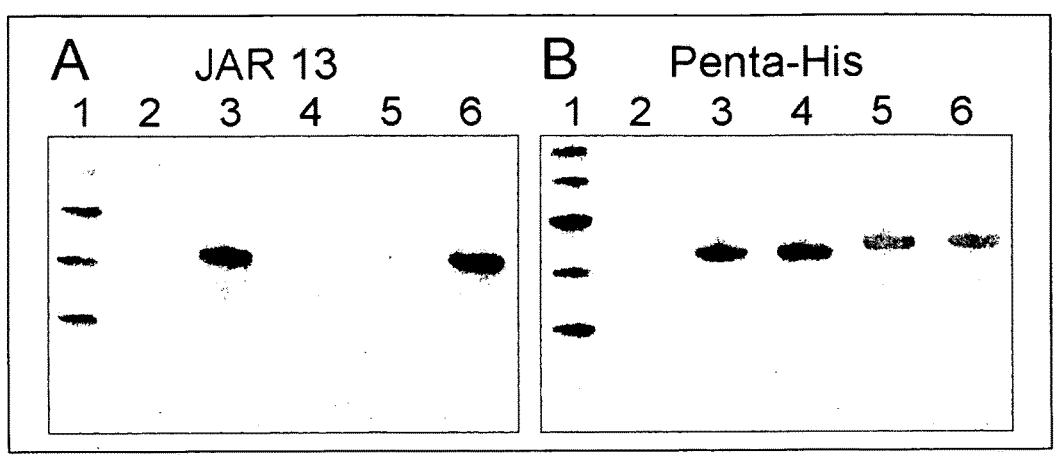
FIG. 32 provides an image of a Western blot indicating residue involved in the JAR 13 epitope. *E. coli* lysates containing plasmids expressing wild-type and mutant fHBPs: lane 1, molecular weight marker; lane 2, pET21 (empty plasmid); lane 3, fHBP(8047)wt; lane 4, fHBP(8047) S216G; lane 5, fHBP(RM1090)wt; lane 6, fHBP(RM1090) G216S. Blots were probed with JAR 13 (Panel A) or Penta-His mAb (Panel B) and anti-mouse IgG-HRP secondary antibody.

FIGS. 30-32 provide supporting data for identification of residues involved in JAR mAb binding. *E. coli* lysates containing plasmids expressing the respective wild-type and mutant fHBPs were analyzed by Western blot using the appropriate JAR mAb, as well as a control antibody to detect an epitope tag present on the fHBP (penta-His).

Specifically, FIG. 30 is a Western blot indicating residues involved in the JAR 10 and JAR 33 epitopes, in which *E. coli* lysates containing plasmids expressing the respective wild-type and mutant fHBPs were analyzed by Western blot with JAR 10 (Panel A) or Penta-His mAb (Panel B). FIG. 31 is a Western blot indicating a residue involved in the JAR 11, JAR 32 and JAR 35 epitopes, in which *E. coli* lysates containing plasmids expressing the respective wild-type and mutant fHBPs were analyzed by Western blot with JAR 32 (Panel A), JAR 35 (Panel B), JAR 11 (Panel C) or Penta-His mAb (Panel D). FIG. 32 is a Western blot indicating residue involved in the JAR 13 epitope, in which *E. coli* lysates containing plasmids expressing wild-type and mutant fHBPs were probed with JAR 13 (Panel A) or Penta-His mAb (Panel B) and anti-mouse IgG-HRP secondary antibody.

It should be noted that the numbering of the amino residues used herein is with reference to the mature protein sequence (i.e. lacking the signal) of fHBP from strain MC58 (i.e., the fHBP amino acid sequence of MC58 was used as the reference v.1 fHBP amino acid sequence). Because the total number of amino acid residues in v.2 and/or v.3 fHBPs differ from the total number of amino acid residues in v.1 fHBPs, the amino acid sequences of the v.2 protein (with fHBP from strain 8047 used as the reference v.2 amino acid sequence) and v.3 fHBP (with fHBP from strain M1239 used as the reference v.3 amino acid sequence) differ by −1 and +7 amino acid residues, respectively, from that of MC58. Thus, for example, a leucine residue (L) referred to using the numbering system herein as being at position 166 of the v.2 or v.3 fHBP sequence is actually at position 165 of the v.2 protein and at position 173 in the v.3 protein based on the actual amino acid sequence of these proteins, rather than on the numbering used herein based on the alignment of these sequences with v.1 fHBP of MC58.

In addition, the role of JAR mAb epitopes in fH binding by fHBP was investigated. FIG. 19 is a series of graphs showing the ability of representative JAR mAbs prepared against fHBP v.2 (8047), v.3 (MI239), or v.1 (MC58) recombinant proteins to give concentration-dependent inhibition of binding of fH to rfHBP v.2 (Panel A), rfHBP v.3 (Panel B), or rfHBP v.1 (Panel C) in an ELISA. These data show that some of the contact residues defined by the JAR mAb epitopes are involved in binding to fH. These data thus argue for possible inclusion or preservation of JAR mAb epitopes that are involved in fH binding since blocking of binding of fH to *N. meningitidis* can provide a further mechanism of protection.

Example 3

Production of Chimeric fHBP Containing v.1 and v.2 Epitopes

As noted above, the epitopes defined by JAR 3 and JAR 5, are located within the B domain of variant 1 fHBP beginning approximately 19 amino acid residues N-terminal to the start of α-helix AH2, or approximately 15 amino acid residues N-terminal to the amino acid sequence of GEHT (SEQ ID NO:7). A first chimeric fHBP (referred to herein as "Chimera I") was constructed by combining a portion of the gene encoding the A domain and the N-terminal portion of the B domain up to residue G136 from v.1 fHBP of MC58 with the distal portion of the gene encoding the alpha-helix of the B domain and C domain of v.2 fHBP from strain 8047. The residue at position G136 was used as a convenient crossover position (the point at which the chimeric sequence "shifted" from that of the v.1 fHBP to that of the v.2 fHBP). G136 is N-terminal the α-helix AH2 and begins a sequence of four highly conserved residues, GEHT (SEQ ID NO:7), which are shown in a box in FIG. 4. The outer brackets show the region of the protein previously defined as the B domain (Giuliani et al. Infect Immun 2005; 73:1151-60).

A second chimeric fHBP, referred to herein as Chimera II, was generated. Chimera II was identical in amino acid sequence to Chimera I except for the introduction the A174K substitution (Bold and underlined K, Chimera II, FIG. 4). It should be noted that the A domain is not shown in FIG. 4, or in the NMR-based structure of FIG. 5, but would be attached at the N-terminus labeled "N" in FIG. 5.

Figure 5:
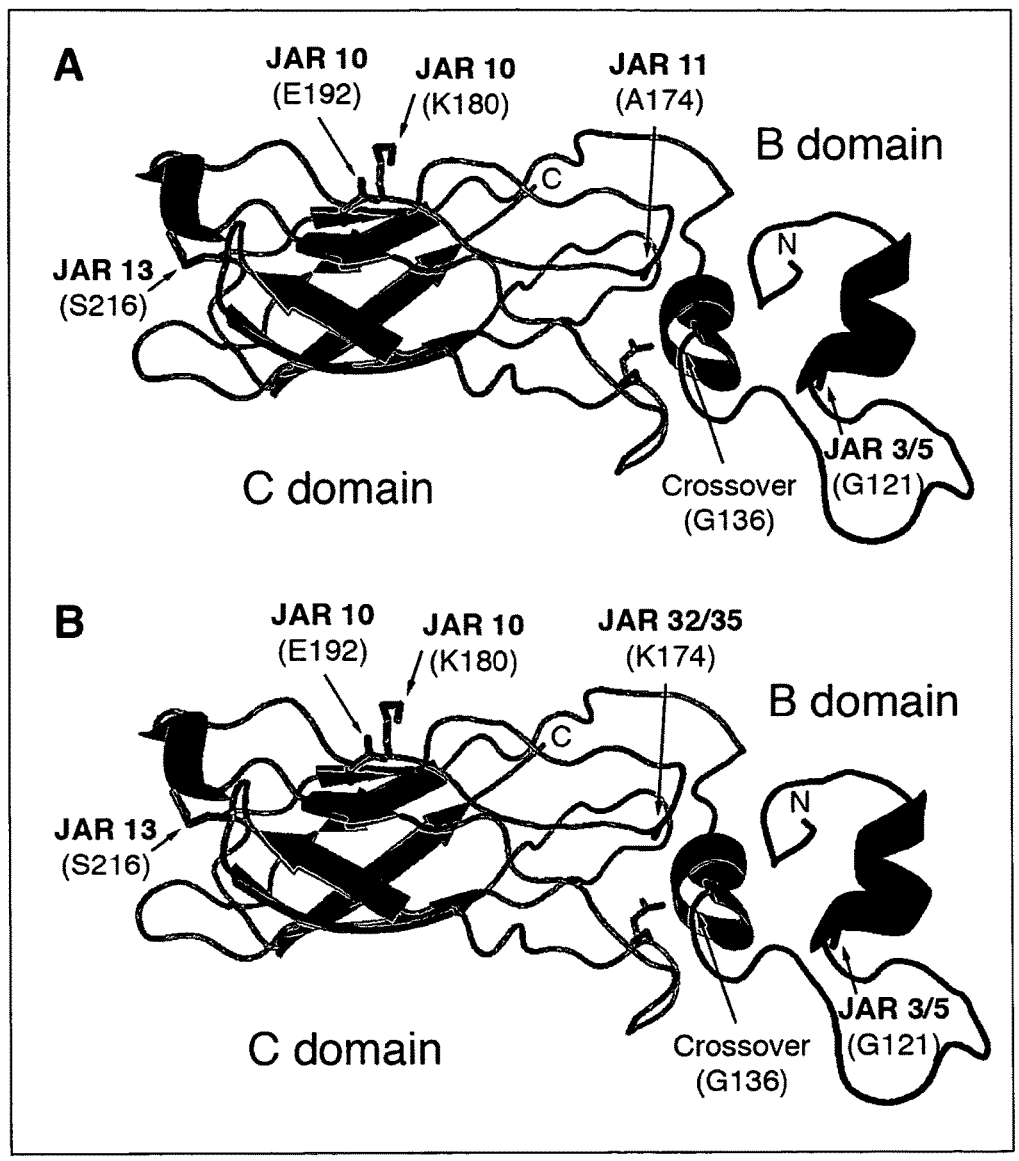
FIGS. 5A and 5B provide schematic representations of chimeric fHBPs. The N-terminal portion of the B domain from the v.1 fHBP is on the right, and the C-terminal portion of the B domain encompassing the α-helix of the v.2 protein together with the C domain of the v. 2 fHBP is on the left. The junction point for these chimeras, exemplified by G136 is indicated with an arrow and accompanying text. Both chimeric proteins express the JAR 3 and JAR 5 epitopes expressed on the B domain of fHBP v.1 and the JAR 10 epitope, which is on the C domain of subsets of strains expressing v.1, v.2 or v.3 fHBP Chimera I contains the JAR 11 epitope, including residue A174 (Panel A), which is expressed on the C domains of a subset of strains expressing fHBP v.2 or v.3. Chimera II contains the JAR 32/JAR 35 epitopes, including residue K174, which are expressed on the C domains of subsets of strains expressing fHBP v.2 or v.3. A domains are not shown in these representations. The model was constructed based on the NMR structure of Cantini et al. (2006) J Biol Chem 281:7220-7.

Models of the two chimera vaccines are shown in FIG. 5, Panels A and B. Chimera I contains the JAR 11 epitope, including residue A174 (FIG. 5, Panel A). Chimera II contains the JAR 32 and JAR 35 epitopes, including residue K174 (FIG. 5, Panel B). The model of the fHBP chimeras was constructed based on the NMR structure of Cantini et al. J Biol Chem 2006; 281:7220-7.

Example 4

Purification and Characterization of Mutant Proteins

Recombinant proteins were expressed in E. coli as C-terminal hexahistidine (His$_6$) fusions, which were purified by metal chelate chromatography. Specifically, Proteins were expressed from pET21-based plasmids in E. coli BL21 (DE3) as C-terminal hexa-histidine fusions. Fusion proteins were then isolated by metal chelate chromatography according to methods known in the art. Isolated proteins were dialyzed against 1×PBS, 5% sucrose, 1 mM DTT and filter sterilized. Proteins (5 μg each) were separated on a 4-12% polyacrylamide gel and stained with Coomassie blue.

Figure 6:
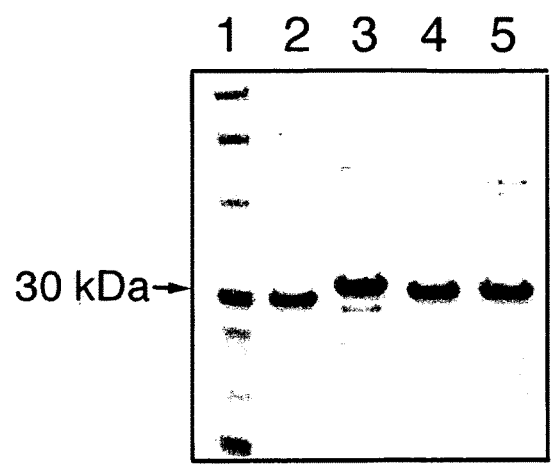
FIG. 6 provides the results of SDS-PAGE analysis of purified wild-type and mutant fHBPs. Proteins were expressed from pET21-based plasmids in *E. coli* BL21 (DE3) as C-terminal hexa-histidine fusions and purified by metal chelate chromatography. Proteins were dialyzed against 1×PBS, 5% sucrose, 1 mM DTT and filter sterilized. Proteins (5 μg each) were separated on a 4-12% polyacrylamide gel and stained with Coomassie blue. Lane 1, mass standard; 2, fHBP v.1 (MC58); 3, fHBP v.2 (8047); 4, fHBP Chimera I; 5, fHBP Chimera II.

The results are shown in FIG. 6. Lane 1, mass standard; 2, fHBP v.1 (MC58); 3, fHBP v.2 (8047); 4, fHBP Chimera I; 5, fHBP Chimera II.

Example 5

Epitope Expression by Chimeric Antigens

Figure 7:
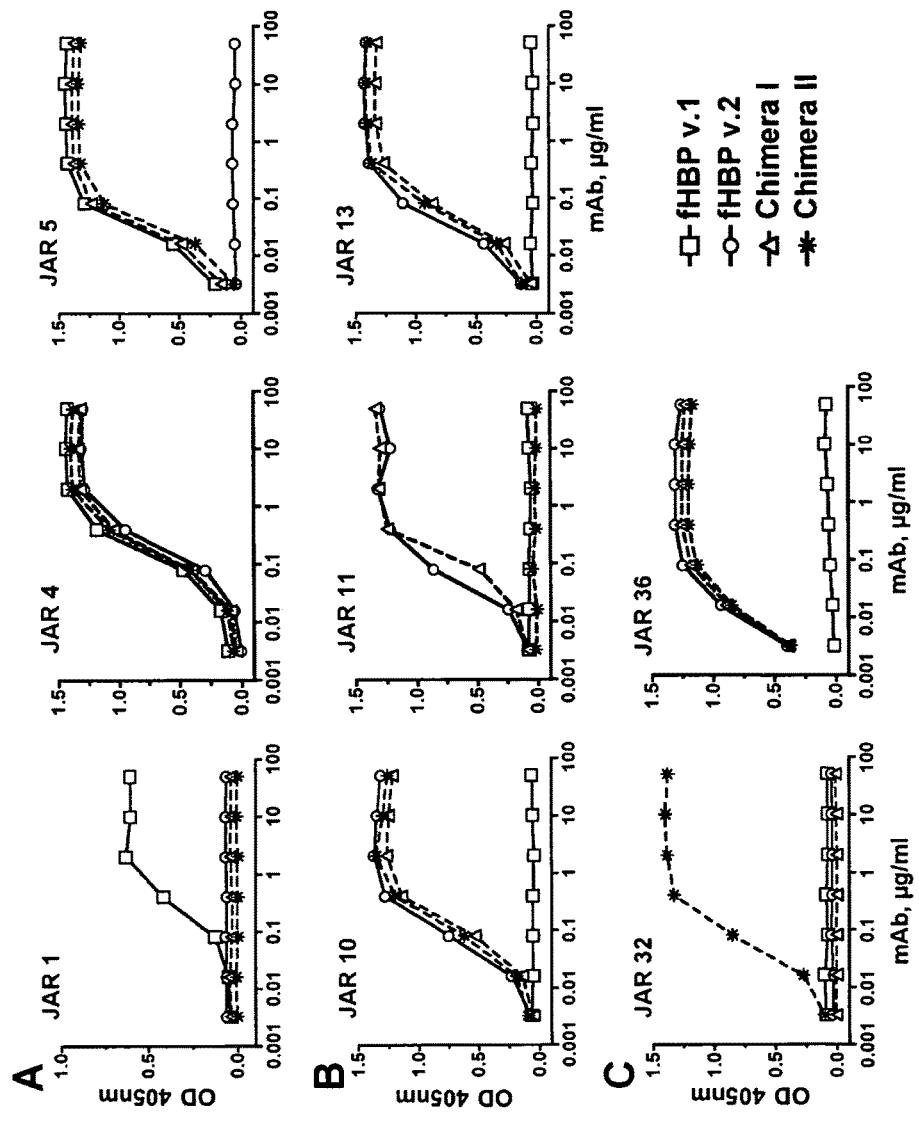
FIG. 7 is a set of graphs illustrating binding of individual anti-fHBP mAbs to recombinant proteins. Panel A shows mAbs prepared against fHBP v.1; Panel B, fHBP v.2; Panel C, fHBP v.3. The symbols represent different antigens on the plate: open squares, fHBP v.1; open circles, fHBP v.2; open triangles, Chimera I; asterisks, Chimera II.

ELISA was used to assess concentration-dependent binding of the anti-fHBP mAbs to the chimeric antigens isolated in Example 4. As expected, JAR 1, which binds to a v.1 epitope in the C domain (R204), did not bind to either of the chimeric proteins (FIG. 7, Panel A). JAR 5, which is specific for an epitope on the B domain of fHBP v.1, and JAR 4, which cross-reacts with an epitope that is not yet defined by expressed by v.1 and v.2, showed identical respective concentration-dependent binding with the two chimeric proteins as compared with the respective wild-type v.1 and/or v.2 proteins.

FIG. 7, Panel B, provides binding data for mAbs JAR 10, 11 and 13, which were from a mouse immunized with v.2 or fHBP. All three mAbs recognize epitopes on the C domain of fHBP v.2 of strain 8047 (FIG. 20), and they showed similar respective concentration-dependent binding with the Chimera I protein as they did with the wild-type rfHBP v.2 control protein expressed from the gene of strain 8047 (FIG. 7, Panel B). As expected, JAR 11 did not bind to Chimera II, since this protein had lysine substituted for alanine at position 174 (A174K), which eliminated the JAR 11 epitope and introduced the JAR 32 epitope (Panel C). JAR 36, which cross-reacts with an epitope not yet defined but present on fHBP v.2 and v.3 fHBP bound to both of the chimeric proteins, and to the wild-type rfHBP v.2 control but not with the fHBP v.1 control (FIG. 7, Panel C). Collectively, the data showed that the two chimeric fHBPs expressed epitopes associated with fHBP v.1, v.2, and/or v.3 proteins, and reacted as expected with the various mAbs in accordance with our studies localizing the epitopes.

Example 6

Immunization of Mice With Double Mutant and Chimeric fHBPs and Bactericidal Antibody Responses The proteins shown in FIG. 6 were used to immunize mice according to the schedule in Table 1, below. Four doses of vaccine (20 μg of protein) were administered IP with intervals of 2 weeks between doses. Mice were bled 2.5 weeks after dose 4. CFA=complete Freund's adjuvant; IFA=incomplete Freund's adjuvant; Al(OH)$_3$=aluminum hydroxide. CFA/IFA below indicates that the mice received an initial dose with CFA, then subsequent booster doses with IFA. Where Al(OH)$_3$ was used as the adjuvant, all doses were administered with aluminum hydroxide as the adjuvant.

TABLE 1

| Immunization schedule[1] | | |
|---|---|---|
| Group | fHBP Protein | Adjuvant |
| 1 | — | CFA/IFA |
| 2 | fHBP v.1 | CFA/IFA |
| 3 | fHBP v.2 | CFA/IFA |
| 4 | Chimera I | CFA/IFA |
| 5 | Chimera II | CFA/IFA |
| 6 | — | Al(OH)$_3$ |
| 7 | fHBP v.1 | Al(OH)$_3$ |
| 8 | fHBP v.2 | Al(OH)$_3$ |
| 9 | Chimera I | Al(OH)$_3$ |
| 10 | Chimera II | Al(OH)$_3$ |

Figure 9:
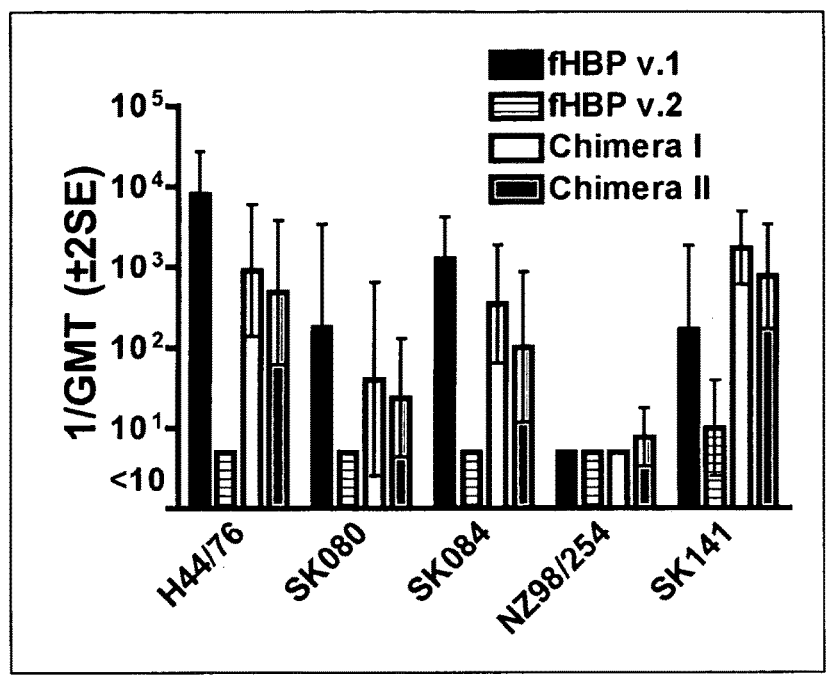
FIG. 9 is a graph illustrating serum bactericidal antibody responses of mice immunized with chimeric recombinant proteins given with Freund's adjuvant as measured against *N. meningitidis* group B strains expressing fHBP in the antigenic v.1 group. Strain H44/76 expresses fHBP v.1 identical to that of the fHBP v.1 control vaccine. The remaining strains express subvariants of fHBP v.1 (See Table in FIG. 8A, above). Values are presented as 1/GMT (Reciprocal (or inverse) geometric mean titer) with a 95% confidence interval.

[1]Groups 1 to 10 consist of 5 CD-1 mice each (N = 60). Each animal received four injections FIG. 9 summarizes the serum antibody responses of the mice that received the chimeric vaccines administered with FA when measured against strain H44/76 (variant 1) and four additional strains that express subvariants of v.1 fHBP (i.e., fHBP proteins with relatively small amino acid differences (e.g., with greater than about 88%, and less than 97% amino acid sequence identity) between the sequence of the respective protein and that of v.1.1 fHBP of H44/76). The mice immunized with the wild-type rfHBP v.1 control protein had high responses to H44/76 (reciprocal GMT of nearly 10,000) and lower and variable responses against the other four test strains (ranging from a GMT of <1:10 against strain NZ98/254 to a GMT of >1:1,000 against SK084). The sera from the mice immunized with the rfHBP v.2 control protein were either negative for bactericidal activity (bactericidal titers <1:10, four strains) or weakly positive (reciprocal GMT of 1:10; strain SK141). The mice immunized with either chimeric protein vaccine developed serum bactericidal antibodies against all four strains that were susceptible to bactericidal activity of sera from the control mice immunized with rfHBP v.1. For three of the four strains, the respective reciprocal GMTs of the chimeric vaccine groups were ~1 log lower than those of mice given the control rfHBP v.1 vaccine whereas the responses to the fifth strain, SK141, were as high or higher than those of the mice given the control rfHBP v.1 vaccine.

Figure 10:
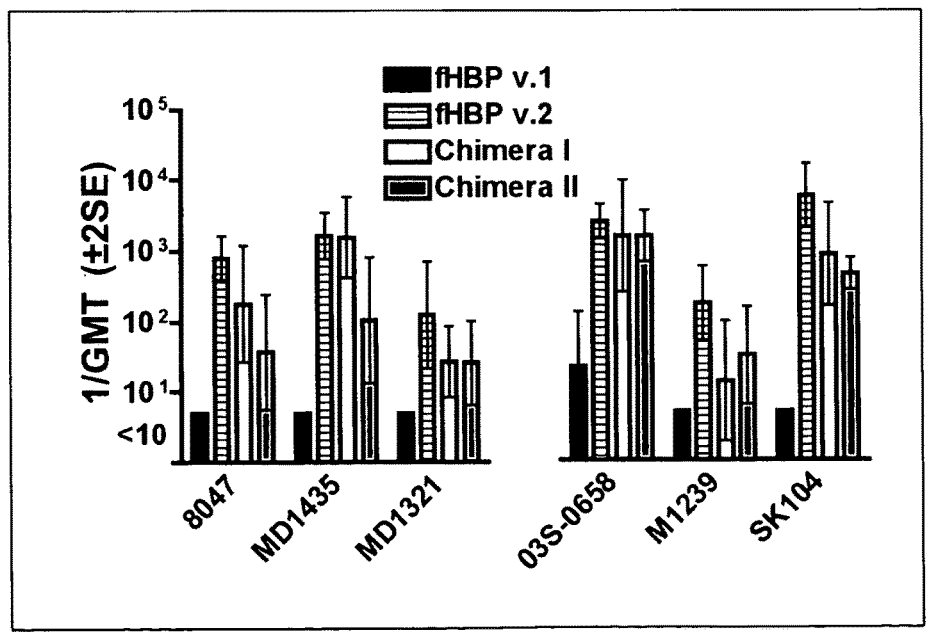
FIG. 10 is a graph illustrating serum bactericidal antibody responses of mice immunized with chimeric recombinant proteins given with Freund's adjuvant as measured against *N. meningitidis* group B expressing fHBP in the v.2 or v.3 antigenic groups. Strain 8047 expresses fHBP v.2 identical to that of control rfHBP v.2 vaccine. The remaining strains express subvariants of fHBP v.2 or v.3 (see Table in FIG. 8A). Values are presented as 1/GMT with a 95% confidence interval. The data are stratified based on strains reacting with JAR 11 (left panel) or JAR 32 (right panel). The Chimera I and II vaccines are identical except that Chimera I has residue A174 and is JAR 11-positive and JAR 32-negative, whereas Chimera II has residue K174 and is JAR 11-negative and JAR 32-positive. See figure for bar symbols.

FIG. 10 summarizes the serum bactericidal antibody responses as measured against the six strains expressing fHBPs in the v.2 or v.3 variant groups. Three of the strains were JAR 11 positive (left panel) and three were JAR 32 positive (right panel). Sera from control mice immunized with rfHBP v.2 were bactericidal against all six strains whereas, with one exception (strain 03S-0658), the serum bactericidal titers of control mice immunized with rfHBP v.1 were <1:10. The sera from the mice immunized with either chimeric vaccine were bactericidal against all six strains. For four of the strains (8047, MD1321, M1239 and SK104), the respective titers were ~1 log lower than those of the control mice immunized with rfHBP v.2. For the remaining two strains, 03S-0658 and MD1435) the titers elicited by one or both chimeric vaccines were similar to those of the mice given the positive control rfHBP v.2 vaccine. Thus, in contrast to the control rfHBP v.1 or v.2 vaccines, the chimeric vaccines elicited bactericidal antibody responses against strains expressing fHBP from each of the three antigenic variant groups.

The Chimera I vaccine expressed the JAR 11 epitope while the Chimera II vaccine expressed the JAR 32 epitope (FIG. 1). However, with one exception, the respective responses of mice immunized with either chimeric vaccine when measured against strains expressing JAR 11- or JAR 32-positive fHBP were not significantly different from each other (FIG. 5). The exception was the JAR 11-positive strain MD1435, where there was a trend for a higher reciprocal GMT in the group of mice immunized with Chimera I than Chimera II (P=0.06).

Thus, the A174K substitution in Chimera II that eliminated the JAR 11 epitope (v.2) and introduced the JAR 32/35 epitope (v.3) did not appreciably increase the bactericidal responses against a test strain expressing the v.3 protein.

Figure 11:
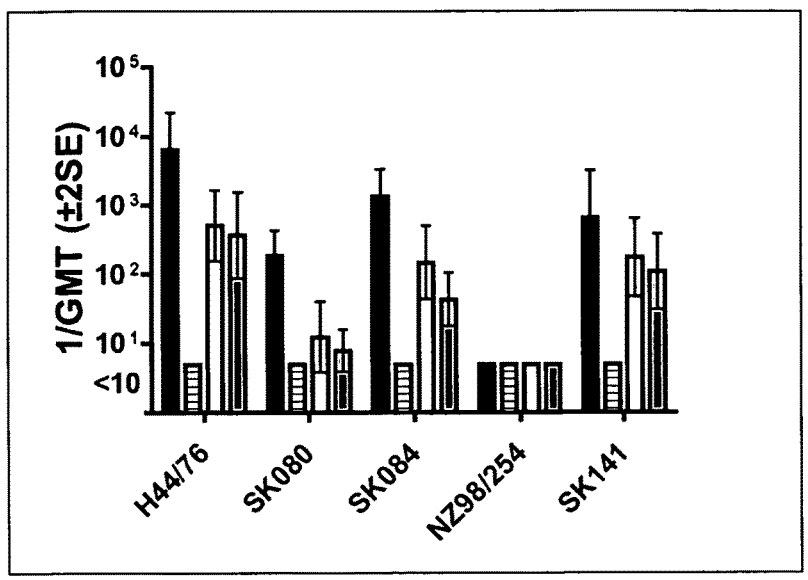
FIG. 11 is a graph illustrating serum bactericidal antibody responses of mice immunized with chimeric recombinant proteins adsorbed to aluminum hydroxide as measured against *N. meningitidis* group B strains expressing fHBP in the antigenic v.1 group. Strain H44/76 expresses fHBP v.1 identical to that of the fHBP v.1 control vaccine. The remaining strains express subvariants of fHBP v.1. Values are presented as 1/GMT (i.e., reciprocal (or inverse) geometric mean titer) with a 95% confidence interval. Bar symbols for each vaccine are as shown in FIG. 10.
Figure 12:
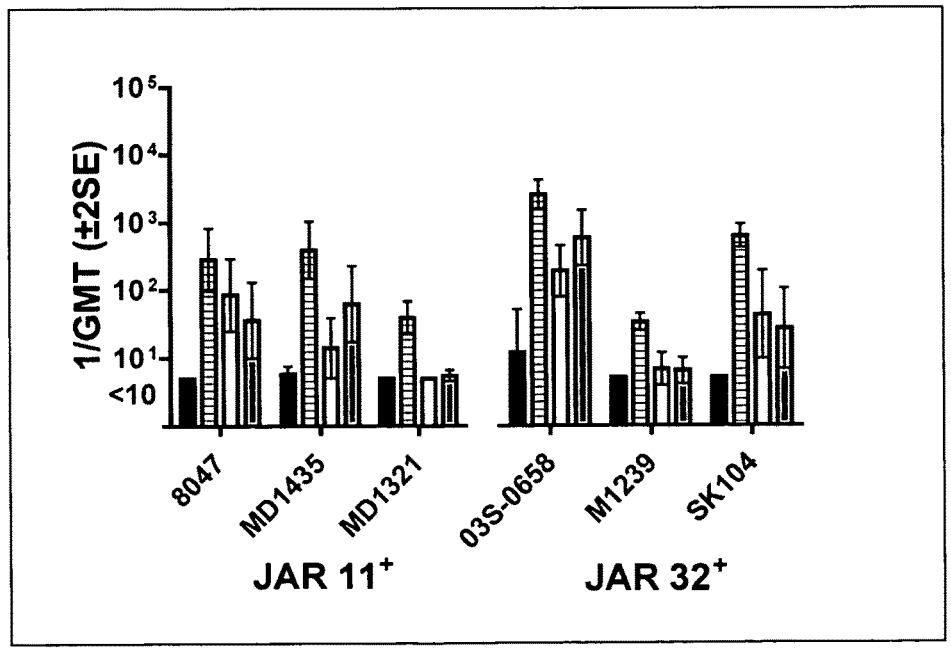
FIG. 12 is a graph illustrating serum bactericidal antibody responses of mice immunized with chimeric recombinant proteins adsorbed to aluminum hydroxide as measured against *N. meningitidis* group B expressing fHBP in the v.2 or v.3 antigenic groups. Strain 8047 expresses fHBP v.2 identical to that of control rfHBP v.2 vaccine. The remaining strains express subvariants of fHBP v.2 or v.3 (see Table in FIG. 8). Values are presented as 1/GMT with a 95% confidence interval. The data are stratified based on strains reacting with JAR 11 (left panel) or JAR 32 (right panel). The Chimera I and II vaccines are identical except that Chimera I is JAR 11-positive and JAR 32-negative, whereas Chimera II is JAR 11-negative and JAR 32-positive Bar symbols for each vaccine are as shown in FIG. 10.

FIG. 11 summarizes the serum bactericidal antibody responses of mice immunized with the chimeric vaccines when absorbed with aluminum hydroxide as measured against the panel of test strains with v.1 fHBP. The corresponding data for responses to test strains expressing v.2 or v.3 fHBP are shown in FIG. 12. In general the respective responses to the different vaccines absorbed with aluminum hydroxide paralleled those observed to the vaccines given with Freund's adjuvant although as expected the titers were somewhat lower with the aluminum hydroxide adjuvant.

The data above indicate that the JAR3/5 epitope, which is common to virtually all v.1 proteins but is not present in fHBP from v.2 or v.3 strains, is important for eliciting high bactericidal antibody titers to the variant 1 fHBP protein. This discovery that the epitope recognized by JAR 3/5 plays an important role in eliciting v.1 fHBP bactericidal antibodies provides the basis for the rational design of further chimeric fHBP vaccines that can elicit bactericidal antibodies across strains expressing different fHBP protein variants, particularly against both v.1 and v.2 fHBP-expressing strains. For example, the two chimeric vaccines described above (Chimera I and Chimera II) included, from N-terminus to C-terminus:

1) an A domain (common to both v.1 and v.2);
2) a heterologous B domain composed of, from N-terminus to C-terminus,
   a) a contiguous amino acid sequence of an N-terminal portion of a B domain of a v.1 fHBP containing the amino acid sequence defining the JAR 3/5 epitope, operably linked to
   b) a contiguous amino acid sequence defining the remainder of the B domain, which amino acid sequence is that of a B domain of a v.2 fHBP, where the v.2 fHBP amino acid sequence is present in the heterologous B domain following the amino acid sequence of GEHT (SEQ ID NO:7); and
3) a C domain of the v.2 protein.

Example 8

Natural or Synthetic Polymorphisms of v.1 fHBP B Domains

As noted above, the discovery that the JAR 3/5 epitope in the N-terminal portion of v.1 fHBP provides the basis for construction of additional chimeric fHBP polypeptides that can serve as vaccines to elicit cross-reactive, bactericidal antibodies against v.1 fHBP-expressing *N. meningitidis* strains and v.2 fHBP-expressing *N. meningitidis* strains. In order to provide guidance as to the amino acid sequences of v.1 fHBP that find use in the fHBP chimeric vaccines contemplated here, various v.1 fHBP amino acid sequences of the B domain were analyzed.

FIG. 13 provides an alignment of fHBP v.1 sequences with natural polymorphisms in the N-terminal portion of the B domain. The sequence conservation is shown below the alignment, with "*" denoting residues that are identical, ":" denoting residues that are conserved, and "." denoting residues that are semi-conserved across the aligned sequences. The positions of alpha-helices are shown above the alignment, with the residues implicated in the alpha helices indicated by italics. The residue, G121, which is implicated in the JAR 3 and JAR 5 epitope, is shown in bold and underlining. A lysine at position 122 (K122) also appears to be important in the JAR 3/5 epitope, since one strain that is negative for JAR 3 and JAR 5 binding, 03S-0408, has G121 but differs from JAR 3/5 reactive strains in having serine at position 122 (S122). (data not shown) The amino acid sequence of GEHT (SEQ ID NO:7) that provides the point at which the B domain sequence of the chimera "switches" or "crosses over" to the amino acid sequence of a v.2 B domain in Chimera I and Chimera II (referred to herein as the "junction point") is shown in the box.

As shown in FIG. 13, there are a number of natural polymorphisms in the region of G121, which is involved in the JAR 3/JAR 5 epitope. Notably, a fHBP containing R121 (rather than G121) does not express the JAR 3/JAR 5 epitope. However, polymorphisms near G121, for example P117 in NZ98/254 and D121 in 4243, do not interfere with the binding of JAR 3 or JAR 5. Thus, some modifications at residues other than G121 provide for JAR 3/5 epitope expression.

The alignment thus provides guidance as to the types of amino acid substitutions that can be introduced while maintaining JAR 3/5 epitope expression. Such amino acid substitutions can be either naturally-occurring (i.e., natural polymorphisms) or can be introduced by synthetic means (e.g., recombinant polymorphisms). Thus, the heterologous B domains of the chimeric fHBP polypeptides contemplated herein include those containing v.1 B domain sequences with natural and synthetic polymorphisms in the proximal B domain, including both natural and synthetic variants.

Example 9

Natural or Synthetic Polymorphisms of fHBP C Domains

In addition, to the JAR 3/5 epitope, chimeric fHBPs contemplated herein generally include one or more epitopes of v.2 fHBP B and C domains, where the v.2 fHBP B domain epitopes are present at a location C-terminal to (i.e., distal to) the location of the JAR 3/5 epitope of v.1 fHBPs, which is generally C-terminal to the alpha helix that follows the sequence of GEHT (SEQ ID NO:7), which is shared between v.1 and v.2 fHBPs. In order to provide guidance as to the amino acid sequences of v.2 fHBP that find use in the fHBP chimeric vaccines contemplated here, various v.2 fHBP amino acid sequences of the B domain, as well as the C domain were analyzed.

FIG. 14 provides an alignment of exemplary v.2 fHBP sequences of the distal portion of the B domain, and further provides exemplary v.2 fHBP sequences of the C domain, where the B domain is generally defined as residues 101 to 164, with numbering based on MC58 fHBP as a reference.

Therefore, based on the polymorphic variants shown in FIGS. 13 and 14, variations in the amino acid sequence of v.2 fHBP B domains and C domains, as well as additional combinations of v.1/v.2 heterologous B domains with different v.2 C domains to can be readily envisioned to generate additional chimeric fHBPs. FIGS. 13 and 14 provide 7 exemplary amino acid sequences of the N-terminal region of the v.1 B domain (FIG. 10) and 9 exemplary amino acid sequences for the distal portion of the B domain of v.2 fHBP and for the C domain of v.2 fHBP (FIG. 11). Thus, the sequences in FIGS. 13 and 14 provide for a least 63 different fHBP chimeras, simply by combining the amino acid sequences as provided. Further, the alignments provide guidance as to the amino acid residues that can be substituted.

Thus, not only do these exemplary sequences provide guidance for use of amino acid sequences containing naturally-occurring polymorphisms, they also provide guidance for production of synthetically-generated variants (e.g., using recombinant methods). For example, additional point mutations may be introduced into the coding nucleic acid to provide for fHBP chimeras that express other desirable epitopes, such as the v.1 epitope recognized by JAR 1/mAb 502 that is in the portion of the C domain (R204), or the JAR 11 epitope in Chimeras IV and V. Introduction of the JAR1/mAb 502 epitope can provide for improved cross-reactivity against v.1 strains from the ST-32 lineage that nearly always express the JAR 1 epitope, while eliciting antibodies to the JAR 11 epitope can provide for improved titers against v.2 strains (see Koeberling et al., J Infect Dis 2008, 198:262-270, for a description of v.1.1).

Note also, that despite engineering expression of the JAR 11 epitope in Chimera I, and the JAR 32 epitope in Chimera II, no statistically significant differences were observed in the respective serum bactericidal antibody responses of mice immunized either vaccine against strains expressing v.2 or v.3 fHBP that were JAR 11-positive or JAR 32-positive. However, the discovery that binding of antibody to an epitope located near residue 174 (i.e., JAR 11 in some strains, and JAR 32 in others; see FIG. 3) was not sufficient to elicit complement-mediated bactericidal activity in the absence of eliciting additional antibodies that bind to a second epitope associated with ion pair at residues 180 and 192 (such as JAR 10 in some strains or JAR 33 in others (Table in FIG. 20) indicates that coverage can be improved against JAR 32-positive strains by engineering expression of a second epitope defined by binding with JAR 33 (i.e., R180/E192). Note that among wild-type strains expressing fHBP v.2 or v.3, expression of JAR 32 is often associated with expression of JAR 33, while expression of JAR 11 is usually associated with expression of JAR 10 (see, for example, strain panel, FIG. 8).

Example 10

Further Exemplary Chimeric Vaccines

Figures 15, 16:
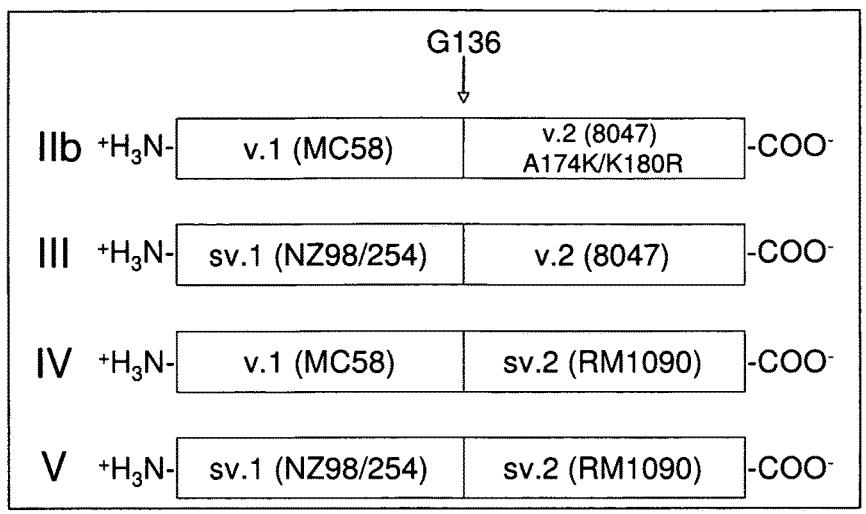
FIG. 15 is a schematic illustrating additional exemplary chimeric vaccines (Chimeras IIb, III, IV, and V). Chimera IIb can be made by introducing the K180R substitution into Chimera II Chimeras III and V can be made using portions of the A and B domains of strain NZ98/254 (subvariant v.1) with the distal portion of the B domain and C domain of v.2 strain 8047 (Chimera III) or of subvariant v.2 strain RM1090 (Chimera V). Chimera IV uses the A and proximal B domains of MC58 with the distal B and C domains of RM1090.
FIG. 16 is a schematic showing an alignment of amino acid sequences of further exemplary chimeric fHBPs (Chimera III, IV and V, SEQ ID NO:25-27) in the region of the crossover position, which is indicated by the box (residues GEHT, SEQ ID NO:7). The residues, G121 and K122, implicated in the JAR 3 and JAR 5 epitopes are shown in bold and underlining.

Table 2 and FIGS. 15 and 16 provide for additional hypothetical chimeric vaccines, designated Chimera III, Chimera IV and Chimera V. Each of these chimeric fHBPs are generated using a strategy similar to that used to generate Chimera I to provide for a chimeric fHBP that elicits bactericidal anti-v.1 and v.2 antibodies.

As illustrated in FIG. 15, Chimera III contains the A domain and proximal B domain of subvariant v.1.10 encoded by the fHBP from NZ98/254, and uses the same distal B domain and C domain of Chimera I and Chimera II.

Chimera IV, illustrated in FIG. 15, includes the A and proximal B domains of Chimera I and Chimera II, but substitutes the distal B and C domains of v.2 from strain 8047 (v.2.1) of these chimera with those from RM1090 (v.2 subvariant).

Chimera V fuses the A and proximal B domains of a v.1 subvariant (strain NZ98/254) with that distal B and C domains of v.2 subvariant (strain RM1090).

The amino acid changes that will result in the respective Chimera III, IV and V vaccine antigens, as compared with the respective amino acid sequences of the A and proximal B domain of MC58 and distal B and C domains of 8047 used to prepare Chimera 1 are shown in FIG. 16. Chimeras III and V can provide for increased breadth of protection against certain strains expressing subvariants of v.1, such as NZ98/254, which is not covered by the Chimera I or II vaccines Chimeras IV and V can provide for extended protection against v.3 strains, which are poorly covered by Chimera I or Chimera II.

Table 2 provides a summary of the observed epitope expression for Chimera I and Chimera II, and further sets out the predicted epitope expression for proposed Chimeras III, IV, and V.

TABLE 2

Predicted (or observed) epitope expression by chimeric proteins

| | Variant 1 | | Variant 1/2/3 | | Variant 2/3 | | |
|---|---|---|---|---|---|---|---|
| | | | mAb | | | | |
| mAb | mAb 502/ JAR1 | JAR 3/5 | JAR 10 | JAR 11 | JAR 13 | JAR 32/35 | JAR 33 |
| | | | | Domain | | | |
| | C | B | C | C | C | C | C |
| | | | | Epitope | | | |
| | R204 | G121 | K180 and E192 | A174 | S216 | K174 | R180, E192 |
| Wild-type proteins | | | | | | | |
| MC58 (v.1) | 1 | 1 | 0 | 0 | 0 | 0 | 0 |
| NZ98/254 (v.1, sv) | 0 | 1 | 1 | 0 | 0 | 0 | 0 |
| 8047 (v.2) | 0 | 0 | 1 | 1 | 1 | 0 | 0 |
| RM1090 (v.2, sv) | 0 | 0 | 0 | 0 | 0 | 1 | 1 |
| Chimeric proteins | | | | | | | |
| Chimera I | 0 | 1 | 1 | 1 | 1 | 0 | 0 |
| Chimera II | 0 | 1 | 1 | 0 | 1 | 1 | 0 |
| Proposed Chimerae | | | | | | | |
| Chimera III | 0 | 1 | 1 | 1 | 1 | 0 | 0 |
| Chimera IV | 0 | 1 | 0 | 0 | 0 | 1 | 1 |
| Chimera V | 0 | 1 | 0 | 0 | 0 | 1 | 1 |

1 = presence of epitope;
0 = absence of epitope;
sv, subvariant.
mAb 502 was described by Giuliani et al (Infect Immun 2005; 73: 1151-60). JAR 3 and 5, were prepared against a v.1 fHBP (gene from strain MC58) (Welsch et al J Immunol 2004; 172: 5606-15). JAR 10, 11 and 13, were prepared against a v.2 protein (gene from strain 2996) (Beernink et al. J Infect Dis 2007; 195: 1472-9), and JAR 32, 33 and 35 were prepared against a v.3 protein (gene from strain M1239). Each of the mAbs reacts with the variant protein, which was used to immunize the mouse. Some of the mAbs also cross-react with subsets of proteins from other variant groups.
Chimeras I and II were constructed to contain amino acid residues 1 to 135 encoded by fHBP gene v.1.1 (MC58) fused with residues 136 to 255 of v.2.1 gene from 8047. Chimera II also contains a point mutation A174K introduced into the C domain that inactivates the epitope recognized by JAR 11 and introduces the epitope recognized by JAR 32/35. Proposed Chimeras III, IV and V are examples of additional chimeric fHBPs, with predicted epitope expression as defined by binding of the respective JAR mAbs shown.

Further modifications of the chimeric fHBP include varying the residue within the heterologous B domain at which the v.1 fHBP B domain sequence ends and the v.2 (or v.2) fHBP B domain sequence ends. Specifically, although residue G136 was used as the position of the "crossover" between fHBP variants, the "crossover" residue can be any residue C-terminal of the amino acid sequence defining the JAR 3/JAR 5 epitope and a residue within M123-S136 can also be selected. In addition, residue positions C-terminal to G136 (E137-D142), or residue positions adjacent or within α-helix AH2 (K143-A150, preceding the first beta-strand) can be suitable crossover residue positions. Therefore, a number of different crossover residue positions are contemplated herein, where the crossover residue may be positioned after G121 of the JAR 3/5 epitope (G121) through and including A174 of the JAR 11 epitope, where the presence of the JAR 3/5 epitope can be assessed using immunoassay methods known in the art, (Note that numbering above is based on the amino acid sequence number of the fHBP reference sequence of MC58.)

Example 11

Expression of Chimeric fHBP in N. meningitidis

Figure 33:
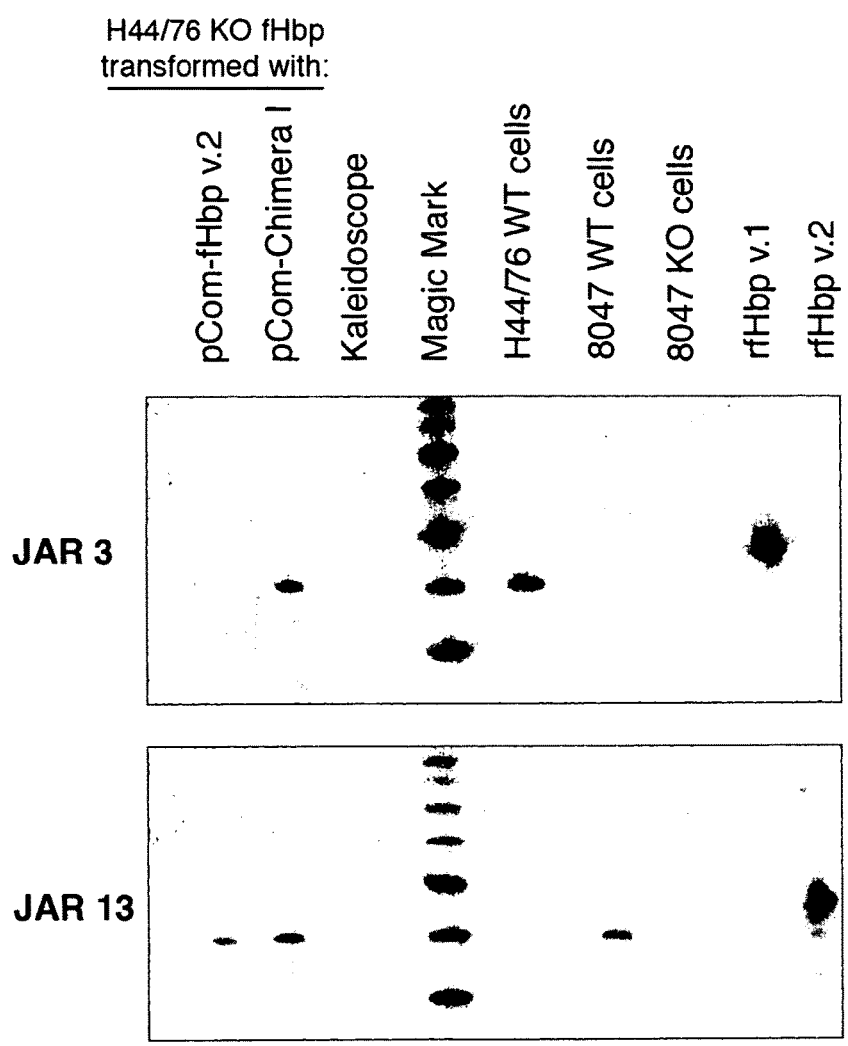
FIG. 33 provides an image of a Western blot of wildtype (WT) or Chimeric fHBP expressed in *N. meningitidis*. Lane 1, H44/76 KO fHBP transformed with pCom-fHBP v.2 WT plasmid; 2, H44/76 KO fHbp transformed with pCom-Chimera I plasmid; 3, Kaleidoscope marker; 4, Magic Mark marker; 5, H44/76 (v.1) WT cells; 6, 8047 (v.2) WT cells; 7, 8047 KO fHBP cells; 8, recombinant (r) fHBP v.1 protein (gene from strain MC58); 9, rfHBP v.2 protein (gene from strain 8047). Upper panel, blot probed with anti-fHBP mAb JAR 3 (v.1); lower panel, blot probed with anti-fHBP mAb JAR 13 (v.2 or v.3).

FIG. 33 shows a Western blot of samples of N. meningitidis expressing either wildtype (WT) or a chimeric fHBP (Chimera I (see FIG. 23)). The Chimera I corresponded to a full-length fHBP and further included the signal sequence (but lacked any epitope tags, such as a Penta-His tag) As shown in FIG. 33, bacterial cells transformed with the plasmid containing the gene encoding Chimera I were positive for both anti-fHbp mAbs, whereas the cells from H44/76 transformed with the plasmid containing the gene encoding fHbp v.2 or WT H44/76 react only with JAR 3 (v.1) and the cells from 8047 react only with JAR 13 (v.2).

ATCC DEPOSIT

Hybridomas producing the JAR 4, JAR 5, JAR 11, and JAR 32 monoclonal antibodies were deposited under the terms of the Budapest Treaty with the American Type Culture Collection, 10801 University Blvd., Manassas, Va. 20110-2209, USA (ATCC) on the date indicated in the table below, and were assigned the designations set out in the table below.

| ATCC Deposit No. (Deposit Date) | Material Deposited |
|---|---|
| PTA-8943 (Feb. 7, 2008) | Hybridoma producing JAR 4 Monoclonal Antibody |
| PTA-8941 (Feb. 7, 2008) | Hybridoma producing JAR 5 Monoclonal Antibody |

-continued

| ATCC Deposit No. (Deposit Date) | Material Deposited |
|---|---|
| PTA-8940 (Feb. 7, 2008) | Hybridoma producing JAR 10 Monoclonal Antibody |
| PTA-8938 (Feb. 7, 2008) | Hybridoma producing JAR 11 Monoclonal Antibody |
| PTA-8942 (Feb. 7, 2008) | Hybridoma producing JAR 32 Monoclonal Antibody |
| PTA-8939 (Feb. 7, 2008) | Hybridoma producing JAR 33 Monoclonal Antibody |

It should be noted that JAR 5 mAb specifically binds to an epitope that at least overlaps with the epitope specifically bound by JAR 3 mAb, and that JAR 32 mAb specifically binds to an epitope that at least overlaps with the epitope specifically bounds by JAR 35 mAb.

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Children's Hospital & Research Center at Oakland and the ATCC (the assignee of the present application) which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee(s) of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

What is claimed is:

1. A chimeric factor H binding protein (fHBP) comprising,
contiguously from its N-terminus to C-terminus:
a first amino acid sequence at least 90% identical to the contiguous amino acid sequence of SEQ ID NO: 4 from residue 94 to residue 128;
a GEHT (SEQ ID NO: 7) sequence; and
a second amino acid sequence at least 90% identical to the contiguous amino acid sequence of SEQ ID NO: 1 from residue 133 to residue 247;
wherein the chimeric fHBP comprises an epitope bound by JAR5 monoclonal antibody and an epitope bound by a monoclonal antibody specific for an epitope of v. 2 or v. 3 fHBP of a *Neisseria meningitidis* strain.

2. The chimeric fHBP of claim 1, wherein the chimeric fHBP comprises the amino acid sequence of an A domain of a v.1, v.2, or v.3 fHBP of *Neisseria meningitidis* positioned N-terminus of the first amino acid sequence.

3. The chimeric fHBP of claim 1, wherein the chimeric fHBP comprises at least one epitope that elicits an antibody that when specifically bound to a v.1, v.2, or v.3 fHBP of a *Neisseria meningitidis* strain blocks binding of human factor H (fH) to the fHBP.

4. The chimeric fHBP of claim 1, wherein the chimeric fHBP comprises a pair of epitopes that elicit antibodies that, when bound to their respective epitopes on fHBP of a *Neisseria meningitidis* strain, exhibit bactericidal activity against the *Neisseria meningitidis* strain.

5. The chimeric fHBP of claim 4, wherein the pair of epitopes is a JAR 10 monoclonal antibody epitope and a JAR 11 monoclonal antibody epitope.

6. An immunogenic composition comprising the chimeric fHBP according to claim 1 and a pharmaceutically acceptable excipient.

7. The immunogenic composition of claim 6, wherein the chimeric fHBP is in a vesicle preparation prepared from a *Neisseria meningitidis* strain.

* * * * *

SEQUENCE LISTING

```
<160> NUMBER OF SEQ ID NOS: 50

<210> SEQ ID NO 1
<211> LENGTH: 247
<212> TYPE: PRT
<213> ORGANISM: Artificial Sequence
<220> FEATURE:
<223> OTHER INFORMATION: Polypeptide

<400> SEQUENCE: 1

Val Ala Ala Asp Ile Gly Ala Arg Leu Ala Asp Ala Leu Thr Ala Pro
 1               5                  10                  15

Leu Asp His Lys Asp Lys Ser Leu Gln Ser Leu Thr Leu Asp Gln Ser
            20                  25                  30
```

```
Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 2
<211> LENGTH: 247
<212> TYPE: PRT
<213> ORGANISM: Artificial Sequence
<220> FEATURE:
<223> OTHER INFORMATION: Polypeptide

<400> SEQUENCE: 2

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ala Phe Asn Gln Leu Pro Asp Gly Lys Ala Glu Tyr
        130                 135                 140
```

```
His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 3
<211> LENGTH: 247
<212> TYPE: PRT
<213> ORGANISM: Artificial Sequence
<220> FEATURE:
<223> OTHER INFORMATION: Polypeptide

<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Lys Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245
```

```
<210> SEQ ID NO 4
<211> LENGTH: 248
<212> TYPE: PRT
<213> ORGANISM: Artificial Sequence
<220> FEATURE:
<223> OTHER INFORMATION: Polypeptide

<400> SEQUENCE: 4

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 5
<211> LENGTH: 7
<212> TYPE: PRT
<213> ORGANISM: Artificial Sequence
<220> FEATURE:
<223> OTHER INFORMATION: Polypeptide

<400> SEQUENCE: 5

Cys Ser Ser Gly Gly Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Polypeptide
```

```
<400> SEQUENCE: 6

Leu Glu His His His His His His
 1               5

<210> SEQ ID NO 7
<211> LENGTH: 4
<212> TYPE: PRT
<213> ORGANISM: Artificial Sequence
<220> FEATURE:
<223> OTHER INFORMATION: Polypeptide

<400> SEQUENCE: 7

Gly Glu His Thr
 1

<210> SEQ ID NO 8
<211> LENGTH: 46
<212> TYPE: PRT
<213> ORGANISM: Artificial Sequence
<220> FEATURE:
<223> OTHER INFORMATION: Polypeptide

<400> SEQUENCE: 8

Gln Ser His Ser Ala Leu Thr Ala Phe Gln Thr Glu Gln Ile Gln Asp
 1               5                  10                  15

Ser Glu His Ser Gly Lys Met Val Ala Lys Arg Gln Phe Arg Ile Gly
            20                  25                  30

Asp Ile Ala Gly Glu His Thr Ser Phe Asp Lys Leu Pro Glu
        35                  40                  45

<210> SEQ ID NO 9
<211> LENGTH: 46
<212> TYPE: PRT
<213> ORGANISM: Artificial Sequence
<220> FEATURE:
<223> OTHER INFORMATION: Polypeptide

<400> SEQUENCE: 9

Gln Ser His Ser Ala Leu Thr Ala Leu Gln Thr Glu Gln Val Gln Asp
 1               5                  10                  15

Ser Glu His Ser Gly Lys Met Val Ala Lys Arg Gln Phe Arg Ile Gly
            20                  25                  30

Asp Ile Ala Gly Glu His Thr Ser Phe Asp Lys Leu Pro Glu
        35                  40                  45

<210> SEQ ID NO 10
<211> LENGTH: 46
<212> TYPE: PRT
<213> ORGANISM: Artificial Sequence
<220> FEATURE:
<223> OTHER INFORMATION: Polypeptide

<400> SEQUENCE: 10

Gln Ser His Ser Ala Leu Thr Ala Leu Gln Thr Glu Gln Val Gln Asp
 1               5                  10                  15

Ser Glu Asp Ser Gly Lys Met Val Ala Lys Arg Gln Phe Arg Ile Gly
            20                  25                  30

Asp Ile Ala Gly Glu His Thr Ser Phe Asp Lys Leu Pro Lys
        35                  40                  45

<210> SEQ ID NO 11
<211> LENGTH: 46
<212> TYPE: PRT
```

<213> ORGANISM: Artificial Sequence
<220> FEATURE:
<223> OTHER INFORMATION: Polypeptide

<400> SEQUENCE: 11

Gln Ser His Ser Ala Leu Thr Ala Leu Gln Thr Glu Gln Val Gln Asp
1               5                   10                  15

Ser Glu His Ser Arg Lys Met Val Ala Lys Arg Gln Phe Arg Ile Gly
            20                  25                  30

Asp Ile Ala Gly Glu His Thr Ser Phe Asp Lys Leu Pro Lys
        35                  40                  45

<210> SEQ ID NO 12
<211> LENGTH: 46
<212> TYPE: PRT
<213> ORGANISM: Artificial Sequence
<220> FEATURE:
<223> OTHER INFORMATION: Polypeptide

<400> SEQUENCE: 12

Gln Ser His Ser Ala Leu Thr Ala Leu Gln Thr Glu Gln Glu Gln Asp
1               5                   10                  15

Pro Glu His Ser Gly Lys Met Val Ala Lys Arg Arg Phe Lys Ile Gly
            20                  25                  30

Asp Ile Ala Gly Glu His Thr Ser Phe Asp Lys Leu Pro Lys
        35                  40                  45

<210> SEQ ID NO 13
<211> LENGTH: 46
<212> TYPE: PRT
<213> ORGANISM: Artificial Sequence
<220> FEATURE:
<223> OTHER INFORMATION: Polypeptide

<400> SEQUENCE: 13

Gln Ser His Ser Ala Leu Thr Ala Leu Gln Thr Glu Gln Val Gln Asp
1               5                   10                  15

Ser Glu His Ser Gly Lys Met Val Ala Lys Arg Gln Phe Arg Ile Gly
            20                  25                  30

Asp Ile Val Gly Glu His Thr Ser Phe Gly Lys Leu Pro Lys
        35                  40                  45

<210> SEQ ID NO 14
<211> LENGTH: 46
<212> TYPE: PRT
<213> ORGANISM: Artificial Sequence
<220> FEATURE:
<223> OTHER INFORMATION: Polypeptide

<400> SEQUENCE: 14

Gln Ser His Ser Ala Leu Thr Ala Leu Gln Thr Glu Gln Glu Gln Asp
1               5                   10                  15

Pro Glu His Ser Glu Lys Met Val Ala Lys Arg Arg Phe Arg Ile Gly
            20                  25                  30

Asp Ile Ala Gly Glu His Thr Ser Phe Asp Lys Leu Pro Lys
        35                  40                  45

<210> SEQ ID NO 15
<211> LENGTH: 46
<212> TYPE: PRT
<213> ORGANISM: Artificial Sequence
<220> FEATURE:
<223> OTHER INFORMATION: Polypeptide

<400> SEQUENCE: 15

Gln Ser His Ser Ala Leu Thr Ala Leu Gln Thr Glu Gln Val Gln Asp
1               5                   10                  15

Ser Glu His Ser Gly Ser Met Val Ala Lys Arg Gln Phe Arg Ile Gly
            20                  25                  30

Asp Ile Ala Gly Glu His Thr Ser Phe Asp Lys Leu Pro Glu
        35                  40                  45

<210> SEQ ID NO 16
<211> LENGTH: 115
<212> TYPE: PRT
<213> ORGANISM: Artificial Sequence
<220> FEATURE:
<223> OTHER INFORMATION: Polypeptide

<400> SEQUENCE: 16

Ala Phe Asn Gln Leu Pro Asp Gly Lys Ala Glu Tyr His Gly Lys Ala
1               5                   10                  15

Phe Ser Ser Asp Asp Ala Gly Gly Lys Leu Thr Tyr Thr Ile Asp Phe
            20                  25                  30

Ala Ala Lys Gln Gly His Gly Lys Ile Glu His Leu Lys Thr Pro Glu
        35                  40                  45

Gln Asn Val Glu Leu Ala Ala Ala Glu Leu Lys Ala Asp Glu Lys Ser
    50                  55                  60

His Ala Val Ile Leu Gly Asp Thr Arg Tyr Gly Ser Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Lys Ile Gly Glu Lys Val His Glu Ile Gly Ile Ala
            100                 105                 110

Gly Lys Gln
        115

<210> SEQ ID NO 17
<211> LENGTH: 115
<212> TYPE: PRT
<213> ORGANISM: Artificial Sequence
<220> FEATURE:
<223> OTHER INFORMATION: Polypeptide

<400> SEQUENCE: 17

Ala Phe Asn Gln Leu Pro Asp Gly Lys Ala Glu Tyr His Gly Lys Ala
1               5                   10                  15

Phe Ser Ser Asp Asp Ala Gly Gly Lys Leu Thr Tyr Thr Ile Asp Phe
            20                  25                  30

Ala Ala Lys Gln Gly His Gly Lys Ile Glu His Leu Lys Thr Pro Glu
        35                  40                  45

Gln Asn Val Glu Leu Ala Ala Ala Glu Leu Lys Ala Asp Glu Lys Ser
    50                  55                  60

His Ala Val Ile Leu Gly Asp Thr Arg Tyr Gly Ser Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Glu Ile Gly Glu Lys Val His Glu Ile Gly Ile Ala
            100                 105                 110

Gly Lys Gln
        115

```
<210> SEQ ID NO 18
<211> LENGTH: 115
<212> TYPE: PRT
<213> ORGANISM: Artificial Sequence
<220> FEATURE:
<223> OTHER INFORMATION: Polypeptide

<400> SEQUENCE: 18

Ala Phe Asn Gln Leu Pro Ser Gly Lys Ala Glu Tyr His Gly Lys Ala
 1               5                  10                  15

Phe Ser Ser Asp Asp Ala Gly Gly Lys Leu Thr Tyr Thr Ile Asp Phe
                20                  25                  30

Ala Thr Lys Gln Gly His Gly Lys Ile Glu His Leu Lys Thr Pro Glu
        35                  40                  45

Gln Asn Val Glu Leu Ala Ala Ala Glu Leu Lys Ala Asp Glu Lys Ser
    50                  55                  60

His Ala Val Ile Leu Gly Asp Thr Arg Tyr Gly Ser Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Lys Ile Gly Glu Lys Val His Glu Ile Gly Ile Ala
            100                 105                 110

Gly Lys Gln
        115

<210> SEQ ID NO 19
<211> LENGTH: 115
<212> TYPE: PRT
<213> ORGANISM: Artificial Sequence
<220> FEATURE:
<223> OTHER INFORMATION: Polypeptide

<400> SEQUENCE: 19

Ala Phe Asn Gln Leu Pro Ser Gly Lys Ala Glu Tyr His Gly Lys Ala
 1               5                  10                  15

Phe Ser Ser Asp Asp Ala Gly Gly Lys Leu Thr Tyr Thr Ile Asp Phe
                20                  25                  30

Ala Ala Lys Gln Gly His Gly Lys Ile Glu His Leu Lys Thr Pro Glu
        35                  40                  45

Gln Asn Val Glu Leu Ala Ser Ala Glu Leu Lys Ala Asp Glu Lys Ser
    50                  55                  60

His Ala Val Ile Leu Gly Asp Thr Arg Tyr Gly Gly Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Lys Ile Arg Glu Lys Val His Glu Ile Gly Ile Ala
            100                 105                 110

Gly Lys Gln
        115

<210> SEQ ID NO 20
<211> LENGTH: 115
<212> TYPE: PRT
<213> ORGANISM: Artificial Sequence
<220> FEATURE:
<223> OTHER INFORMATION: Polypeptide

<400> SEQUENCE: 20
```

```
Ala Phe Asn Gln Leu Pro Ser Gly Lys Ala Glu Tyr His Gly Lys Ala
1               5                   10                  15

Phe Ser Ser Asp Asp Pro Asn Gly Arg Leu His Tyr Ser Ile Asp Phe
            20                  25                  30

Thr Lys Lys Gln Gly Tyr Gly Arg Ile Glu His Leu Lys Thr Pro Glu
            35                  40                  45

Gln Asn Val Glu Leu Ala Ser Ala Glu Leu Lys Ala Asp Glu Lys Ser
            50                  55                  60

His Ala Val Ile Leu Gly Asp Thr Arg Tyr Gly Gly Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Lys Ile Arg Glu Lys Val His Glu Ile Gly Ile Ala
                100                 105                 110

Gly Lys Gln
        115

<210> SEQ ID NO 21
<211> LENGTH: 115
<212> TYPE: PRT
<213> ORGANISM: Artificial Sequence
<220> FEATURE:
<223> OTHER INFORMATION: Polypeptide

<400> SEQUENCE: 21

Ala Phe Asn Gln Leu Pro Gly Gly Lys Ala Glu Tyr His Gly Lys Ala
1               5                   10                  15

Phe Ser Ser Asp Asp Ala Gly Gly Lys Leu Thr Tyr Thr Ile Asp Phe
            20                  25                  30

Ala Ser Lys Gln Gly His Gly Lys Ile Glu His Leu Lys Thr Pro Glu
            35                  40                  45

Gln Asn Val Glu Leu Ala Ala Ala Glu Leu Lys Ala Asp Glu Lys Ser
            50                  55                  60

His Ala Val Ile Leu Gly Asp Thr Arg Tyr Gly Ser Glu Glu Lys Gly
65                  70                  75                  80

Thr Tyr His Leu Ala Leu Phe Gly Asp Arg Ala Gln Glu Ile Ala Gly
                85                  90                  95

Ser Ala Thr Val Lys Ile Gly Glu Lys Val His Glu Ile Gly Ile Ala
                100                 105                 110

Gly Lys Gln
        115

<210> SEQ ID NO 22
<211> LENGTH: 115
<212> TYPE: PRT
<213> ORGANISM: Artificial Sequence
<220> FEATURE:
<223> OTHER INFORMATION: Polypeptide

<400> SEQUENCE: 22

Ala Phe Asn Gln Leu Pro Gly Gly Lys Ala Glu Tyr His Gly Lys Ala
1               5                   10                  15

Phe Ser Ser Asp Asp Pro Asn Gly Arg Leu His Tyr Ser Ile Asp Phe
            20                  25                  30

Thr Lys Lys Gln Gly Tyr Gly Arg Ile Glu His Leu Lys Thr Leu Glu
            35                  40                  45

Gln Asn Val Glu Leu Ala Ala Ala Glu Leu Lys Ala Asp Glu Lys Ser
            50                  55                  60
```

```
His Ala Val Ile Leu Gly Asp Thr Arg Tyr Gly Ser Glu Glu Lys Gly
 65                  70                  75                  80

Thr Tyr His Leu Ala Leu Phe Gly Asp Arg Ala Gln Glu Ile Ala Gly
                 85                  90                  95

Ser Ala Thr Val Lys Ile Gly Glu Lys Val His Glu Ile Gly Ile Ala
            100                 105                 110

Gly Lys Gln
        115

<210> SEQ ID NO 23
<211> LENGTH: 115
<212> TYPE: PRT
<213> ORGANISM: Artificial Sequence
<220> FEATURE:
<223> OTHER INFORMATION: Polypeptide

<400> SEQUENCE: 23

Ala Phe Asn Gln Leu Pro Ser Gly Lys Ala Glu Tyr His Gly Lys Ala
  1               5                  10                  15

Phe Ser Ser Asp Asp Ala Gly Gly Lys Leu Thr Tyr Thr Ile Asp Phe
                 20                  25                  30

Ala Ala Lys Gln Gly His Gly Lys Ile Glu His Leu Lys Thr Pro Glu
             35                  40                  45

Gln Asn Val Glu Leu Ala Ser Ala Glu Leu Lys Ala Asp Glu Lys Ser
 50                  55                  60

His Ala Val Ile Leu Gly Asp Thr Arg Tyr Gly Ser Glu Glu Lys Gly
 65                  70                  75                  80

Thr Tyr His Leu Ala Leu Phe Gly Asp Arg Ala Gln Glu Ile Ala Gly
                 85                  90                  95

Ser Ala Thr Val Lys Ile Arg Glu Lys Val His Glu Ile Gly Ile Ala
            100                 105                 110

Gly Lys Gln
        115

<210> SEQ ID NO 24
<211> LENGTH: 115
<212> TYPE: PRT
<213> ORGANISM: Artificial Sequence
<220> FEATURE:
<223> OTHER INFORMATION: Polypeptide

<400> SEQUENCE: 24

Ala Phe Asn Gln Leu Pro Asp Gly Lys Ala Glu Tyr His Gly Lys Ala
  1               5                  10                  15

Phe Ser Ser Asp Asp Ala Asp Gly Lys Leu Thr Tyr Thr Ile Asp Phe
                 20                  25                  30

Ala Ala Lys Gln Gly His Gly Lys Ile Glu His Leu Lys Thr Pro Glu
             35                  40                  45

Gln Asn Val Glu Leu Ala Ser Ala Glu Leu Lys Ala Asp Glu Lys Ser
 50                  55                  60

His Ala Val Ile Leu Gly Asp Thr Arg Tyr Gly Gly Glu Glu Lys Gly
 65                  70                  75                  80

Thr Tyr Arg Leu Ala Leu Phe Gly Asp Arg Ala Gln Glu Ile Ala Gly
                 85                  90                  95

Ser Ala Thr Val Lys Ile Gly Glu Lys Val His Glu Ile Gly Ile Ala
            100                 105                 110

Asp Lys Gln
```

<210> SEQ ID NO 25
<211> LENGTH: 49
<212> TYPE: PRT
<213> ORGANISM: Artificial Sequence
<220> FEATURE:
<223> OTHER INFORMATION: Polypeptide

<400> SEQUENCE: 25

```
Thr Glu Gln Glu Gln Asp Pro Glu His Ser Gly Lys Met Val Ala Lys
1               5                   10                  15

Arg Arg Phe Lys Ile Gly Asp Ile Ala Gly Glu His Thr Ala Phe Asn
            20                  25                  30

Gln Leu Pro Asp Gly Lys Ala Glu Tyr His Gly Lys Ala Phe Ser Ser
        35                  40                  45

Asp
```

<210> SEQ ID NO 26
<211> LENGTH: 49
<212> TYPE: PRT
<213> ORGANISM: Artificial Sequence
<220> FEATURE:
<223> OTHER INFORMATION: Polypeptide

<400> SEQUENCE: 26

```
Thr Glu Gln Ile Gln Asp Ser Glu His Ser Gly Lys Met Val Ala Lys
1               5                   10                  15

Arg Gln Phe Arg Ile Gly Asp Ile Ala Gly Glu His Thr Ala Phe Asn
            20                  25                  30

Gln Leu Pro Ser Gly Lys Ala Glu Tyr His Gly Lys Ala Phe Ser Ser
        35                  40                  45

Asp
```

<210> SEQ ID NO 27
<211> LENGTH: 49
<212> TYPE: PRT
<213> ORGANISM: Artificial Sequence
<220> FEATURE:
<223> OTHER INFORMATION: Polypeptide

<400> SEQUENCE: 27

```
Thr Glu Gln Glu Gln Asp Pro Glu His Ser Gly Lys Met Val Ala Lys
1               5                   10                  15

Arg Arg Phe Lys Ile Gly Asp Ile Ala Gly Glu His Thr Ala Phe Asn
            20                  25                  30

Gln Leu Pro Ser Gly Lys Ala Glu Tyr His Gly Lys Ala Phe Ser Ser
        35                  40                  45

Asp
```

<210> SEQ ID NO 28
<211> LENGTH: 274
<212> TYPE: PRT
<213> ORGANISM: Neisseria Meningitidis
<220> FEATURE:
<223> OTHER INFORMATION: Polypeptide

<400> SEQUENCE: 28

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
```

```
        20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
            130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 29
<211> LENGTH: 64
<212> TYPE: PRT
<213> ORGANISM: Artificial Sequence
<220> FEATURE:
<223> OTHER INFORMATION: Polypeptide

<400> SEQUENCE: 29

Gln Ser His Ser Ala Leu Thr Ala Phe Gln Thr Glu Gln Ile Gln Asp
 1               5                   10                  15

Ser Glu His Ser Gly Lys Met Val Ala Lys Arg Gln Phe Arg Ile Gly
                20                  25                  30

Asp Ile Ala Gly Glu His Thr Ser Phe Asp Lys Leu Pro Glu Gly Gly
            35                  40                  45

Arg Ala Thr Tyr Arg Gly Thr Ala Phe Gly Ser Asp Asp Ala Gly Gly
        50                  55                  60

<210> SEQ ID NO 30
<211> LENGTH: 90
<212> TYPE: PRT
<213> ORGANISM: Artificial Sequence
<220> FEATURE:
<223> OTHER INFORMATION: Polypeptide
```

```
<400> SEQUENCE: 30

Leu Thr Tyr Thr Ile Asp Phe Ala Ala Lys Gln Gly Asn Gly Lys Ile
1               5                   10                  15

Glu His Leu Lys Ser Pro Glu Leu Asn Val Asp Leu Ala Ala Ala Asp
            20                  25                  30

Ile Lys Pro Asp Gly Lys Arg His Ala Val Ile Ser Gly Ser Val Leu
        35                  40                  45

Tyr Asn Gln Ala Glu Lys Gly Ser Tyr Ser Leu Gly Ile Phe Gly Gly
    50                  55                  60

Lys Ala Gln Glu Val Ala Gly Ser Ala Glu Val Lys Thr Val Asn Gly
65                  70                  75                  80

Ile Arg His Ile Gly Leu Ala Ala Lys Gln
                85                  90

<210> SEQ ID NO 31
<211> LENGTH: 744
<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 31 gtc gcc gcc gac atc ggt gcg ggg ctt gcc gat gca cta acc gca ccg      48
Val Ala Ala Asp Ile Gly Ala Gly Leu Ala Asp Ala Leu Thr Ala Pro
1               5                   10                  15 ctc gac cat aaa gac aaa ggt ttg cag tct ttg acg ctg gat cag tcc      96
Leu Asp His Lys Asp Lys Gly Leu Gln Ser Leu Thr Leu Asp Gln Ser
            20                  25                  30 gtc agg aaa aac gag aaa ctg aag ctg gcg gca caa ggt gcg gaa aaa     144
Val Arg Lys Asn Glu Lys Leu Lys Leu Ala Ala Gln Gly Ala Glu Lys
        35                  40                  45 act tat gga aac ggt gac agc ctc aat acg ggc aaa ttg aag aac gac     192
Thr Tyr Gly Asn Gly Asp Ser Leu Asn Thr Gly Lys Leu Lys Asn Asp
    50                  55                  60 aag gtc agc cgt ttc gac ttt atc cgc caa atc gaa gtg gac ggg cag     240
Lys Val Ser Arg Phe Asp Phe Ile Arg Gln Ile Glu Val Asp Gly Gln
65                  70                  75                  80 ctc att acc ttg gag agt gga gag ttc caa gta tac aaa caa agc cat     288
Leu Ile Thr Leu Glu Ser Gly Glu Phe Gln Val Tyr Lys Gln Ser His
                85                  90                  95 tcc gcc tta acc gcc ttt cag acc gag caa ata caa gat tcg gag cat     336
Ser Ala Leu Thr Ala Phe Gln Thr Glu Gln Ile Gln Asp Ser Glu His
            100                 105                 110 tcc ggg aag atg gtt gcg aaa cgc cag ttc aga atc ggc gac ata gcg     384
Ser Gly Lys Met Val Ala Lys Arg Gln Phe Arg Ile Gly Asp Ile Ala
        115                 120                 125 gga gaa cat acc gcc ttc aac caa ctg cct gac ggc aaa gcc gag tat     432
Gly Glu His Thr Ala Phe Asn Gln Leu Pro Asp Gly Lys Ala Glu Tyr
    130                 135                 140 cac ggc aaa gca ttc agc tcc gac gat gct ggc gga aaa ctg acc tat     480
His Gly Lys Ala Phe Ser Ser Asp Asp Ala Gly Gly Lys Leu Thr Tyr
145                 150                 155                 160 acc ata gat ttc gcc gcc aaa cag gga cac ggc aaa atc gaa cac ctg     528
Thr Ile Asp Phe Ala Ala Lys Gln Gly His Gly Lys Ile Glu His Leu
                165                 170                 175 aaa aca ccc gag caa aat gtc gag ctt gcc gcc gcc gaa ctc aaa gca     576
Lys Thr Pro Glu Gln Asn Val Glu Leu Ala Ala Ala Glu Leu Lys Ala
```

```
                  180                 185                 190
gat gaa aaa tca cac gcc gtc att ttg ggc gac acg cgc tac ggc agc      624
Asp Glu Lys Ser His Ala Val Ile Leu Gly Asp Thr Arg Tyr Gly Ser
            195                 200                 205 gaa gaa aaa ggc act tac cac ctc gcc ctt ttc ggc gac cgc gcc caa      672
Glu Glu Lys Gly Thr Tyr His Leu Ala Leu Phe Gly Asp Arg Ala Gln
        210                 215                 220 gaa atc gcc ggc tcg gca acc gtg aag ata ggg gaa aag gtt cac gaa      720
Glu Ile Ala Gly Ser Ala Thr Val Lys Ile Gly Glu Lys Val His Glu
225                 230                 235                 240 atc ggc atc gcc ggc aaa cag tag                                      744
Ile Gly Ile Ala Gly Lys Gln *
                245

<210> SEQ ID NO 32
<211> LENGTH: 247
<212> TYPE: PRT
<213> ORGANISM: Artificial Sequence
<220> FEATURE:
<223> OTHER INFORMATION: Polypeptide

<400> SEQUENCE: 32

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 33
<211> LENGTH: 744
```

<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 33

```
gtc gcc gcc gac atc ggt gcg ggg ctt gcc gat gca cta acc gca ccg        48
Val Ala Ala Asp Ile Gly Ala Gly Leu Ala Asp Ala Leu Thr Ala Pro
1               5                   10                  15 ctc gac cat aaa gac aaa ggt ttg cag tct ttg acg ctg gat cag tcc        96
Leu Asp His Lys Asp Lys Gly Leu Gln Ser Leu Thr Leu Asp Gln Ser
            20                  25                  30 gtc agg aaa aac gag aaa ctg aag ctg gcg gca caa ggt gcg gaa aaa       144
Val Arg Lys Asn Glu Lys Leu Lys Leu Ala Ala Gln Gly Ala Glu Lys
        35                  40                  45 act tat gga aac ggt gac agc ctc aat acg ggc aaa ttg aag aac gac       192
Thr Tyr Gly Asn Gly Asp Ser Leu Asn Thr Gly Lys Leu Lys Asn Asp
    50                  55                  60 aag gtc agc cgt ttc gac ttt atc cgc caa atc gaa gtg gac ggg cag       240
Lys Val Ser Arg Phe Asp Phe Ile Arg Gln Ile Glu Val Asp Gly Gln
65                  70                  75                  80 ctc att acc ttg gag agt gga gag ttc caa gta tac aaa caa agc cat       288
Leu Ile Thr Leu Glu Ser Gly Glu Phe Gln Val Tyr Lys Gln Ser His
                85                  90                  95 tcc gcc tta acc gcc ttt cag acc gag caa ata caa gat tcg gag cat       336
Ser Ala Leu Thr Ala Phe Gln Thr Glu Gln Ile Gln Asp Ser Glu His
            100                 105                 110 tcc ggg aag atg gtt gcg aaa cgc cag ttc aga atc ggc gac ata gcg       384
Ser Gly Lys Met Val Ala Lys Arg Gln Phe Arg Ile Gly Asp Ile Ala
        115                 120                 125 gga gaa cat acc gcc ttc aac caa ctg cct gac ggc aaa gcc gag tat       432
Gly Glu His Thr Ala Phe Asn Gln Leu Pro Asp Gly Lys Ala Glu Tyr
    130                 135                 140 cac ggc aaa gca ttc agc tcc gac gat gct ggc gga aaa ctg acc tat       480
His Gly Lys Ala Phe Ser Ser Asp Asp Ala Gly Gly Lys Leu Thr Tyr
145                 150                 155                 160 acc ata gat ttc gcc aaa aaa cag gga cac ggc aaa atc gaa cac ctg       528
Thr Ile Asp Phe Ala Lys Lys Gln Gly His Gly Lys Ile Glu His Leu
                165                 170                 175 aaa aca ccc gag caa aat gtc gag ctt gcc gcc gcc gaa ctc aaa gca       576
Lys Thr Pro Glu Gln Asn Val Glu Leu Ala Ala Ala Glu Leu Lys Ala
            180                 185                 190 gat gaa aaa tca cac gcc gtc att ttg ggc gac acg cgc tac ggc agc       624
Asp Glu Lys Ser His Ala Val Ile Leu Gly Asp Thr Arg Tyr Gly Ser
        195                 200                 205 gaa gaa aaa ggc act tac cac ctc gcc ctt ttc ggc gac cgc gcc caa       672
Glu Glu Lys Gly Thr Tyr His Leu Ala Leu Phe Gly Asp Arg Ala Gln
    210                 215                 220 gaa atc gcc ggc tcg gca acc gtg aag ata ggg gaa aag gtt cac gaa       720
Glu Ile Ala Gly Ser Ala Thr Val Lys Ile Gly Glu Lys Val His Glu
225                 230                 235                 240 atc ggc atc gcc ggc aaa cag tag                                       744
Ile Gly Ile Ala Gly Lys Gln *
                245
```

<210> SEQ ID NO 34
<211> LENGTH: 247
<212> TYPE: PRT
<213> ORGANISM: Artificial Sequence

```
<220> FEATURE:
<223> OTHER INFORMATION: Polypeptide

<400> SEQUENCE: 34

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Lys Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 35
<211> LENGTH: 744
<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 35 gtc gcc gcc gac atc ggt gcg ggg ctt gcc gat gca cta acc gca ccg      48
Val Ala Ala Asp Ile Gly Ala Gly Leu Ala Asp Ala Leu Thr Ala Pro
1               5                   10                  15 ctc gac cat aaa gac aaa ggt ttg cag tct ttg acg ctg gat cag tcc      96
Leu Asp His Lys Asp Lys Gly Leu Gln Ser Leu Thr Leu Asp Gln Ser
            20                  25                  30 gtc agg aaa aac gag aaa ctg aag ctg gcg gca caa ggt gcg gaa aaa     144
Val Arg Lys Asn Glu Lys Leu Lys Leu Ala Ala Gln Gly Ala Glu Lys
        35                  40                  45 act tat gga aac ggt gac agc ctc aat acg ggc aaa ttg aag aac gac     192
```

```
Thr Tyr Gly Asn Gly Asp Ser Leu Asn Thr Gly Lys Leu Lys Asn Asp
         50                  55                  60 aag gtc agc cgt ttc gac ttt atc cgc caa atc gaa gtg gac ggg cag      240
Lys Val Ser Arg Phe Asp Phe Ile Arg Gln Ile Glu Val Asp Gly Gln
 65                  70                  75                  80 ctc att acc ttg gag agt gga gag ttc caa gta tac aaa caa agc cat      288
Leu Ile Thr Leu Glu Ser Gly Glu Phe Gln Val Tyr Lys Gln Ser His
                 85                  90                  95 tcc gcc tta acc gcc ttt cag acc gag caa ata caa gat tcg gag cat      336
Ser Ala Leu Thr Ala Phe Gln Thr Glu Gln Ile Gln Asp Ser Glu His
            100                 105                 110 tcc ggg aag atg gtt gcg aaa cgc cag ttc aga atc ggc gac ata gcg      384
Ser Gly Lys Met Val Ala Lys Arg Gln Phe Arg Ile Gly Asp Ile Ala
        115                 120                 125 gga gaa cat acc gcc ttc aac caa ctg cct gac ggc aaa gcc gag tat      432
Gly Glu His Thr Ala Phe Asn Gln Leu Pro Asp Gly Lys Ala Glu Tyr
130                 135                 140 cac ggc aaa gca ttc agc tcc gac gat gct ggc gga aaa ctg acc tat      480
His Gly Lys Ala Phe Ser Ser Asp Asp Ala Gly Gly Lys Leu Thr Tyr
145                 150                 155                 160 acc ata gat ttc gcc aaa aaa cag gga cac ggc aga atc gaa cac ctg      528
Thr Ile Asp Phe Ala Lys Lys Gln Gly His Gly Arg Ile Glu His Leu
                165                 170                 175 aaa aca ccc gag caa aat gtc gag ctt gcc gcc gcc gaa ctc aaa gca      576
Lys Thr Pro Glu Gln Asn Val Glu Leu Ala Ala Ala Glu Leu Lys Ala
            180                 185                 190 gat gaa aaa tca cac gcc gtc att ttg ggc gac acg cgc tac ggc agc      624
Asp Glu Lys Ser His Ala Val Ile Leu Gly Asp Thr Arg Tyr Gly Ser
        195                 200                 205 gaa gaa aaa ggc act tac cac ctc gcc ctt ttc ggc gac cgc gcc caa      672
Glu Glu Lys Gly Thr Tyr His Leu Ala Leu Phe Gly Asp Arg Ala Gln
210                 215                 220 gaa atc gcc ggc tcg gca acc gtg aag ata ggg gaa aag gtt cac gaa      720
Glu Ile Ala Gly Ser Ala Thr Val Lys Ile Gly Glu Lys Val His Glu
225                 230                 235                 240 atc ggc atc gcc ggc aaa cag tag                                      744
Ile Gly Ile Ala Gly Lys Gln  *
                245

<210> SEQ ID NO 36
<211> LENGTH: 247
<212> TYPE: PRT
<213> ORGANISM: Artificial Sequence
<220> FEATURE:
<223> OTHER INFORMATION: Polypeptide

<400> SEQUENCE: 36

Val Ala Ala Asp Ile Gly Ala Gly Leu Ala Asp Ala Leu Thr Ala Pro
  1               5                  10                  15

Leu Asp His Lys Asp Lys Gly Leu Gln Ser Leu Thr Leu Asp Gln Ser
             20                  25                  30

Val Arg Lys Asn Glu Lys Leu Lys Ala Ala Gln Gly Ala Glu Lys
             35                  40                  45

Thr Tyr Gly Asn Gly Asp Ser Leu Asn Thr Gly Lys Leu Lys Asn Asp
         50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95
```

```
Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Ala Gly Gly Lys Leu Thr Tyr
145                 150                 155                 160

Thr Ile Asp Phe Ala Lys Lys Gln Gly His Gly Arg Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245
```

<210> SEQ ID NO 37
<211> LENGTH: 744
<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 37

```
gtc gcc gcc gac atc ggc gcg ggg ctt gcc gat gca cta acc gca ccg      48
Val Ala Ala Asp Ile Gly Ala Gly Leu Ala Asp Ala Leu Thr Ala Pro
1               5                   10                  15 ctc gac cat aaa gac aaa agt ttg cag tct ttg acg ctg gat cag tcc      96
Leu Asp His Lys Asp Lys Ser Leu Gln Ser Leu Thr Leu Asp Gln Ser
            20                  25                  30 gtc agg aaa aac gag aaa ctg aag ctg gcg gca caa ggt gcg gaa aaa     144
Val Arg Lys Asn Glu Lys Leu Lys Leu Ala Ala Gln Gly Ala Glu Lys
        35                  40                  45 act tat gga aac ggc gac agc ctt aat acg ggc aaa ttg aag aac gac     192
Thr Tyr Gly Asn Gly Asp Ser Leu Asn Thr Gly Lys Leu Lys Asn Asp
    50                  55                  60 aag gtc agc cgt ttc gac ttt atc cgt caa atc gaa gtg gac ggg cag     240
Lys Val Ser Arg Phe Asp Phe Ile Arg Gln Ile Glu Val Asp Gly Gln
65                  70                  75                  80 ctc att acc ttg gag agc gga gag ttc caa gtg tac aaa caa agc cat     288
Leu Ile Thr Leu Glu Ser Gly Glu Phe Gln Val Tyr Lys Gln Ser His
                85                  90                  95 tcc gcc tta acc gcc ctt cag acc gag caa gaa caa gat cca gag cat     336
Ser Ala Leu Thr Ala Leu Gln Thr Glu Gln Glu Gln Asp Pro Glu His
            100                 105                 110 tcc ggg aag atg gtt gcg aaa cgc cgg ttc aaa atc ggc gac ata gcg     384
Ser Gly Lys Met Val Ala Lys Arg Arg Phe Lys Ile Gly Asp Ile Ala
        115                 120                 125 gga gaa cat acc gcc ttc aac caa ctg cct gac ggc aaa gcc gag tat     432
Gly Glu His Thr Ala Phe Asn Gln Leu Pro Asp Gly Lys Ala Glu Tyr
    130                 135                 140
```

```
cac ggc aaa gca ttc agc tcc gac gat gct ggc gga aaa ctg acc tat     480
His Gly Lys Ala Phe Ser Ser Asp Asp Ala Gly Gly Lys Leu Thr Tyr
145                 150                 155                 160 acc ata gat ttc gcc gcc aaa cag gga cac ggc aaa atc gaa cac ctg     528
Thr Ile Asp Phe Ala Ala Lys Gln Gly His Gly Lys Ile Glu His Leu
                165                 170                 175 aaa aca ccc gag caa aat gtc gag ctt gcc gcc gcc gaa ctc aaa gca     576
Lys Thr Pro Glu Gln Asn Val Glu Leu Ala Ala Ala Glu Leu Lys Ala
            180                 185                 190 gat gaa aaa tca cac gcc gtc att ttg ggc gac acg cgc tac ggc agc     624
Asp Glu Lys Ser His Ala Val Ile Leu Gly Asp Thr Arg Tyr Gly Ser
        195                 200                 205 gaa gaa aaa ggc act tac cac ctc gcc ctt ttc ggc gac cgc gcc caa     672
Glu Glu Lys Gly Thr Tyr His Leu Ala Leu Phe Gly Asp Arg Ala Gln
    210                 215                 220 gaa atc gcc ggc tcg gca acc gtg aag ata ggg gaa aag gtt cac gaa     720
Glu Ile Ala Gly Ser Ala Thr Val Lys Ile Gly Glu Lys Val His Glu
225                 230                 235                 240 atc ggc atc gcc ggc aaa cag tag                                      744
Ile Gly Ile Ala Gly Lys Gln *
                245

<210> SEQ ID NO 38
<211> LENGTH: 247
<212> TYPE: PRT
<213> ORGANISM: Artificial Sequence
<220> FEATURE:
<223> OTHER INFORMATION: Polypeptide

<400> SEQUENCE: 38

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Glu Gln Asp Pro Glu His
            100                 105                 110

Ser Gly Lys Met Val Ala Lys Arg Arg Phe Lys Ile Gly Asp Ile Ala
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220
```

Glu Ile Ala Gly Ser Ala Thr Val Lys Ile Gly Lys Val His Glu
225                 230                 235                 240

Ile Gly Ile Ala Gly Lys Gln
                245

<210> SEQ ID NO 39
<211> LENGTH: 744
<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 39

```
gtc gcc gcc gac atc ggt gcg ggg ctt gcc gat gca cta acc gca ccg      48
Val Ala Ala Asp Ile Gly Ala Gly Leu Ala Asp Ala Leu Thr Ala Pro
1               5                   10                  15 ctc gac cat aaa gac aaa ggt ttg cag tct ttg acg ctg gat cag tcc      96
Leu Asp His Lys Asp Lys Gly Leu Gln Ser Leu Thr Leu Asp Gln Ser
                20                  25                  30 gtc agg aaa aac gag aaa ctg aag ctg gcg gca caa ggt gcg gaa aaa     144
Val Arg Lys Asn Glu Lys Leu Lys Leu Ala Ala Gln Gly Ala Glu Lys
            35                  40                  45 act tat gga aac ggt gac agc ctc aat acg ggc aaa ttg aag aac gac     192
Thr Tyr Gly Asn Gly Asp Ser Leu Asn Thr Gly Lys Leu Lys Asn Asp
        50                  55                  60 aag gtc agc cgt ttc gac ttt atc cgc caa atc gaa gtg gac ggg cag     240
Lys Val Ser Arg Phe Asp Phe Ile Arg Gln Ile Glu Val Asp Gly Gln
65                  70                  75                  80 ctc att acc ttg gag agt gga gag ttc caa gta tac aaa caa agc cat     288
Leu Ile Thr Leu Glu Ser Gly Glu Phe Gln Val Tyr Lys Gln Ser His
                85                  90                  95 tcc gcc tta acc gcc ttt cag acc gag caa ata caa gat tcg gag cat     336
Ser Ala Leu Thr Ala Phe Gln Thr Glu Gln Ile Gln Asp Ser Glu His
                100                 105                 110 tcc ggg aag atg gtt gcg aaa cgc cag ttc aga atc ggc gac ata gcg     384
Ser Gly Lys Met Val Ala Lys Arg Gln Phe Arg Ile Gly Asp Ile Ala
            115                 120                 125 gga gaa cat acc gcc ttc aac caa ctg ccc agc ggc aaa gcc gag tat     432
Gly Glu His Thr Ala Phe Asn Gln Leu Pro Ser Gly Lys Ala Glu Tyr
        130                 135                 140 cac ggc aaa gca ttc agc tcc gac gac ccg aac ggc agg ctg cac tac     480
His Gly Lys Ala Phe Ser Ser Asp Asp Pro Asn Gly Arg Leu His Tyr
145                 150                 155                 160 tcc att gat ttt acc aaa aaa cag ggt tac ggc aga atc gaa cac ctg     528
Ser Ile Asp Phe Thr Lys Lys Gln Gly Tyr Gly Arg Ile Glu His Leu
                165                 170                 175 aaa acg ccc gag cag aat gtc gag ctt gcc tcc gcc gaa ctc aaa gca     576
Lys Thr Pro Glu Gln Asn Val Glu Leu Ala Ser Ala Glu Leu Lys Ala
                180                 185                 190 gat gaa aaa tca cac gcc gtc att ttg ggc gac acg cgc tac ggc ggc     624
Asp Glu Lys Ser His Ala Val Ile Leu Gly Asp Thr Arg Tyr Gly Gly
            195                 200                 205 gaa gaa aaa ggc act tac cac ctc gcc ctt ttc ggc gac cgc gcc caa     672
Glu Glu Lys Gly Thr Tyr His Leu Ala Leu Phe Gly Asp Arg Ala Gln
        210                 215                 220 gaa atc gcc ggc tcg gca acc gtg aag ata agg gaa aag gtt cac gaa     720
Glu Ile Ala Gly Ser Ala Thr Val Lys Ile Arg Glu Lys Val His Glu
225                 230                 235                 240
```

```
atc ggc atc gcc ggc aaa cag tag                              744
Ile Gly Ile Ala Gly Lys Gln *
                245
```

<210> SEQ ID NO 40
<211> LENGTH: 247
<212> TYPE: PRT
<213> ORGANISM: Artificial Sequence
<220> FEATURE:
<223> OTHER INFORMATION: Polypeptide

<400> SEQUENCE: 40

```
Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ala Phe Asn Gln Leu Pro Ser Gly Lys Ala Glu Tyr
    130                 135                 140

His Gly Lys Ala Phe Ser Ser Asp Pro Asn Gly Arg Leu His Tyr
145                 150                 155                 160

Ser Ile Asp Phe Thr Lys Lys Gln Gly Tyr Gly Arg Ile Glu His Leu
                165                 170                 175

Lys Thr Pro Glu Gln Asn Val Glu Leu Ala Ser Ala Glu Leu Lys Ala
            180                 185                 190

Asp Glu Lys Ser His Ala Val Ile Leu Gly Asp Thr Arg Tyr Gly Gly
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Arg Glu Lys Val His Glu
225                 230                 235                 240

Ile Gly Ile Ala Gly Lys Gln
                245
```

<210> SEQ ID NO 41
<211> LENGTH: 744
<212> TYPE: DNA
<213> ORGANISM: Artificial Sequence
<220> FEATURE:
<223> OTHER INFORMATION: Polynucleotide
<220> FEATURE:
<221> NAME/KEY: CDS
<222> LOCATION: (1)...(744)

<400> SEQUENCE: 41

```
gtc gcc gcc gac atc ggc gcg ggg ctt gcc gat gca cta acc gca ccg    48
Val Ala Ala Asp Ile Gly Ala Gly Leu Ala Asp Ala Leu Thr Ala Pro
 1               5                  10                  15
```

```
ctc gac cat aaa gac aaa agt ttg cag tct ttg acg ctg gat cag tcc      96
Leu Asp His Lys Asp Lys Ser Leu Gln Ser Leu Thr Leu Asp Gln Ser
             20                  25                  30 gtc agg aaa aac gag aaa ctg aag ctg gcg gca caa ggt gcg gaa aaa     144
Val Arg Lys Asn Glu Lys Leu Lys Leu Ala Ala Gln Gly Ala Glu Lys
         35                  40                  45 act tat gga aac ggc gac agc ctt aat acg ggc aaa ttg aag aac gac     192
Thr Tyr Gly Asn Gly Asp Ser Leu Asn Thr Gly Lys Leu Lys Asn Asp
     50                  55                  60 aag gtc agc cgt ttc gac ttt atc cgt caa atc gaa gtg gac ggg cag     240
Lys Val Ser Arg Phe Asp Phe Ile Arg Gln Ile Glu Val Asp Gly Gln
 65                  70                  75                  80 ctc att acc ttg gag agc gga gag ttc caa gtg tac aaa caa agc cat     288
Leu Ile Thr Leu Glu Ser Gly Glu Phe Gln Val Tyr Lys Gln Ser His
                 85                  90                  95 tcc gcc tta acc gcc ctt cag acc gag caa gaa caa gat cca gag cat     336
Ser Ala Leu Thr Ala Leu Gln Thr Glu Gln Glu Gln Asp Pro Glu His
            100                 105                 110 tcc ggg aag atg gtt gcg aaa cgc cgg ttc aaa atc ggc gac ata gcg     384
Ser Gly Lys Met Val Ala Lys Arg Arg Phe Lys Ile Gly Asp Ile Ala
        115                 120                 125 gga gaa cat acc gcc ttc aac caa ctg ccc agc ggc aaa gcc gag tat     432
Gly Glu His Thr Ala Phe Asn Gln Leu Pro Ser Gly Lys Ala Glu Tyr
    130                 135                 140 cac ggc aaa gca ttc agc tcc gac gac ccg aac ggc agg ctg cac tac     480
His Gly Lys Ala Phe Ser Ser Asp Asp Pro Asn Gly Arg Leu His Tyr
145                 150                 155                 160 tcc att gat ttt acc aaa aaa cag ggt tac ggc aga atc gaa cac ctg     528
Ser Ile Asp Phe Thr Lys Lys Gln Gly Tyr Gly Arg Ile Glu His Leu
                165                 170                 175 aaa acg ccc gag cag aat gtc gag ctt gcc tcc gcc gaa ctc aaa gca     576
Lys Thr Pro Glu Gln Asn Val Glu Leu Ala Ser Ala Glu Leu Lys Ala
            180                 185                 190 gat gaa aaa tca cac gcc gtc att ttg ggc gac acg cgc tac ggc ggc     624
Asp Glu Lys Ser His Ala Val Ile Leu Gly Asp Thr Arg Tyr Gly Gly
        195                 200                 205 gaa gaa aaa ggc act tac cac ctc gcc ctt ttc ggc gac cgc gcc caa     672
Glu Glu Lys Gly Thr Tyr His Leu Ala Leu Phe Gly Asp Arg Ala Gln
    210                 215                 220 gaa atc gcc ggc tcg gca acc gtg aag ata agg gaa aag gtt cac gaa     720
Glu Ile Ala Gly Ser Ala Thr Val Lys Ile Arg Glu Lys Val His Glu
225                 230                 235                 240 atc ggc atc gcc ggc aaa cag tag                                     744
Ile Gly Ile Ala Gly Lys Gln *
                245

<210> SEQ ID NO 42
<211> LENGTH: 247
<212> TYPE: PRT
<213> ORGANISM: Artificial Sequence
<220> FEATURE:
<223> OTHER INFORMATION: Polypeptide

<400> SEQUENCE: 42

Val Ala Ala Asp Ile Gly Ala Gly Leu Ala Asp Ala Leu Thr Ala Pro
 1               5                  10                  15

Leu Asp His Lys Asp Lys Ser Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45
```

```
Thr Tyr Gly Asn Gly Asp Ser Leu Asn Thr Gly Lys Leu Lys Asn Asp
         50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Leu Gln Thr Gln Glu Gln Asp Pro Glu His
                100                 105                 110

Ser Gly Lys Met Val Ala Lys Arg Arg Phe Lys Ile Gly Asp Ile Ala
            115                 120                 125

Gly Glu His Thr Ala Phe Asn Gln Leu Pro Ser Gly Lys Ala Glu Tyr
        130                 135                 140

His Gly Lys Ala Phe Ser Ser Asp Asp Pro Asn Gly Arg Leu His Tyr
145                 150                 155                 160

Ser Ile Asp Phe Thr Lys Lys Gln Gly Tyr Gly Arg Ile Glu His Leu
                165                 170                 175

Lys Thr Pro Glu Gln Asn Val Glu Leu Ala Ser Ala Glu Leu Lys Ala
            180                 185                 190

Asp Glu Lys Ser His Ala Val Ile Leu Gly Asp Thr Arg Tyr Gly Gly
        195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Arg Glu Lys Val His Glu
225                 230                 235                 240

Ile Gly Ile Ala Gly Lys Gln
                245

<210> SEQ ID NO 43
<211> LENGTH: 8
<212> TYPE: PRT
<213> ORGANISM: Artificial Sequence
<220> FEATURE:
<223> OTHER INFORMATION: Polypeptide

<400> SEQUENCE: 43

Gly Glu His Thr Ser Phe Asp Lys
 1               5

<210> SEQ ID NO 44
<211> LENGTH: 22
<212> TYPE: PRT
<213> ORGANISM: Artificial Sequence
<220> FEATURE:
<223> OTHER INFORMATION: Polypeptide

<400> SEQUENCE: 44

Gln Ser His Ser Ala Leu Thr Ala Phe Gln Thr Glu Gln Ile Gln Asp
 1               5                  10                  15

Ser Glu His Ser Gly Lys
            20

<210> SEQ ID NO 45
<211> LENGTH: 22
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: 9
```

<223> OTHER INFORMATION: Xaa= F or L
<220> FEATURE:
<221> NAME/KEY: VARIANT
<222> LOCATION: 14
<223> OTHER INFORMATION: Xaa= I, V or E
<220> FEATURE:
<221> NAME/KEY: VARIANT
<222> LOCATION: 17
<223> OTHER INFORMATION: Xaa= S or P
<220> FEATURE:
<221> NAME/KEY: VARIANT
<222> LOCATION: 19
<223> OTHER INFORMATION: Xaa= H or D
<220> FEATURE:
<221> NAME/KEY: VARIANT
<222> LOCATION: 21
<223> OTHER INFORMATION: Xaa= G, E or R

<400> SEQUENCE: 45

Gln Ser His Ser Ala Leu Thr Ala Xaa Gln Thr Glu Gln Xaa Gln Asp
 1               5                  10                 15

Xaa Glu Xaa Ser Xaa Lys
            20

<210> SEQ ID NO 46
<211> LENGTH: 46
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: 9
<223> OTHER INFORMATION: Xaa= F or L
<220> FEATURE:
<221> NAME/KEY: VARIANT
<222> LOCATION: 14
<223> OTHER INFORMATION: Xaa= I, V or E
<220> FEATURE:
<221> NAME/KEY: VARIANT
<222> LOCATION: 17
<223> OTHER INFORMATION: Xaa= S or P
<220> FEATURE:
<221> NAME/KEY: VARIANT
<222> LOCATION: 19
<223> OTHER INFORMATION: Xaa= H or D
<220> FEATURE:
<221> NAME/KEY: VARIANT
<222> LOCATION: 21
<223> OTHER INFORMATION: Xaa= G, E or R
<220> FEATURE:
<221> NAME/KEY: VARIANT
<222> LOCATION: 28
<223> OTHER INFORMATION: Xaa= Q or R
<220> FEATURE:
<221> NAME/KEY: VARIANT
<222> LOCATION: 35
<223> OTHER INFORMATION: Xaa= A or V
<220> FEATURE:
<221> NAME/KEY: VARIANT
<222> LOCATION: 46
<223> OTHER INFORMATION: Xaa= D or S

<400> SEQUENCE: 46

Gln Ser His Ser Ala Leu Thr Ala Xaa Gln Thr Glu Gln Xaa Gln Asp
 1               5                  10                 15

Xaa Glu Xaa Ser Xaa Lys Met Val Ala Lys Arg Xaa Phe Arg Ile Gly
            20                  25                 30

Asp Ile Xaa Gly Glu His Thr Ala Phe Asn Gln Leu Pro Xaa
         35                  40                 45

<210> SEQ ID NO 47

```
<211> LENGTH: 36
<212> TYPE: PRT
<213> ORGANISM: Artificial Sequence
<220> FEATURE:
<223> OTHER INFORMATION: Polypeptide

<400> SEQUENCE: 47

Thr Glu Gln Ile Gln Asp Ser Glu His Ser Gly Lys Met Val Ala Lys
1               5                   10                  15

Arg Gln Phe Arg Ile Gly Asp Ile Ala Gly Glu His Thr Ala Phe Asn
            20                  25                  30

Gln Leu Pro Asp
        35

<210> SEQ ID NO 48
<211> LENGTH: 46
<212> TYPE: PRT
<213> ORGANISM: Artificial Sequence
<220> FEATURE:
<223> OTHER INFORMATION: Polypeptide

<400> SEQUENCE: 48

Gln Ser His Ser Ala Leu Thr Ala Phe Gln Thr Glu Gln Ile Gln Asp
1               5                   10                  15

Ser Glu His Ser Gly Lys Met Val Ala Lys Arg Gln Phe Arg Ile Gly
            20                  25                  30

Asp Ile Ala Gly Glu His Thr Ala Phe Asn Gln Leu Pro Asp
        35                  40                  45

<210> SEQ ID NO 49
<211> LENGTH: 30
<212> TYPE: PRT
<213> ORGANISM: Artificial Sequence
<220> FEATURE:
<223> OTHER INFORMATION: Polypeptide

<400> SEQUENCE: 49

Leu Thr Ala Phe Gln Thr Glu Gln Ile Gln Asp Ser Glu His Ser Gly
1               5                   10                  15

Lys Met Val Ala Lys Arg Gln Phe Arg Ile Gly Asp Ile Ala
            20                  25                  30

<210> SEQ ID NO 50
<211> LENGTH: 9
<212> TYPE: PRT
<213> ORGANISM: Artificial Sequence
<220> FEATURE:
<223> OTHER INFORMATION: Polypeptide

<400> SEQUENCE: 50

Lys Leu Thr Tyr Thr Ile Asp Phe Ala
1               5
```